(12) United States Patent
Schwink et al.

(10) Patent No.: US 7,141,561 B2
(45) Date of Patent: Nov. 28, 2006

(54) SUBSTITUTED DIARYL HETEROCYCLES, PROCESS FOR THEIR PREPARATION AND THEIR USE AS MEDICAMENTS

(75) Inventors: Lothar Schwink, Stadtallendorf (DE); Siegfried Stengelin, Eppstein (DE); Matthias Gossel, Hofheim (DE); Thomas Boehme, Russelsheim (DE); Gerhard Hessler, Hofheim (DE); Gerard Rosse, Oro Valley, AZ (US); Armin Walser, Tuscon, AZ (US)

(73) Assignee: Sanofi-Aventis Deutschland GmbH, Frankfurt (DE)

(*) Notice: Subject to any disclaimer, the term of this patent is extended or adjusted under 35 U.S.C. 154(b) by 199 days.

(21) Appl. No.: 10/626,314

(22) Filed: Jul. 24, 2003

(65) Prior Publication Data
US 2004/0132752 A1    Jul. 8, 2004

Related U.S. Application Data

(60) Provisional application No. 60/428,877, filed on Nov. 25, 2002.

(30) Foreign Application Priority Data
Jul. 25, 2002    (DE)    ................. 102 33 817

(51) Int. Cl.
A61K 31/397    (2006.01)
A61K 31/415    (2006.01)
C07D 417/10    (2006.01)
C07D 401/10    (2006.01)
C07D 233/02    (2006.01)

(52) U.S. Cl. ............... 514/212.03; 514/252.13; 514/269; 514/307; 514/317; 514/386; 514/389; 544/60; 546/208; 548/316.4

(58) Field of Classification Search ............. 548/316.4; 544/60; 546/208; 540/524; 514/212.03, 514/252.13, 307, 317, 269, 386, 389
See application file for complete search history.

(56) References Cited

U.S. PATENT DOCUMENTS

| 5,276,049 A * | 1/1994 | Himmelsbach et al. ..... 514/392 |
| 5,478,942 A | 12/1995 | Himmelsbach et al. |
| 5,650,424 A | 7/1997 | Himmelsbach et al. |
| 6,054,590 A | 4/2000 | Poindexter et al. |
| 2002/0042400 A1 | 4/2002 | Rong et al. |

FOREIGN PATENT DOCUMENTS

| EP | 0002649 | 6/1979 |
| EP | 0503548 | 9/1992 |
| WO | WO 96/25410 | 8/1996 |
| WO | WO 97/26265 | 7/1997 |
| WO | WO 97/41097 | 11/1997 |
| WO | WO 98/08871 | 3/1998 |
| WO | WO 98/58934 | 12/1998 |
| WO | WO 99/03861 | 1/1999 |
| WO | WO 02/10146 | 2/2002 |
| WO | WO 02/10141 | 7/2002 |
| WO | WO 02/051819 | 7/2002 |
| WO | WO 03/057220 | 7/2003 |

OTHER PUBLICATIONS

Audinott Valerie et al., Structure-Activity Relationship Studies of Melanin-concentrating Hormone (MCH)-related Peptide Ligands at SLC-1, the Human MCH Receptor, J. Biol. Chem., 2001, vol. 276, No. 17, pp. 13554-13562.
Chambers Jon et al., Melanin-concentrating hormone is the cognate ligand for the orphan G-protein-coupled receptor SLC-1, Nature, 1999, vol. 400, pp. 261-185.
Saito Yumiko et al., Molecular characterization of the melanin-concentrating-hormone receptor, Nature, 1999, vol. 400, pp. 265-269.
Donald J. Cram et al., Host-Guest Complexation. 31. A Transacylase Partial Mimic, J. Am. Chem. Soc. (1984, pp. 4987-5000, vol. 106).
Jon Chambers et al., Melanin-concentrating hormone is the cognate ligand for the orphan G-protein-coupled receptor SLC-1, Letters to Nature (1999, pp. 261-265, vol. 400).

(Continued)

Primary Examiner—Johann Richter
Assistant Examiner—Ebenezer Sackey
(74) Attorney, Agent, or Firm—Joseph Strupczewski; Lawrence L. Martin; Balaram Gupta

(57) ABSTRACT

This invention discloses and claims diary heterocycles of formula (I)

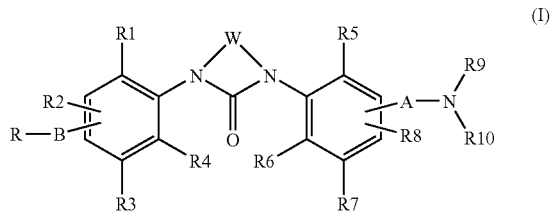

and their pharmaceutically acceptable salts, pharmaceutical compositions thereof, and methods of using said compounds of formula (I) for the treatment or prevention of excessive weight or obesity, and for treatment of Type II diabetes, arteriosclerosis, high blood pressure, depression, anxiety, anxiety neuroses, and schizophrenia. Methods for treatment of excessive weight or obesity and for treatment of Type II diabetes with a mixture of a compound of formula I and antiobesity agents or appetite-regulating active ingredients, or with a mixture of a compound of formula I and antidiabetics or hypoglycemic active ingredients are also disclosed and claimed.

17 Claims, No Drawings

OTHER PUBLICATIONS

Kent D. Stewart et al., Host-Guest Complexation. 40. Synthesis And Complexation of Macrocyclic Hosts Containing Cyclic Ureas, Anisyls, and Steric Barriers, The Journal of Organic Chemistry (1986, pp. 4327-4337, vol. 51, No. 23).

Roeland J. M. Nolte et al., Host-Guest Complexation. 27. Hosts Containing Only Cyclic Urea Binding Sites, J. Am. Chem. Soc. (1984, pp. 1416-1420, vol. 108).

Saito Yumiko et al., Molecular characterization of the melanin-concentrating-hormone receptor, Letters to Nature, (1999, pp. 265-269, vol. 400).

Valerie Audinot et al., Structure-Activity Relationship Studies of Melanin-concentrating Hormone (MCH)-related Peptide Ligands at SLC-1, the Human MCH Receptor, The Journal of Biological Chemistry (2001, pp. 13554-13562, vol. 276, No. 17).

* cited by examiner

SUBSTITUTED DIARYL HETEROCYCLES, PROCESS FOR THEIR PREPARATION AND THEIR USE AS MEDICAMENTS

CROSS-REFERENCE TO RELATED APPLICATIONS

This application claims the benefit of priority of German Patent Application No.10233817.5-44, filed Jul. 25, 2002, and the benefit of U.S. Provisional Application No.60/428,877, filed Nov. 25, 2002.

BACKGROUND OF THE INVENTION

1. Field of the Invention

The invention relates to substituted diaryl heterocycles and to their pharmaceutically acceptable salts and physiologically functional derivatives. The invention also relates to providing compounds which bring about a weight reduction in mammals and which are suitable for the prevention and treatment of obesity.

2. Description of the Art

Compounds having a pharmacological effect and similar in their overall structure to the diaryl heterocycles described herein have already been described in the prior art (such as, for example, U.S. Pat. No. 6,054,590A).

SUMMARY OF THE INVENTION

The invention therefore relates to compounds of the formula I

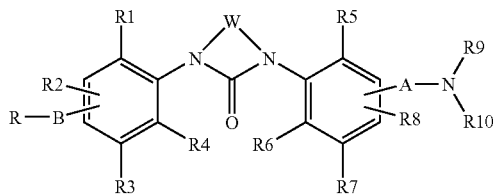

wherein
R is $(C_1-C_8)$-alkyl, $(C_0-C_8)$-alkylene-aryl, $(C_3-C_8)$-cycloalkyl, $(C_1-C_4)$-alkoxy-$(C_1-C_4)$-alkyl, $(C_2-C_8)$-alkenyl, $(C_2-C_8)$-alkynyl, a 3- to 12-membered mono-, bi- or spirocyclic ring optionally containing one or more heteroatoms selected from the group consisting of N, O, and S, and wherein the 3- to 12-membered ring is optionally substituted by F, Cl, Br, $NO_2$, $CF_3$, $OCF_3$, CN, $(C_1-C_6)$-alkyl, aryl, CON(R11)(R12), N(R13)(R14), OH, O—$(C_1-C_6)$-alkyl, S—$(C_1-C_6)$-alkyl, N(R15)CO $(C_1-C_6)$-alkyl or COO—$(C_1-C_6)$-alkyl;
R11, R12, R13, R14, R15 independently are H, or $(C_1-C_6)$-alkyl;
B is a bond or a linker consisting of one or two radicals selected from the group consisting of $(C(R19)(R20))_i$, C(OR21)(R22), O, N(R23), S, SO, $SO_2$ and CO;
i is 1, 2 or 3;
R19, R20, R21, R22, R23 independently are H, $(C_1-C_6)$-alkyl or aryl;
R1, R2, R3, R4 independently are H, F, Cl, Br, I, OH, $CF_3$, $NO_2$, CN, OCF3, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R24)(R25), $SO_2$—$CH_3$, COOH, COO—$(C_1-C_6)$-alkyl, CON(R26)(R27), N(R28)CO(R29), N(R30)$SO_2$(R31) or CO(R32);
R24, R25, R26, R27, R28, R30 independently are H or $(C_1-C_6)$-alkyl;
R29, R31, R32 independently are H, $(C_1-C_6)$-alkyl or aryl;
W is —$(CH_2)_n$—, —CH=CH—, —CH=N— or —N=CH—;
n is 2, 3, 4 or 5;
R5, R6, R7, R8 independently are H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R33)(R34), $SO_2$—$CH_3$, COOH, COO—$(C_1-C_6$CON(R35)(R36), N(R37) CO(R38), N(R39)$SO_2$(R40) or CO(R41), or a 5- to 7-membered heterocycle having 1 to 4 heteroatoms selected from the group consisting of O, N and S;
R33, R34 independently are H or $(C_1-C_6)$-alkyl;or
R33 and R34 form together with the nitrogen atom to which they are bonded a 5- or 6-membered ring, wherein when R33 and R34 form together with the nitrogen to which they are bonded a 6-membered ring, one $CH_2$ group optionally is O or S;
R35, R36, R37, R39 independently are H or $(C_1-C_6)$-alkyl;
R38, R40, R41 independently are H, $(C_1-C_6)$-alkyl or aryl;
A is a chain —$(C(R42)(R43))_m$- in which 0 to 2 members of the chain are optionally replaced by an element selected from the group consisting of O, S, N(R44), CO and $SO_2$;
m is 0, 1, 2, 3, 4 or 5;
R42, R43, R44 independently are H, $(C_1-C_6)$-alkyl or aryl;
R9, R10 independently are H, $(C_1-C_8)$-alkyl, —$(CH_2)_o$—R45, $(C_1-C_4)$-alkoxy-$(C_1-C_4)$-alkyl, aryloxy-$(C_1-C_4)$-alkyl, $(C_3-C_8)$-alkenyl, $(C_3-C_8)$-alkynyl, CO—$(C_1-C_8)$-alkyl, —CO—$(CH_2)_o$—R45, CO—$(C_1-C_4)$-alkoxy-$(C_1-C_4)$-alkyl, CO-aryloxy-$(C_1-C_4)$-alkyl, CO—$(C_2-C_8)$-alkenyl, CO—$(C_2-C_8)$-alkynyl, or
R9 and R10 form together with the nitrogen atom to which they are bonded a 4- to 10-membered mono-, bi- or spirocyclic ring wherein said ring, apart from the nitrogen atom, may optionally contain 0 to 4 additional heteroatoms selected from the group consisting of oxygen, nitrogen and sulfur and wherein said ring optionally is substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, $(C_0-C_8)$-alkylene-aryl, oxo, CO(R46), CON(R47)(R48), hydroxyl, COO(R49), N(R50)CO$(C_1-C_6)$-alkyl, N(R51)(R52) or $SO_2CH_3$;
R46, R47, R48, R49, R50, R51, R52 independently are H or $(C_1-C_6)$-alkyl;
o is 0, 1, 2, 3, 4, 5 or 6;
R45 is OH, $CH(aryl)_2$, a 3- to 12-membered mono- or bicyclic ring which optionally contains one or more heteroatoms selected from the group consisting of N, O and S, wherein the 3- to 12-membered ring optionally is substituted by F, Cl, Br, I, OH, $CF_3$, $NO_2$, CN, $OCF_3$, oxo, O—$(C_1-C_6)$-alkyl, $(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R51)(R52), $SO_2$—$CH_3$ or COOH; or
a pharmaceutically acceptable salt of the compound of formula I.

Preference is given to compounds of formula I wherein
R is $(C_1–C_6)$-alkyl, $(C_0–C_2)$-alkylene-aryl, $(C_3–C_8)$-cycloalkyl, $(C_2–C_6)$-alkenyl, $(C_5–C_8)$-cycloalkenyl, $(C_7–C_8)$-bicycloalkenyl, $(C_2–C_6)$-alkynyl; a 3- to 7-membered ring optionally containing one or more heteroatoms selected from the group consisting of of N, O and S, and wherein the 3- to 7-membered ring is optionally substituted by F, Cl, Br, $NO_2$, $CF_3$, $OCF_3$, CN, $(C_1–C_6)$-alkyl, $CON(R11)(R12)$, $N(R13)(R14)$, OH, O—$(C_1–C_6)$-alkyl, $N(R15)CO(C_1–C_6)$-alkyl or $COO(C_1–C_6)$-alkyl;

R11, R12, R13, R14, R15 independently are H or $(C_1–C_6)$-alkyl;

B is a bond, O, S, $SO_2$, CO, $OCH(R20)$, $N(R23)$, $CH_2$ or $CH_2CH_2$

R20, R23 independently are H or $(C_1–C_6)$-alkyl;

R1, R2, R3, R4 independently are H, F, Cl, Br, OH, $CF_3$, $NO_2$, CN, $OCF_3$, O—$(C_1–C_6)$-alkyl, O—$(C_1–C_4)$-alkoxy-$(C_1–C_4)$-alkyl, S—$(C_1–C_6)$-alkyl, $(C_1–C_6)$-alkyl, $(C_0–C_2)$-alkylene-aryl, O—$(C_0–C_2)$-alkylene-aryl, $N(R24)(R25)$, $SO_2$—$CH_3$, COOH, COO—$(C_1–C_6)$-alkyl, $CON(R26)(R27)$, $N(R28)CO(R29)$ or $CO(R32)$:

R24, R25, R26, R27, R28, R30 independently are H or $(C_1–C_6)$-alkyl;

R29, R32 independently are H, $(C_1–C_6)$-alkyl or aryl;

W is —$(CH_2)_n$—, —CH=CH—, —CH=N— or —N=CH—;

n is 2, 3 or 4;

R5, R6, R7, R8 independently are H, F, Cl, Br, OH, $CF_3$, $NO_2$, CN, $OCF_3$, O—$(C_1–C_6)$-alkyl, $(C_1–C_6)$-alkyl, $(C_0–C_2)$-alkylene-aryl, O—$(C_0–C_2)$-alkylene-aryl, COO—$(C_1–C_6)$-alkyl or $CO(R41)$;

R41 is $(C_1–C_6)$-alkyl or aryl;

A is a chain —$(C(R42)(R43))_m$- wherein 1 to 2 members are optionally replaced by an element selected from the group consisting of O, $N(R44)$ and CO;

m is 3 or 4;

R42, R43, R44 independently are H, $(C_1–C_6)$-alkyl or aryl;

R9, R10 independently are H, $(C_1–C_8)$-alkyl, $(CH_2)_o$—R45, $(C_1–C_4)$-alkoxy-$(C_1–C_4)$-alkyl, aryloxy-$(C_1–C_4)$-alkyl, $(C_3–C_8)$-alkenyl, $(C_3–C_8)$-alkynyl, CO—$(C_1–C_8)$-alkyl, —CO—$(CH_2)_o$—R45, or R9 and R10 form together with the nitrogen atom to which they are bonded a 4- to 10-membered mono-, bi- or spirocyclic ring wherein said ring, apart from the nitrogen atom, may optionally contain 0 to 2 additional heteroatoms selected from the group consisting of oxygen, nitrogen and sulfur, and wherein said ring optionally is substituted by F, Cl, Br, $CF_3$, CN, $(C_1–C_6)$-alkyl, O—$(C_1–C_8)$-alkyl, $(C_1–C_4)$-alkoxy-$(C_1–C_4)$-alkyl, $(C_0–C_2)$-alkylene-aryl, oxo, $CO(R46)$, $CON(R47)(R48)$, OH, $COO(R49)$, $N(R50)CO(C_1–C_6)$-alkyl, $N(R51)(R52)$ or $SO_2CH_3$;

R46, R47, R48, R49, R50, R51, R52 independently are H or $(C_1–C_6)$-alkyl;

o is 0, 1, 2, 3 or 4;

R45 is OH, a 3- to 12-membered mono- or bicyclic ring which optionally contains one or two heteroatoms selected from the group consisting of N, O and S, wherein the 3- to 12-membered ring optionally is substituted by F, Cl, Br, OH, $CF_3$, $NO_2$, CN, $OCF_3$, oxo, O—$(C_1–C_6)$-alkyl, $(C_1–C_6)$-alkyl, $(C_2–C_6)$-alkenyl, $(C_0–C_2)$-alkylene-aryl, O—$(C_0–C_2)$-alkylene-aryl, $N(R51)(R52)$, $SO_2$—$CH_3$ or COOH;

or the pharmaceutically acceptable salts thereof.

Particular preference is given to compounds of formula I in which

R is $(C_1–C_6)$-alkyl, $(C_3–C_8)$-cycloalkyl, or a 5- to 6-membered ring optionally containing one or two heteroatoms selected from the group consisting of N, O and S, wherein the 5- to 6-membered ring is optionally substituted by F, Cl, Br, $NO_2$, $CF_3$, $OCF_3$, CN, $(C_1–C_6)$-alkyl or O—$(C_1–C_6)$-alkyl;

B is a bond, O, S, CO, $OCH_2$, $N(R23)$ or $CH_2$;

R23 is H or $(C_1–C_6)$-alkyl;

R1, R2, R3, R4 independently are H, F, Cl, Br, $CF_3$, O—$(C_1–C_6)$-alkyl or $(C_1–C_6)$-alkyl;

W is —CH=CH— or —N=CH—;

R5, R6, R7, R8 independently are H, F, Cl, Br, OH, $CF_3$, $NO_2$, CN, $OCF_3$ or O—$(C_1–C_6)$-alkyl;

A is a chain —$(C(R42)(R43))_m$-, wherein one member of the chain is optionally replaced by an element selected from the group consisting of O and $N(R44)$;

m is 3 or 4;

R42, R43, R44 independently are H, $(C_1–C_6)$-alkyl or aryl;

R9, R10 independently are H, $(C_1–C_8)$-alkyl, —$(CH_2)_o$—R45, CO—$(C_1–C_8)$-alkyl, or R9 and R10 form together with the nitrogen atom to which they are bonded a 4- to 10-membered mono-, bi- or spirocyclic ring wherein said ring, apart from the nitrogen atom, may optionally contain 0 to 2 additional heteroatoms selected from the group consisting of O, N and S, wherein said ring optionally is substituted by F, $(C_1–C_6)$-alkyl, O—$(C_1–C_8)$-alkyl, oxo, $CO(R46)$, $CON(R47)(R48)$, OH, $N(R50)CO(C_1–C_6)$-alkyl or $N(R51)(R52)$;

R46, R47, R48, R50, R51, R52 independently are H or $(C_1–C_6)$-alkyl;

o is 0, 1, 2, 3 or 4;

R45 is OH, a 5- to 10-membered mono- or bicyclic ring which optionally contains one or two heteroatoms selected from the group consisting of N, O and S, wherein the 5- to 10-membered ring optionally is substituted by F, Cl, Br, OH, $CF_3$, oxo, O—$(C_1–C_6)$-alkyl, $(C_1–C_6)$-alkyl, $(C_0–C_2)$-alkylene-aryl, O—$(C_0–C_2)$-alkylene-aryl, or $N(R51)(R52)$;

A particular class within the particularly preferred compounds of formula I is formed by the molecules for which W is —CH=CH—.

A further particular class within the particularly preferred compounds of formula I is formed by the molecules for which m is 3;

R42, R43, R44 are H.

A further particular class within the particularly preferred compounds of formula I is formed by the molecules for which R5, R6, R7, R8 are H.

A further particular class within the particularly preferred compounds of formula I is formed by the molecules in which A and B are each disposed in the para position relative to the central W-containing heterocycle.

If radicals or substituents can occur more than once in the compounds of formula 1, such as, for example, —$(CH_2)_o$—R45, they may all, independently of one another, have the stated meanings and be identical or different.

The invention relates to compounds of formula I in the form of their racemates, enantiomer-enriched mixtures and pure enantiomers and to their diastereomers and mixtures thereof.

The alkyl, alkenyl and alkynyl radicals in the substituents R, R1, R2, R3, R4, R5, R6, R7, R8, R9, R10, R11, R12, R13, R14, R15, R16, R17, R18, R19, R20, R21, R22, R23, R24, R25, R26, R27, R28, R29, R30, R31, R32, R33, R34, R35, R36, R37, R38, R39, R40, R41, R42, R43, R44, R45, R46, R47, R48, R49, R50, R51 and R52 may be either straight-chain, branched or optionally halogenated.

DETAILED DESCRIPTION OF THE INVENTION

The term "aryl" means a phenyl or naphthyl group.

Mono-, bi- or spirocyclic rings may be saturated, partially saturated or unsaturated and also bridged.

Pharmaceutically acceptable salts are particularly suitable for medical applications because their solubility in water is higher than the initial or basic compounds. These salts must have a pharmaceutically acceptable anion or cation. Suitable pharmaceutically acceptable acid addition salts of the compounds of the formula I are salts of inorganic acids such as hydrochloric acid, hydrobromic acid, phosphoric, metaphosphoric, nitric, sulfonic and sulfuric acids, and organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric and trifluoroacetic acids. The chloride salt is particularly preferably used for medical purposes. Suitable pharmaceutically acceptable basic salts are ammonium salts, alkali metal salts (such as sodium and potassium salts) and alkaline earth metal salts (such as magnesium and calcium salts).

Salts with a pharmaceutically unacceptable anion likewise fall within the scope of the invention as useful intermediates for preparing or purifying pharmaceutically acceptable salts and/or for use in non-therapeutic, for example in vitro, applications.

The term "physiologically functional derivative" used herein refers to any physiologically tolerated derivative of a compound according to the invention of the formula I, for example an ester, which is able on administration to a mammal such as, for example, a human to form (directly or indirectly) a compound of the formula I or an active metabolite thereof.

The physiologically functional derivatives also include prodrugs of the compounds according to the invention. Such prodrugs can be metabolized in vivo to a compound according to the invention. These prodrugs may themselves be active or not.

The compounds according to the invention may also exist in various polymorphic forms, for example as amorphous and crystalline polymorphic forms. All polymorphic forms of the compounds according to the invention lie within the scope of the invention and are a further aspect of the invention.

All references hereinafter to "compound(s) of formula (I)" refer to compound(s) of the formula (I) as described above, and the salts, solvates and physiologically functional derivatives thereof as described herein.

The amount of a compound of formula (I) which is necessary to achieve the desired biological effect depends on a number of factors, for example the specific compound chosen, the intended use, the mode of administration and the clinical condition of the patient. In general, the daily dose is in the range from 0.3 mg to 100 mg (typically from 3 mg to 50 mg) per day and per kilogram of body weight, for example 3–10 mg/kg/day. An intravenous dose may be, for example, in the range from 0.3 mg to 1.0 mg/kg, which can most suitably be administered as infusion of from 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. It is thus possible for ampoules for injections to contain, for example, from 1 mg to 100 mg, and single-dose formulations which can be administered orally, such as, for example, tablets or capsules, to contain, for example, from 1.0 to 1000 mg, typically from 10 to 600 mg. In the case of pharmaceutically acceptable salts, the aforementioned weight data are based on the weight of the salt of the underlying free compound. For the prophylaxis or therapy of the abovementioned conditions, the compounds of formula (I) can be used as the compound itself, but they are preferably in the form of a pharmaceutical composition with an acceptable carrier. The carrier must, of course, be acceptable in the sense that it is compatible with the other ingredients of the composition and is not hazardous for the patient's health. The carrier may be a solid or a liquid or both and is preferably formulated with the compound as single dose, for example as tablet which may contain from 0.05% to 95% by weight of the active ingredient. Further pharmaceutically active substances may likewise be present, including other compounds of formula (I). The pharmaceutical compositions according to the invention can be produced by one of the known pharmaceutical methods which essentially consist of mixing the ingredients with pharmaceutically acceptable carriers and/or excipients.

Pharmaceutical compositions according to the invention are those suitable for oral, rectal, topical, peroral (for example sublingual) and parenteral (for example subcutaneous, intramuscular, intradermal or intravenous) administration although the most suitable mode of administration in each individual case depends on the nature and severity of the condition to be treated and on the nature of the compound of formula (I) used in each case. Coated formulations and coated slow-release formulations also lie within the scope of the invention. Formulations resistant to acid and gastric fluid are preferred. Suitable coatings resistant to gastric fluid comprise cellulose acetate phthalate, polyvinyl acetate phthalate, hydroxypropylmethylcellulose phthalate and anionic polymers of methacrylic acid and methyl methacrylate.

Suitable pharmaceutical compositions for oral administration may be in the form of separate units such as, for example, capsules, cachets, suckable tablets or tablets, each of which contain a defined amount of the compound of formula (I); as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. In general, the compositions are produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form, such as, for example, a powder or granules, where appropriate mixed with a binder, lubricant, inert diluent and/or a (plurality of) surface-active/dispersing agent(s) in a suitable machine. Molded tablets can be produced by molding the compound which is in powder form and is moistened with an inert liquid diluent in a suitable machine.

Pharmaceutical compositions suitable for peroral (sublingual) administration comprise suckable tablets which contain a compound of formula (I) with a flavoring, normally sucrose and gum arabic or tragacanth, and pastilles which comprise the compound in an inert base such as gelatin and glycerol or sucrose and gum arabic.

Suitable pharmaceutical compositions for parenteral administration comprise preferably sterile aqueous preparations of a compound of formula (I), which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions according to the invention generally contain from 0.1 to 5% by weight of the active compound.

Suitable pharmaceutical compositions for rectal administration are preferably in the form of single-dose suppositories. These can be produced by mixing a compound of formula (I) with one or more conventional solid carriers, for example cocoa butter, and shaping the resulting mixture.

Suitable pharmaceutical compositions for topical application to the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Suitable pharmaceutical compositions for transdermal uses can be in the form of single plasters which are suitable for long-term close contact with the patient's epidermis. Such plasters suitably contain the active ingredient in an optionally buffered aqueous solution, dissolved and/or dispersed in an adhesive or dispersed in a polymer. A suitable active ingredient concentration is about 1% to 35%, preferably about 3% to 15%. As a special possibility, the active ingredient can be released as described, for example, in Pharmaceutical Research, 2(6): 318 (1986) by electrotransport or iontophoresis.

The compounds of the formula I are distinguished by beneficial effects on lipid metabolism, and they are particularly suitable for weight reduction and for maintaining a reduced weight after weight reduction has taken place in mammals and as anorectic agents. The compounds are distinguished by their low toxicity and their few side effects.

The compounds can be employed alone or in combination with other weight-reducing or anorectic active ingredients. Further anorectic active ingredients of this type are mentioned, for example, in the Roten Liste, chapter 01 under weight-reducing agents/appetite suppressants, and may also include active ingredients which increase the energy turnover of the organism and thus lead to weight reduction or else those which influence the general metabolism of the organism in such a way that an increased calorie intake does not lead to an enlargement of the fat depots and a normal calorie intake leads to a reduction of the fat depots of the organism. The compounds are suitable for the prophylaxis and, in particular, for the treatment of excessive weight or obesity. The compounds are further suitable for the prophylaxis and, in particular, for the treatment of type II diabetes, of arteriosclerosis and for normalizing lipid metabolism and for the treatment of high blood pressure. The compounds act as MCH antagonists and are also suitable for the treatment of disturbances of wellbeing and other psychiatric indications such as, for example, depressions, anxiety states, anxiety neuroses, schizophrenia and for the treatment of disorders associated with the circadian rhythm and for the treatment of drug abuse.

In a further aspect of the invention, the compounds of the formula I can be administered in combination with one or more other pharmacologically active substances which are selected, for example, from antidiabetics, antiobesity agents, active ingredients which lower blood pressure, lipid-lowering agents and active ingredients for the treatment and/or prevention of complications caused by diabetes or associated with diabetes. Suitable antidiabetics include insulins, amylin, derivatives of GLP-1 and GLP-2 such as, for example, those disclosed in WO 98/08871 of Novo Nordisk A/S, and orally active hypoglycemic active ingredients.

The orally active hypoglycemic active ingredients preferably comprise sulfonylureas, biguanidines, meglitinides, oxadiazolidinediones, thiazolidinediones, glucosidase inhibitors, glucagon receptor antagonists, GLP-1 agonists, potassium channel openers such as, for example, those disclosed in WO 97/26265 and WO 99/03861 of Novo Nordisk A/S, insulin sensitizers, activators of insulin receptor kinase, inhibitors of liver enzymes involved in the stimulation of gluconeogenesis and/or glycogenolysis, for example inhibitors of glycogen phosphorylase, modulators of glucose uptake and glucose excretion, compounds which alter lipid metabolism, such as antihyperlipidemic active ingredients and antilipidemic active ingredients, for example HMGCoA reductase inhibitors, inhibitors of cholesterol transport/of cholesterol uptake, inhibitors of bile acid reabsorption or inhibitors of the microsomal triglyceride transfer protein (MTP), compounds which reduce food intake, PPAR and RXR agonists and active ingredients which act on the ATP-dependent potassium channel of the beta cells.

In one embodiment of the invention, the present compounds are administered in combination with insulin.

In a further embodiment, the present compounds are administered in combination with a sulfonylurea such as, for example, tolbutamide, glibenclamide, glimepiride, glipizide, gliquidone, glisoxepide, glibornuride or gliclazide.

In another embodiment, the present compounds are administered in combination with a biguanide such as, for example, metformin.

In yet another embodiment, the present compounds are administered in combination with a meglitinide such as, for example, repaglinide. In yet a further embodiment, the present compounds are administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In a further embodiment, the present compounds are administered in combination with an (α-glucosidase inhibitor such as, for example, miglitol or acarbose.

In another embodiment, the present compounds are administered in combination with an active ingredient which acts on the ATP-dependent potassium channel of the beta cells, such as, for example, tolbutamide, glibenclamide, glimepiride, glipizide, gliclazide or repaglinide.

In yet another embodiment, the present compounds are administered in combination with an antihyperlipidemic active ingredient or an antilipidemic active ingredient such as, for example, cholestyramine, colestipol, clofibrate, fenofibrate, gemfibrozil, lovastatin, pravastatin, simvastatin, atorvastatin, cerivastatin, fluvastatin, probucol, ezetimibe or dextrothyroxine.

In a further embodiment, the present compounds are administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

The compounds of the invention may additionally be administered in combination with one or more antiobesity agents or appetite-regulating active ingredients.

Active ingredients of these types may be selected from the group consisting of CART agonists, NPY antagonists, MC4 agonists, orexin antagonists, H3 agonists, TNF agonists, CRF agonists, CRF BP antagonists, urocortin agonists, β3 agonists, MSH (melanocyte-stimulating hormone) agonists, CCK agonists, serotonin-reuptake inhibitors, mixed serotonin- and noradrenaline-reuptake inhibitors, 5HT modulators, MAO inhibitors, bombesin agonists, galanin antagonists, growth hormone, growth hormone-releasing compounds, TRH agonists, modulators of uncoupling proteins 2 or 3, leptin agonists, dopamine agonists (bromocriptine, Doprexin), lipase/amylase inhibitors, antagonists of cannabinoid receptor 1, modulators of acylation-stimulating protein (ASP), PPAR modulators, RXR modulators, hCNTF agonists or TR-β agonists.

In one embodiment of the invention, the antiobesity agent is leptin or modified leptin.

In another embodiment, the antiobesity agent is dexamphetamine or amphetamine.

In another embodiment, the antiobesity agent is fenfluramine or dexfenfluramine.

In yet another embodiment, the antiobesity agent is sibutramine or the mono- and bisdemethylated active metabolites of sibutramine.

In a further embodiment, the antiobesity agent is orlistat.

In another embodiment, the antiobesity agent is mazindol, diethylpropion or phentermine.

The present compounds may additionally be administered in combination with one or more antihypertensive active ingredients. Examples of antihypertensive active ingredients are beta blockers such as alprenolol, atenol, timolol, pindolol, propanolol and metoprolol, ACE (angiotensin converting enzyme) inhibitors such as, for example, benazepril, captopril, enalapril, fosinopril, lisinopril, quinapril and rampril, calcium channel blockers such as nifedipine, felodipine, nicardipine, isradipine, nimodipine, diltiazem and verapamil, and alpha blockers such as doxazosin, urapidil, prazosin and terazosin. Reference may furthermore be made to Remington: The Science and Practice of Pharmacy, 19th edition, Gennaro, editor, Mack Publishing Co., Easton, Pa., 1995.

It will be appreciated that every suitable combination of the compounds of the invention with one or more of the aforementioned compounds and optionally one or more other pharmacologically active substances is to be regarded as covered by the scope of protection of the present invention.

EXPERIMENTAL

In two articles which appeared simultaneously in Nature (Nature 400, 261–264, 1999; Nature 400, 265–269, 1999, see annex), two research groups separately described a highly specific receptor for the melanin-concentrating hormone (MCH). MCH undertakes important functions in the control of food intake. Compounds which act on the MCH receptor therefore have an anorectic effect and are suitable for the treatment of obesity. The anorectic effect of the compounds of the invention of the formula I was therefore tested as follows.

Functional measurements to establish IC50 values

The cloning of the cDNA for the human MCH receptor, production of the recombinant HEK293 cell line which expresses the human MCH receptor, and functional measurements using the recombinant cell line took place in analogy to the description by Audinot et al. (J. Biol. Chem. 276, 13554–13562, 2001). However, a difference from the reference was that the plasmid pEAK8 from EDGE Biosystems (USA) was used for constructing the expression vector. The host used for the transfection was a transformed HEK cell line named "PEAK Stable Cells" (likewise from EDGE Biosystems). The functional measurements of the cellular calcium flux after addition of agonist (MCH) in the presence of ligand of the invention took place with the aid of the FLIPR apparatus from Molecular Devices (USA), using protocols of the manufacturer of the apparatus. The exemplary compounds showed IC50 values in the order of magnitude from 0.01 to >10 μM.

The efficacy of the compounds was additionally tested as follows:

Biological Test Model:

The anorectic effect was tested on female NMRI mice. After withdrawal of food for 17 hours, the test compound was administered by gavage. The animals were housed singly with free access to drinking water and were offered condensed milk 30 minutes after administration of the compound. Condensed milk consumption was determined every half hour for 7 hours, and the general wellbeing of the animals was observed. The measured milk consumption was compared with the vehicle-treated control animals.

Table 1: Anorectic effect measured as the reduction in the cumulative milk consumption of treated compared with control animals.

TABLE 1

Anorectic effect measured as the reduction in the cumulative milk consumption of treated compared with control animals.

| Example | Oral dose [mg/kg] | Number of animals/ cumulative milk consumption of the treated animals N/[ml] | Number of animals/ cumulative milk consumption of the control animals N/[ml] | Reduction in the cumulative milk consumption as % of the control |
|---|---|---|---|---|
| Example 1 | 30 | 5/1.7 | 5/4.1 | 58 |

The examples and preparation methods detailed below serve to illustrate the invention without, however, restricting it.

EXAMPLE 1

1-[4-(2-Dimethylaminoethoxy)phenyl]-3-(4-phenoxyphenyl)-1,3-dihydroimidazol-2-one

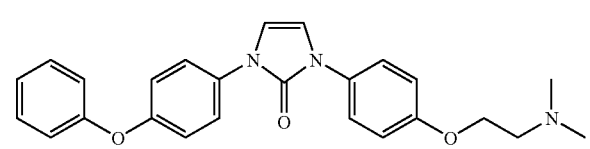

1-(2,2-Dimethoxyethyl)-3-[4-(2-dimethylaminoethoxy)phenyl]-1-(4-phenoxy-phenyl)urea (0.33 g) was shaken with trifluoroacetic acid (5 ml) for 16 hours. Volatiles were removed and the residue was taken up in dichloromethane (10 ml) and washed with sodium hydroxide solution (0.1N; 1 ml). The aqueous phase was extracted with dichloromethane (10 ml), and the combined organic phases were concentrated. The residue was purified by chromatography on silica gel (eluent: dichloromethane/methanol 98:2 with 1% v/v 7N ammonia solution in methanol). The product with the molecular weight of 415.50 ($C_{25}H_{25}N_3O_3$); MS (ESI): 416 ([M+H]$^+$), was obtained in this way.

1-(2,2-Dimethoxyethyl)-3-[4-(2-dimethylaminoethoxy)phenyl]-1-(4-phenoxy-phenyl)urea A solution of triphosgene (178 mg) in chloroform (1 ml) was added to a solution of 4-(2-dimethylaminoethoxy) aniline (324 mg) in chloroform (2 ml) and pyridine (0.182 ml) at 0° C. under nitrogen. The reaction was then shaken at room temperature for 30 minutes. The solution was then added to a solution of (2,2-dimethoxyethyl)-(4-phenoxyphenyl)amine (410 mg) in chloroform (2 ml) and pyridine (0.182 ml) and shaken at 70° C. for 3 hours. Water (1 ml) was added. The mixture was extracted with dichloromethane (2×15 ml). The combined organic phases were concentrated and the residue was purified by chromatography on silica gel (eluent: dichloromethane/methanol 98:2 with 1% v/v 7N ammonia solution in methanol). The product with the molecular weight of 479.58 ($C_{27}H_{33}N_3O_5$); MS (ESI): 442 ([M-OMe]$^+$), was obtained in this way.

(2,2-Dimethoxyethyl)-(4-phenoxyphenyl)amine

A solution of 4-phenoxyaniline (915 mg) in dimethylformamide (5 ml) was mixed with bromoacetaldehyde dimethyl acetal (1.1 ml) and BEMP (1.9 ml). The reaction mixture was shaken at 100° C. for 16 hours. Volatiles were removed and the residue was purified by chromatography on silica gel (eluent: dichloromethane/hexane 1:2, later 1:1 with in each case 1% v/v 7N ammonia solution in methanol). The product with the molecular weight of 273.33 ($C_{16}H_{19}NO_3$); MS (ESI): 274 ([M+H]$^+$), was obtained in this way.

EXAMPLE 2

1-[4-(2-Dimethylaminoethylamino)-3-nitrophenyl]-3-(4-phenoxyphenyl)-1,3-dihydroimidazol-2-one

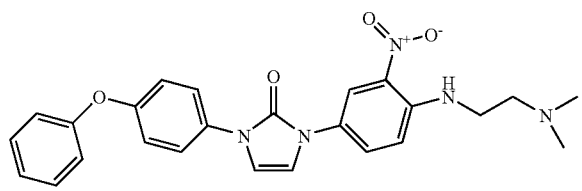

A solution of 1-(4-fluoro-3-nitrophenyl)-3-(4-phenoxyphenyl)-1,3-dihydroimidazol-2-one (100 mg) in dimethylformamide (2 ml) was shaken with 2-dimethylaminoethylamine (0.3 ml) at 70° C. for 2 hours. Volatiles were removed and the residue was partitioned between dichloromethane and water. The organic phase was dried and concentrated. The product with the molecular weight of 459.51 ($C_{25}H_{25}N_5O_4$); MS (ESI): 460 ([M+H]$^+$), was obtained in this way.

1-(4-Fluoro-3-nitrophenyl)-3-(4-phenoxyphenyl)-1,3-dihydroimidazol-2-one

4-Fluoro-3-nitrophenyl isocyanate (0.45 ml) was added to a solution of (2,2-dimethoxyethyl)-(4-phenoxyphenyl)amine (750 mg) in chloroform (10 ml). The reaction was shaken at 70° C. for 2 hours. A second portion of 4-fluoro-3-nitrophenyl isocyanate (0.45 ml) was added. After 16 hours at 70° C., volatiles were removed and TFA.(10 ml) was added. After shaking for 16 hours, volatiles were removed and the residue was purified by chromatography on silica gel (eluent: dichloromethane/hexane 8:1). The product with the molecular weight of 391.36 ($C_{21}H_{14}FN_3O_4$); MS (ESI): 392 ([M+H]$^+$), was obtained in this way.

EXAMPLE 3

1-[3-Amino-4-(2-dimethylaminoethylamino)phenyl]-3-(4-phenoxyphenyl)-1,3-dihydroimidazol-2-one

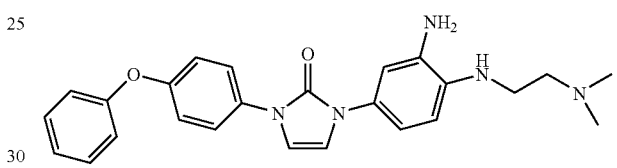

Zinc dust (250 mg) was added to a solution of 1-[4-(2-dimethylamino-ethylamino)-3-nitrophenyl]-3-(4-phenoxyphenyl)-1,3-dihydroimidazol-2-one (50 mg) in dichloromethane (10 ml) and glacial acetic acid (1 ml). After 10 minutes, solids were removed by filtration and the filtrate was washed with saturated sodium carbonate solution. The organic phase was dried over magnesium sulfate and concentrated. The product with the molecular weight of 429.53 ($C_{25}H_{27}N_5O_2$); MS (ESI): 430 ([M+H]$^+$), was obtained in this way.

EXAMPLE 4

1-[3-Benzyl-4-(2-pyrrolidin-1-ylethoxy)phenyl]-3-(4-phenoxyphenyl)-1,3-dihydroimidazol-2-one

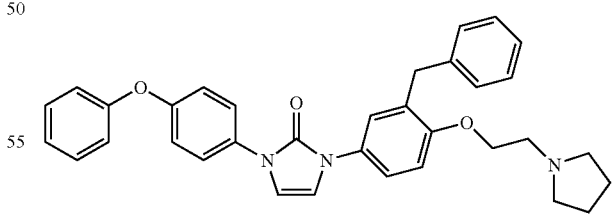

A solution of 1-[3-benzyl-4-(2-bromoethoxy)phenyl]-3-(4-phenoxyphenyl)-1,3-dihydroimidazol-2-one (60 mg) in acetonitrile (1 ml) was mixed with pyrrolidine (0.2 ml) and sodium iodide (5 mg) and boiled under reflux for 2 hours. The cooled solution was filtered and concentrated. The residue was purified by preparative HPLC. The product with the molecular weight of 531.66 ($C_{34}H_{33}N_3O_3$); MS (ESI): 532 ([M+H]$^+$), was obtained as hydroformate in this way.

1-[3-Benzyl-4-(2-bromoethoxy)phenyl]-3-(4-phenoxyphenyl)-1,3-dihydroimidazol-2-one A solution of 1-(3-benzyl-4-hydroxyphenyl)-3-(4-phenoxyphenyl)-1,3-dihydroimidazol-2-one (233 mg) in 1,2-dibromoethane (1.7 ml) was mixed with sodium hydroxide solution (3N, 0.6 ml) and tetrabutylammonium hydrogen sulfate (12 mg). The mixture was heated at 80° C. for 2 hours. After cooling, the reaction mixture was diluted with dichloromethane and washed with sodium hydroxide solution (1N), hydrochloric acid (1N) and saturated brine. The organic phase was dried over magnesium sulfate and concentrated, and the residue was purified by chromatography on silica gel (eluent: heptane/ethyl acetate 3:2). The product with the molecular weight of 541.45 ($C_{30}H_{25}BrN_2O_3$); MS (ESI): 541 ([M+H]$^+$), was obtained in this way.

1-(3-Benzyl-4-hydroxyphenyl)-3-(4-phenoxyphenyl)-1,3-dihydroimidazol-2-one

A solution of 3-(4-benzyloxyphenyl)-1-(2,2-dimethoxyethyl)-1-(4-phenoxy-phenyl)urea (498 mg) in trifluoroacetic acid (5 ml) was left to stand for 3 days and then neutralized with saturated sodium carbonate solution. The mixture was extracted with ethyl acetate. The organic phase was dried over magnesium sulfate and concentrated, and the residue was purified by chromatography on silica gel (eluent: dichloromethane/methanol 9:1). The product with the molecular weight of 434.50 ($C_{28}H_{22}N_2O_3$); MS (ESI): 435 ([M+H]$^+$), was obtained in this way. 1-(4-Hydroxyphenyl)-3-(4-phenoxy-phenyl)-1,3-dihydroimidazol-2-one was obtained as a further product.

3-(4-Benzyloxyphenyl)-1-(2,2-dimethoxyethyl)-1-(4-phenoxyphenyl)urea

A solution of 4-benzyloxyaniline (199 mg) in dimethylformamide (1 ml) was added dropwise to a solution of carbonyldiimidazole (162 mg) in dimethylformamide (1 ml) at 0° C. After a reaction time at 0° C. of 10 minutes, the reaction was allowed to continue at room temperature for 20 minutes. Then (2,2-dimethoxyethyl)-(4-phenoxyphenyl)amine (273 mg) was added, and the mixture was heated at 80° C. for 1.5 hours. Cooling was followed by dilution with water and extraction with ethyl acetate. The organic phase was dried over magnesium sulfate and concentrated. The product with the molecular weight of 498.58 ($C_{30}H_{30}N_2O_5$); MS (ESI): 499 ([M+H]$^+$), was obtained in this way.

EXAMPLE 5

1-[4-(2-Phenethylaminoethoxy)phenyl]-3-(4-phenoxyphenyl)-1,3-dihydroimidazol-2-one A solution of 1-[4-(2-bromoethoxy)phenyl]-3-(4-phenoxyphenyl)-1,3-dihydroimidazol-2-one (50 mg) in acetonitrile (1 ml) was mixed with phenethylamine (47 mg), potassium carbonate (70 mg) and sodium iodide (5 mg) and boiled under reflux for 2 hours. The cooled solution was filtered and concentrated. The residue was purified by preparative HPLC. The product with the molecular weight of 491.60 ($C_{31}H_{29}N_3O_3$); MS (ESI): 492 ([M+H]$^+$), was obtained as hydroformate in this way.

1-[4-(2-Bromoethoxy)phenyl]-3-(4-phenoxyphenyl)-1,3-dihydroimidazol-2-one

A solution of 1-(4-hydroxyphenyl)-3-(4-phenoxyphenyl)-1,3-dihydroimidazol-2-one (4.7 g) in 1,2-dibromoethane (23.6 ml) was mixed with sodium hydroxide solution (3N, 9.1 ml) and tetrabutylammonium hydrogen sulfate (232 mg). The mixture was heated at 75° C. for 2 hours. After cooling, the reaction mixture was mixed with dichloromethane and washed with sodium hydroxide solution (1N), hydrochloric acid (1N) and saturated brine. The organic phase was dried over magnesium sulfate and concentrated, and the residue was purified by chromatography on silica gel (eluent: dichloromethane/methanol 9:1). The product with the molecular weight of 451.32 ($C_{23}H_{19}BrN_2O_3$); MS (ESI): 451 ([M+H]$^+$), was obtained in this way.

1-(4-Hydroxyphenyl)-3-(4-phenoxyphenyl)-1,3-dihydroimidazol-2-one

Boron tribromide (2.5 ml) was added to a solution of 1-(4-methoxyphenyl)-3-(4-phenoxyphenyl)-1,3-dihydroimidazol-2-one (6.0 g) in dichloromethane (75 ml) at 0° C. After 3 hours, saturated sodium bicarbonate solution was added and the organic phase was washed with saturated brine. The organic phase was dried over magnesium sulfate and concentrated, and the residue was purified by chromatography on silica gel (eluent: dichloromethane/methanol 9:1). The product with the molecular weight of 344.37 ($C_{21}H_{16}N_2O_3$); MS (ESI): 345 ([M+H]$^+$), was obtained in this way.

1-(4-Methoxyphenyl)-3-(4-phenoxyphenyl)-1,3-dihydroimidazol-2-one

A solution of 1-(2,2-dimethoxyethyl)-3-(4-methoxyphenyl)-1-(4-phenoxy-phenyl)urea (6.8 g) in trifluoroacetic acid (20 ml) was left to stand for 16 hours and then neutralized with saturated sodium carbonate solution. The mixture was extracted with ethyl acetate. The organic phase was dried over magnesium sulfate and concentrated. The product with the molecular weight of 358.40 ($C_{22}H_{18}N_2O_3$); MS (ESI): 359 ([M+H]$^+$), was obtained in this way.

1-(2,2-Dimethoxyethyl)-3-(4-methoxyphenyl)-1-(4-phenoxyphenyl)urea

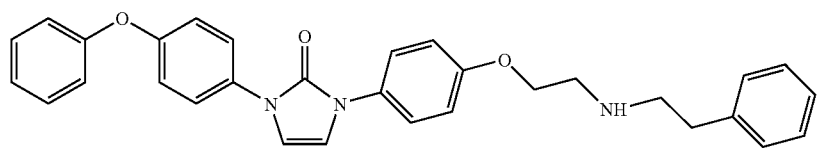

A solution of 4-methoxyaniline (1.9 g) in dimethylformamide (3 ml) was added dropwise to a solution of carbonyldiimidazole (2.51 g) in dimethylformamide (15 ml) at 0° C.

After a reaction time at 0° C. of 15 minutes, the reaction was allowed to continue at room temperature for 45 minutes. Then (2,2-dimethoxyethyl)-(4-phenoxyphenyl)amine (4.1 g) in dimethylformamide (2 ml) was added, and the mixture was heated at 80° C. for 2 hours. After cooling, volatiles were removed and the residue was taken up in ethyl acetate. The organic phase was washed with water and saturated brine. The organic phase was dried over magnesium sulfate and concentrated. The product with the molecular weight of 422.49 ($C_{24}H_{26}N_2O_5$); MS (ESI): 423 ([M+H]$^+$), was obtained in this way.

EXAMPLE 6

1-[4-(2-Methylaminoethoxy)phenyl]-3-(4-phenoxyphenyl)-1,3-dihydroimidazol-2-one

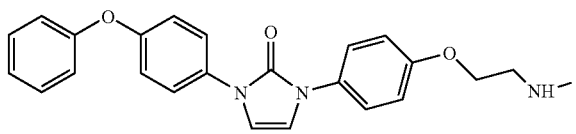

A solution of 1-[4-(2-bromoethoxy)phenyl]-3-(4-phenoxyphenyl)-1,3-dihydroimidazol-2-one (50 mg) in acetonitrile (1 ml) was left to stand with methylamine (1M in THF, 1 ml) and sodium iodide (5 mg) and 24 hours. The reaction solution was filtered and concentrated. The residue was purified by preparative HPLC. The product with the molecular weight of 401.47 ($C_{24}H_{23}N_3O_3$); MS (ESI): 402 ([M+H]$^+$), was obtained as hydroformate in this way.

EXAMPLE 7

1-[4-(2-Aminoethoxy)phenyl]-3-(4-phenoxyphenyl)-1,3-dihydroimidazol-2-one

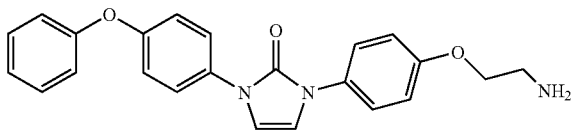

A solution of 1-[4-(2-bromoethoxy)phenyl]-3-(4-phenoxyphenyl)-1,3-dihydroimidazol-2-one (50 mg) in acetonitrile (1 ml) was left to stand with ammonia solution (1 ml) and sodium iodide (5 mg) and 24 hours. After repeated addition of the ammonia solution, the reaction was kept at 40° C. for 5 hours. The cooled reaction solution was filtered and concentrated. The residue was purified by preparative HPLC. The product with the molecular weight of 387.44 ($C_{24}H_{21}N_3O_3$); MS (ESI): 388 ([M+H]$^+$), was obtained as hydroformate in this way.

EXAMPLE 8

1-(4-Cyclopentyloxyphenyl)-3-[4-(3-dimethylaminopropoxy)phenyl]-1,3-dihydroimidazol-2-one

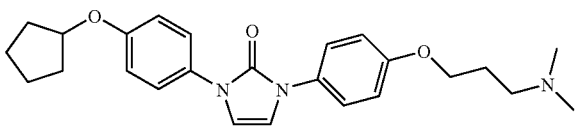

Carbonyldiimidazole (163 mg) was added to a solution of 4-(3-dimethyl-aminopropoxy)phenylamine (194 mg) in dimethylformamide (5 ml) at 0° C. After 10 minutes at 0° C. and 30 minutes at room temperature, a solution of (4-cyclopentyloxyphenyl)-(2,2-dimethoxyethyl)amine (265 mg) in dimethyl-formamide (1 ml) was added, and the mixture was heated at 80° C. for 2 hours. After cooling to room temperature, trifluoroacetic acid (1 ml) was added. After 72 hours, the mixture was diluted with water and extracted with ethyl acetate. The organic phase was washed with saturated sodium bicarbonate solution, dried and concentrated. The residue was purified by preparative HPLC. The product with the molecular weight of 421.54 ($C_{25}H_{31}N_3O_3$); MS (ESI): 422 ([M+H]$^+$), was obtained as hydrotrifluoro-acetate in this way.

4-(3-Dimethylaminopropoxy)phenylamine

Palladium(II) hydroxide (20% on carbon; 0.4 g) was added to a solution of dimethyl-[3-(4-nitrophenoxy)propyl]amine (3.75 g) in ethanol (75 ml) under argon. Then formic acid (4 ml) was added dropwise, during which the reaction mixture heated to 60° C. while evolving much gas. After a reaction time of 90 minutes, the catalyst was filtered off and the filtrate was concentrated. The residue was partitioned between methyl tert-butyl ether and sodium hydroxide solution (2N). The organic phase was dried and concentrated. The product with the molecular weight of 194.28 ($C_{11}H_{18}N_2O$); MS (ESI):195 ([M+H]$^+$), was obtained in this way.

Dimethyl-[3-(4-nitrophenoxy)propyl]amine

A mixture of 4-fluoronitrobenzene (2.82 g), 3-dimethylaminopropanol (2.48 g), powdered potassium hydroxide (1.35 g) and Aliquat® 336 (tricaprylylmethylammonium chloride) was heated at 85° C. for one hour. The cooled crude mixture was purified by chromatography on silica gel (eluent: ethyl acetate/methanol 9:1 mixed with 1% v/v triethylamine). The product with the molecular weight of 224.26 ($C_{11}H_{16}N_2O_3$); MS (ESI): 225 ([M+H]$^+$), was obtained in this way.

(4-Cyclopentyloxyphenyl)-(2,2-dimethoxyethyl)amine

A suspension of 4-cyclopentyloxyphenylamine (8.86 g), bromo-acetaldehyde dimethyl acetal (12.2 g), potassium carbonate (13.8 g) and dimethylformamide (100 ml) was heated at 100° C. for 5 hours. Cooling was followed by filtration and concentration of the filtrate. The residue was purified by chromatography on silica gel (eluent: heptane/ethyl acetate 4:1). The product with the molecular weight of 265.36 ($C_{15}H_{23}NO_3$); MS (ESI): 266 ([M+H]$^+$), was obtained in this way.

4-Cyclopentyloxyphenylamine

Sodium hydride (50% in oil; 4.8 g) was added in portions to a solution of 4-aminophenol (10.9 g) in dimethylformamide (150 ml). After 20 minutes, cyclopentyl bromide (14.9 g) was added dropwise. After 2 hours at room temperature, the reaction mixture was diluted with water and extracted with ethyl acetate. The organic phase was washed with water and brine, dried and concentrated. The residue was purified by chromatography on silica gel (eluent: heptane/ethyl acetate 3:1). The product with the molecular weight of 177.25 ($C_{11}H_{15}NO$); MS (ESI): 178 ([M+H]$^+$), was obtained in this way.

EXAMPLE 9

1-(4-Cyclopentyloxyphenyl)-3-[4-((1 R,2S)-2-dimethylamino-1-phenylpropoxy)-phenyl]-1,3-dihydroimidazol-2-one

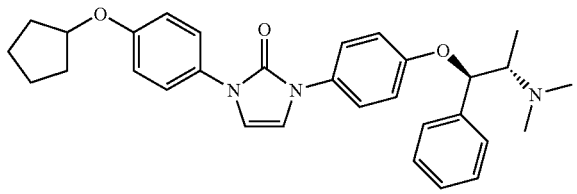

The compound was prepared as described in example 8 but with use of 4-((1R,2S)-2-dimethylamino-1-phenylpropoxy)phenylamine. The product with the molecular weight of 497.64 ($C_{31}H_{35}N_3O_3$); MS (ESI): 498 ([M+H]$^+$), was obtained as hydrotrifluoroacetate in this way.

4-((1R,2S)-2-Dimethylamino-1-phenylpropoxy)phenylamine

The compound was prepared as described in example 8 but with use of (1R,2S)-dimethyl-[1-methyl-2-(4-nitrophenoxy)-2-phenylethyl]amine. The product with the molecular weight of 270.38 ($C_{17}H_{22}N_2O$); MS (ESI): 271 ([M+H]$^+$), was obtained in this way.

(1R,2S)-Dimethyl-[1-methyl-2-(4-nitrophenoxy)-2-phenylethyl]amine

The compound was prepared as described in example 8 but with use of (1R,2S)-dimethyl-[1-methyl-2-hydroxy)-2-phenylethyl]amine. The product with the molecular weight of 300.36 ($C_{17}H_{20}N_2O_3$); MS (ESI): 301 ([M+H]$^+$), was obtained in this way.

EXAMPLE 10

1-(4-Cyclopentyloxyphenyl)-3-{4-[(2-dimethylaminoethyl)methylamino]-phenyl}-1,3-dihydroimidazol-2-one

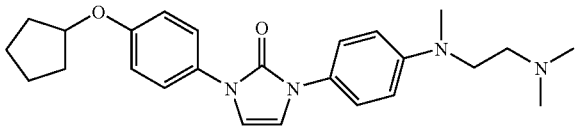

The compound was prepared as described in example 8 but with use of N-(2-dimethylaminoethyl)-N-methylbenzene-1,4-diamine. The product with the molecular weight of 420.56 ($C_{25}H_{32}N_4O_2$); MS (ESI): 421 ([M+H]$^+$), was obtained as hydrotrifluoroacetate in this way.

N-(2-Dimethylaminoethyl)-N-methylbenzene-1,4-diamine

The compound was prepared by zinc dust reduction of N,N,N'-trimethyl-N'-(4-nitrophenyl)ethane-1,2-diamine in analogy to the method in example 3. The product with the molecular weight of 193.29 ($C_{11}H_{19}N_3$); MS (ESI): 194 ([M+H]$^+$), was obtained in this way.

N,N,N'-Trimethyl-N'-(4-nitrophenyl)ethane-1,2-diamine

A mixture of N,N,N'-trimethylethane-1,2-diamine (2.17 g), potassium carbonate (3.0 g), 4-nitrofluorobenzene and dimethylformamide (30 ml) was stirred for 72 hours. The reaction mixture was diluted with water and extracted with ethyl acetate. The organic phase was washed with water and saturated brine, dried and concentrated. The product with the molecular weight of 223.28 ($C_{11}H_{17}N_3O_2$); MS (ESI): 224 ([M+H]$^+$), was obtained in this way.

EXAMPLE 11

1-(4-Cyclopentyloxyphenyl)-3-[4-(3-dimethylaminopropyl)phenyl]-1,3-dihydroimidazol-2-one

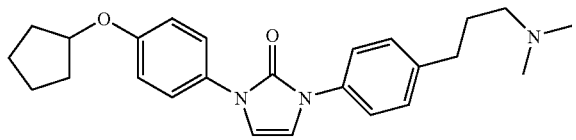

The compound was prepared as described in example 8 but with use of 4-(3-dimethylaminopropyl)phenylamine. The product with the molecular weight of 405.54 ($C_{25}H_{31}N_3O_2$); MS (ESI): 406 ([M+H]$^+$), was obtained as hydrotrifluoroacetate in this way.

4-(3-Dimethylaminopropyl)phenylamine

A solution of 3-dimethylamino-1-(4-nitrophenyl)propan-1-one (hydrochloride, 0.25 g) in glacial acetic acid (10 ml) was adjusted to pH 1 with concentrated hydrochloric acid and, under nitrogen, palladium(II) hydroxide (20% on carbon, 0.1 g) was added. The nitrogen atmosphere was replaced by hydrogen, and the suspension was shaken for 6 hours. The catalyst was filtered off and the filtrate was concentrated. The residue was partitioned between saturated sodium bicarbonate solution and ethyl acetate. The aqueous phase was adjusted to pH>12 with sodium hydroxide solution and extracted with ethyl acetate. The combined organic phases were dried and concentrated. The product with the molecular weight of 178.28 ($C_{11}H_{18}N_2$); MS (ESI): 179 ([M+H]$^+$), was obtained in this way.

3-Dimethylamino-1-(4-nitrophenyl)propan-1-one

A mixture of 4-nitroacetophenone (1.0 g), N,N-dimethylmethylene-ammonium chloride (0.56 g) and acetonitrile (10 ml) was heated at 80° C. for 4 hours, and the precipitate which separated out after cooling was filtered off with suction. The product with the molecular weight of 222.25 ($C_{11}H_{14}N_2O_3$); MS (ESI): 223 ([M+H]$^+$), was obtained as hydrochloride in this way.

EXAMPLES 12–91

Further examples which were prepared as described in example 5 but with use of the appropriate amine are summarized in table 2

TABLE 2

| Ex. No. | Name | Structure | Molecular formula | Molecular weight | [M + H]+ ESI-MS |
|---|---|---|---|---|---|
| 12 | 1-{4-[2-(2-Methoxyethylamino)ethoxy]phenyl}-3-(4-phenoxyphenyl)-1,3-dihydroimidazol-2-one | 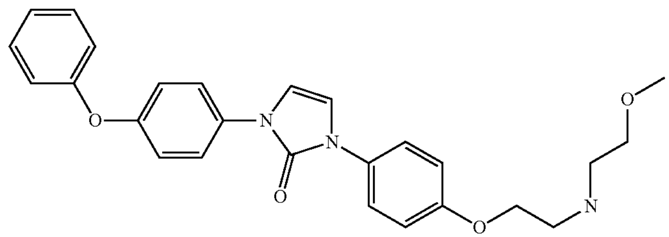 | C26H27N3O4 | 445.52 | 446 |
| 13 | 1-(4-Phenoxyphenyl)-3-{4-[2-((1S,5R)-1,3,3-trimethyl-6-azabicyclo[3.2.1]oct-6-yl)ethoxy]phenyl}-1,3-dihydroimidazol-2-one | 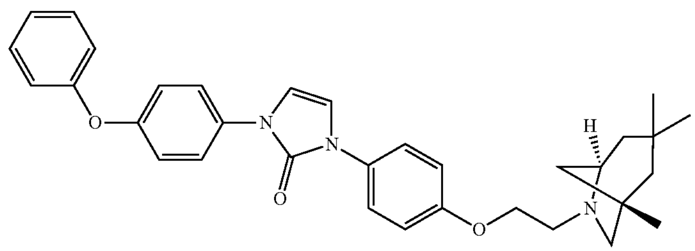 | C33H37N3O3 | 523.68 | 524 |
| 14 | 1-(4-Phenoxyphenyl)-3-[4-(2-thiomorpholin-4-ylethoxy)phenyl]-1,3-dihydroimidazol-2-one | 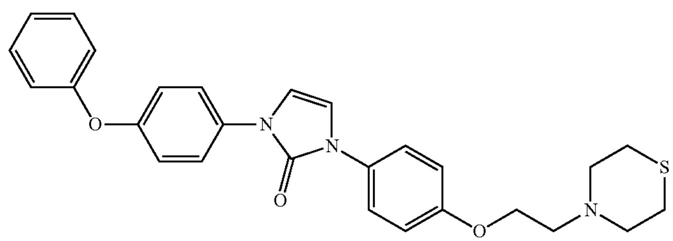 | C27H27N3O3S | 473.60 | 474 |

TABLE 2-continued

| Ex. No. | Name | Structure | Molecular formula | Molecular weight | [M + H]+ ESI-MS |
|---|---|---|---|---|---|
| 15 | 1-(2-{4-[2-Oxo-3-(4-phenoxyphenyl)-2,3-dihydroimidazol-1-yl]phenoxy}ethyl)piperidine-3-carboxylic acid diethylamide | 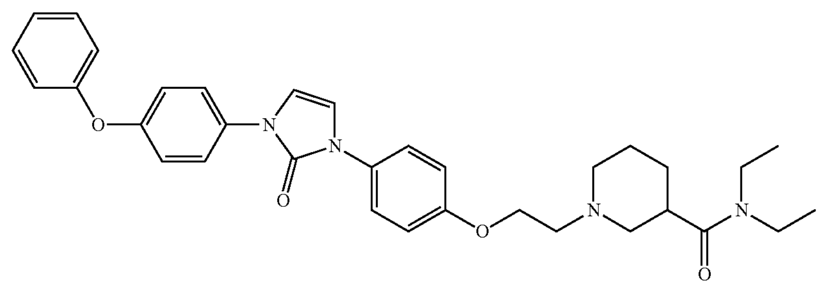 | C33H38N4O4 | 554.70 | 555 |
| 16 | 1-{4-[2-(1,4-Dioxa-8-azaspiro[4.5]dec-8-yl)ethoxy]phenyl}-3-(4-phenoxyphenyl)-1,3-dihydroimidazol-2-one | 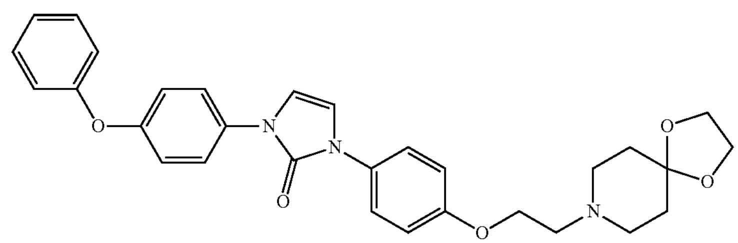 | C30H31N3O5 | 513.60 | 514 |
| 17 | 1-(4-{2-[Methyl-(2-pyridin-2-ylethyl)amino]ethoxy}phenyl)-3-(4-phenoxyphenyl)-1,3-dihydroimidazol-2-one | 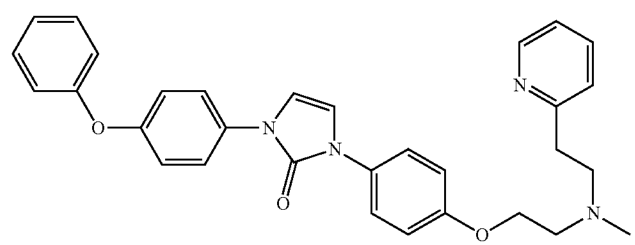 | C31H30N4O3 | 506.61 | 507 |

TABLE 2-continued

| Ex. No. | Name | Structure | Molecular formula | Molecular weight | [M + H]⁺ ESI-MS |
|---|---|---|---|---|---|
| 18 | 1-(4-Phenoxyphenyl)-3-{4-[2-(4-phenylbutylamino)ethoxy]phenyl}-1,3-dihydroimidazol-2-one | 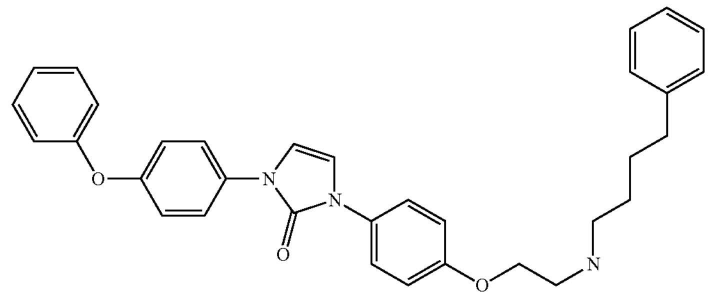 | C33H33N3O3 | 519.65 | 520 |
| 19 | 1-{4-[2-(Allylcyclopentylamino)ethoxy]phenyl}-3-(4-phenoxyphenyl)-1,3-dihydroimidazol-2-one | 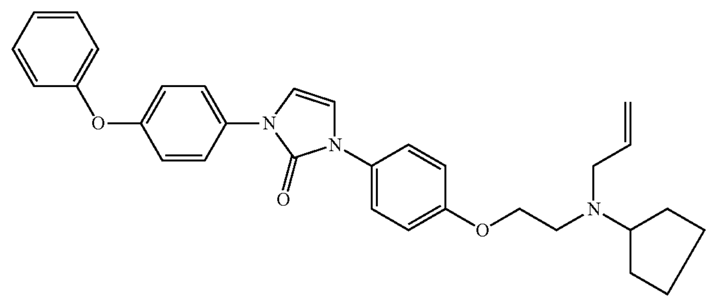 | C31H33N3O3 | 495.63 | 496 |
| 20 | 1-{4-[2-Phenoxyethylamino)ethoxy]phenyl}-3-(4-phenoxyphenyl)-1,3-dihydroimidazol-2-one | 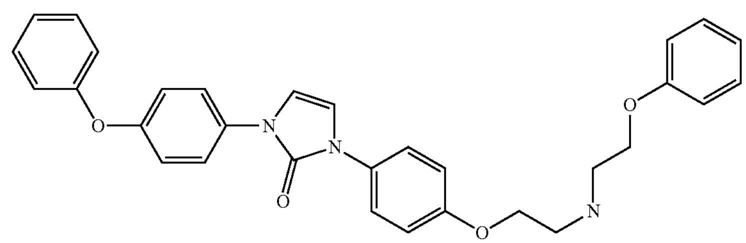 | C31H29N3O4 | 507.59 | 508 |

TABLE 2-continued

| Ex. No. | Name | Structure | Molecular formula | Molecular weight | [M + H]+ ESI-MS |
|---|---|---|---|---|---|
| 21 | 1-{4-[2-(2-Cyclohex-1-enylethylamino)ethoxy]phenyl}-3-(4-phenoxyphenyl)-1,3-dihydroimidazol-2-one | 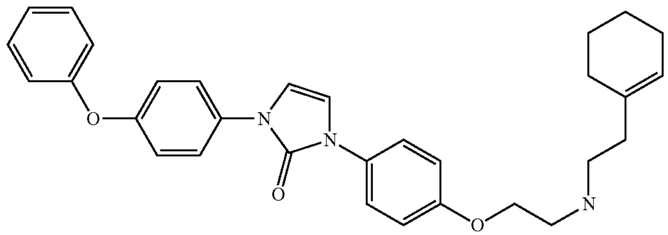 | C31H33N3O3 | 495.63 | 496 |
| 22 | 1-{4-[2-[(1-Hydroxycyclohexylmethyl)amino]ethoxy]phenyl}-3-(4-phenoxyphenyl)-1,3-dihydroimidazol-2-one | 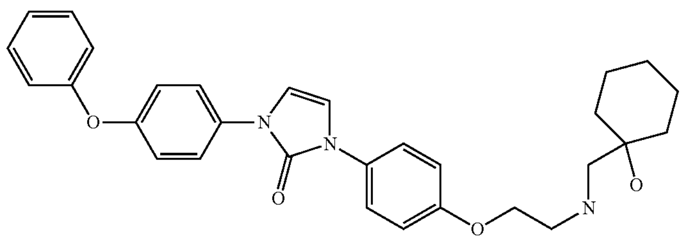 | C30H33N3O4 | 499.62 | 500 |
| 23 | (S)-3-(2-{4-[2-Oxo-3-(4-phenoxyphenyl)-2,3-dihydroimidazol-1-yl]phenoxy}ethylamino)azepan-2-one | 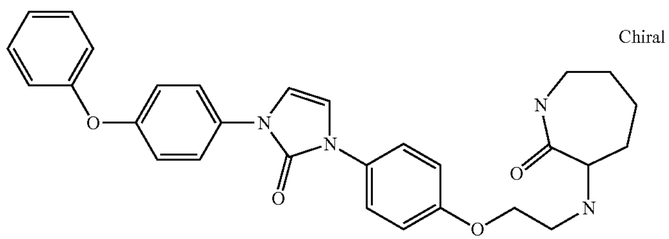 | C29H30N4O4 | 498.59 | 499 |
| 24 | 1-{4-[2-(4-Acetylpiperazin-1-yl)ethoxy]phenyl}-3-(4-phenoxyphenyl)-1,3-dihydroimidazol-2-one | 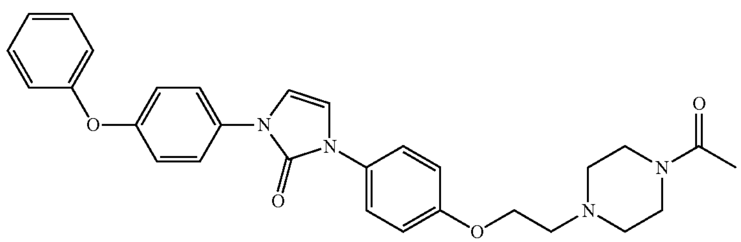 | C29H30N4O4 | 498.59 | 499 |

TABLE 2-continued

| Ex. No. | Name | Structure | Molecular formula | Molecular weight | [M + H]+ ESI-MS |
|---|---|---|---|---|---|
| 25 | 1-(4-{2-[3-(2-Oxopyrrolidin-1-yl)propylamino]ethoxy}phenyl)-3-(4-phenoxyphenyl)-1,3-dihydroimidazol-2-one | 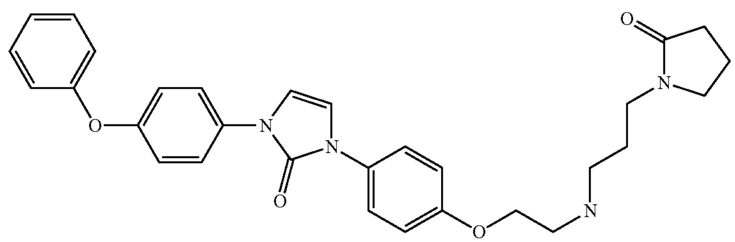 | C30H32N4O4 | 512.61 | 513 |
| 26 | 1-{4-[2-(5-Hydroxypentyl)amino]ethoxy]phenyl}-3-(4-phenoxyphenyl)-1,3-dihydroimidazol-2-one | 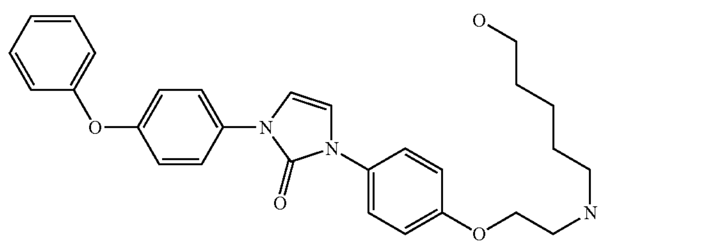 | C28H31N3O4 | 473.58 | 474 |
| 27 | 1-(4-Phenoxyphenyl)-3-(4-{2-[(tetrahydrofuran-2-ylmethyl)amino]ethoxy}phenyl)-1,3-dihydroimidazol-2-one | 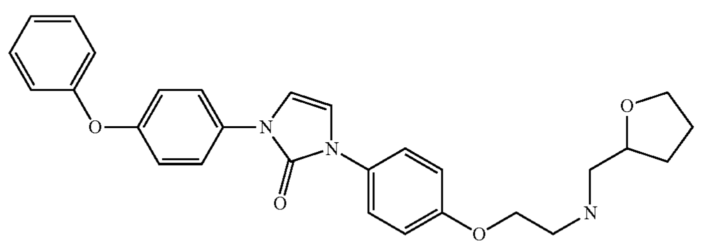 | C28H29N3O4 | 471.56 | 472 |
| 28 | 1-{4-[2-(4-Hydroxypiperidin-1-yl)ethoxy]phenyl}-3-(4-phenoxyphenyl)-1,3-dihydroimidazol-2-one | 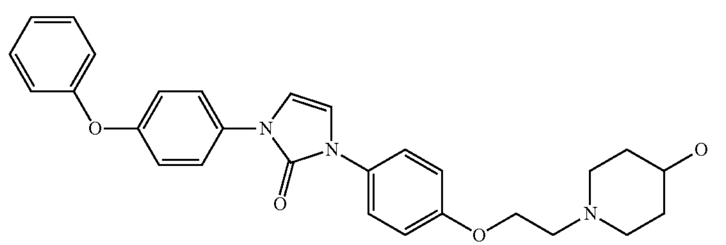 | C28H29N3O4 | 471.56 | 472 |

TABLE 2-continued

| Ex. No. | Name | Structure | Molecular formula | Molecular weight | [M + H]+ ESI-MS |
|---|---|---|---|---|---|
| 29 | 1-{4-[2-(3,4-Dihydro-1H-isoquinolin-2-yl)ethoxy]phenyl}-3-(4-phenoxyphenyl)-1,3-dihydroimidazol-2-one | 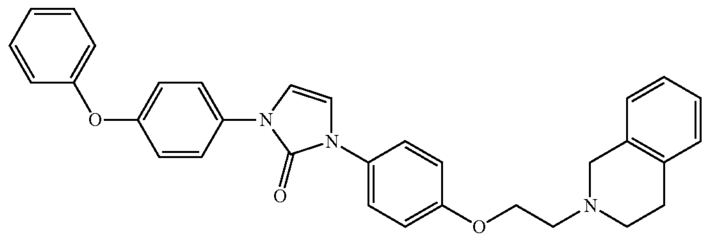 | C32H29N3O3 | 503.61 | 504 |
| 30 | 1-{4-[2-(4-Methylpiperidin-1-yl)ethoxy]phenyl}-3-(4-phenoxyphenyl)-1,3-dihydroimidazol-2-one | 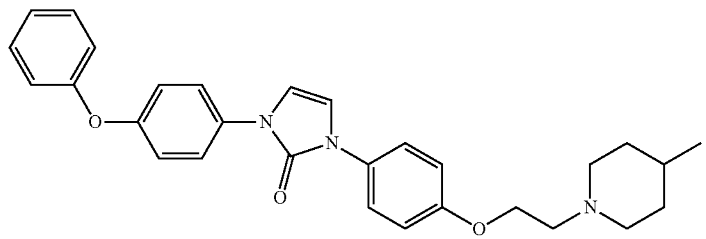 | C29H31N3O3 | 469.59 | 470 |
| 31 | 1-{4-[2-(2,2-Diphenylethylamino)ethoxy]phenyl}-3-(4-phenoxyphenyl)-1,3-dihydroimidazol-2-one | 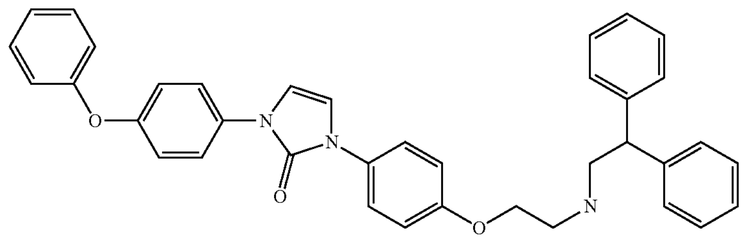 | C37H33N3O3 | 567.69 | 568 |
| 32 | 1-[4-(2-Phenethylaminoethoxy)phenyl]-3-(4-phenoxyphenyl)-1,3-dihydroimidazol-2-one | 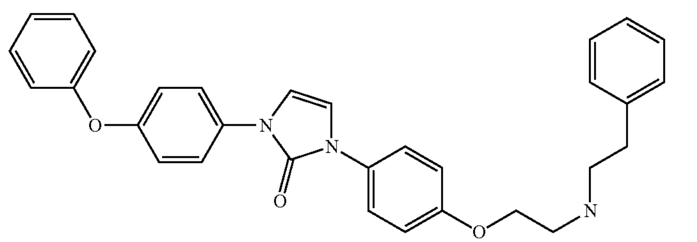 | C31H29N3O3 | 491.60 | 492 |

TABLE 2-continued

| Ex. No. | Name | Structure | Molecular formula | Molecular weight | [M + H]+ ESI-MS |
|---|---|---|---|---|---|
| 33 | 1-{4-[2-(Benzylmethylamino)ethoxy]phenyl}-3-(4-phenoxyphenyl)-1,3-dihydroimidazol-2-one | 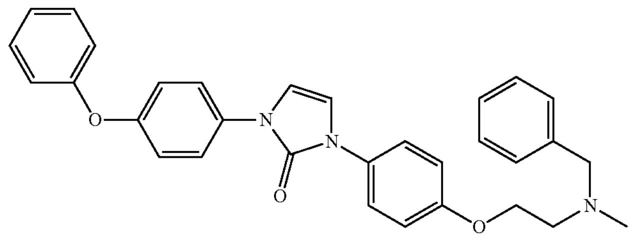 | C31H29N3O3 | 491.60 | 492 |
| 34 | 1-(4-Phenoxyphenyl)-3-(4-{2-[(thiophen-2-yl-methyl)amino]ethoxy}phenyl)-1,3-dihydroimidazol-2-one | 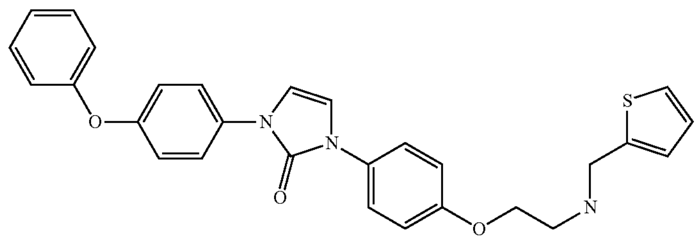 | C28H25N3O3S | 483.59 | 484 |
| 35 | 1-{4-[2-(4-Benzylpiperidin-1-yl)ethoxy]phenyl}-3-(4-phenoxyphenyl)-1,3-dihydroimidazol-2-one | 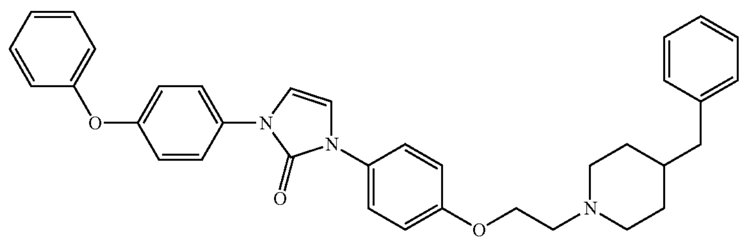 | C35H35N3O3 | 545.69 | 546 |
| 36 | 1-(4-Phenoxyphenyl)-3-[4-(2-thiazolidin-3-ylethoxy)phenyl]-1,3-dihydroimidazol-2-one | 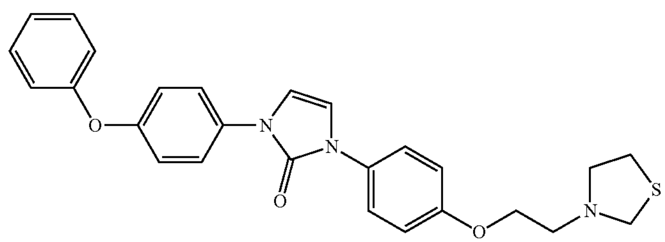 | C26H25N3O3S | 459.57 | 460 |

TABLE 2-continued

| Ex. No. | Name | Structure | Molecular formula | Molecular weight | [M + H]+ ESI-MS |
|---|---|---|---|---|---|
| 37 | 1-{4-[2-(Methyl)phenethylamino)ethoxy]phenyl]-3-(4-phenoxyphenyl)-1,3-dihydroimidazol-2-one | 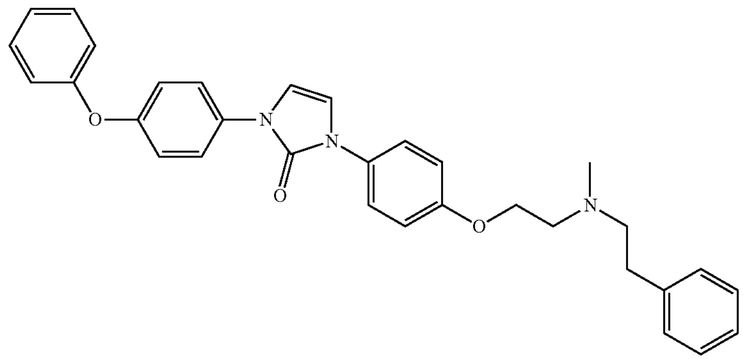 | C32H31N3O3 | 505.62 | 506 |
| 38 | 1-[4-(2-Cyclopropylaminoethoxy)phenyl]-3-(4-phenoxyphenyl)-1,3-dihydroimidazol-2-one | 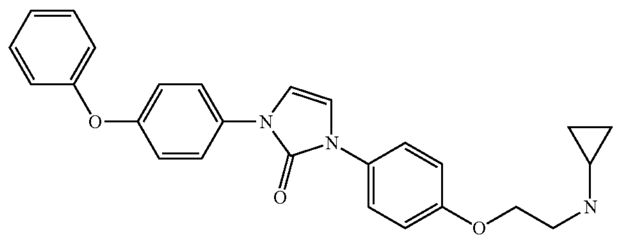 | C26H25N3O3 | 427.51 | 428 |
| 39 | 1-[4-(2-Cyclohexylaminoethoxy)phenyl]-3-(4-phenoxyphenyl)-1,3-dihydroimidazol-2-one | 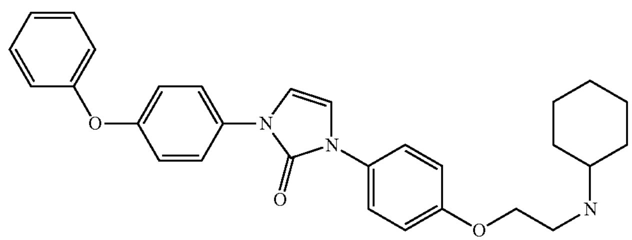 | C29H31N3O3 | 469.59 | 470 |

TABLE 2-continued

| Ex. No. | Name | Structure | Molecular formula | Molecular weight | [M + H]+ ESI-MS |
|---|---|---|---|---|---|
| 40 | 1-[4-(2-tert-Butylaminoethoxy)phenyl]-3-(4-phenoxyphenyl)-1,3-dihydroimidazol-2-one | 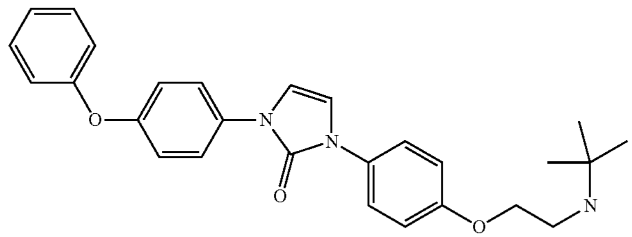 | C27H29N3O3 | 443.55 | 444 |
| 41 | 1-(4-Phenoxyphenyl)-3-{4-[2-(2-pyridin-4-ylethylamino)ethoxy]phenyl}-1,3-dihydroimidazol-2-one | 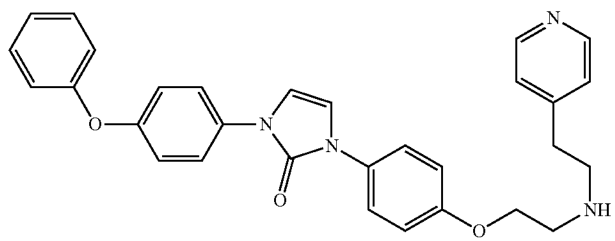 | C30H28N4O3 | 492.58 | 493 |
| 42 | 1-[4-(2-isopropylaminoethoxy)phenyl]-3-(4-phenoxyphenyl)-1,3-dihydroimidazol-2-one | 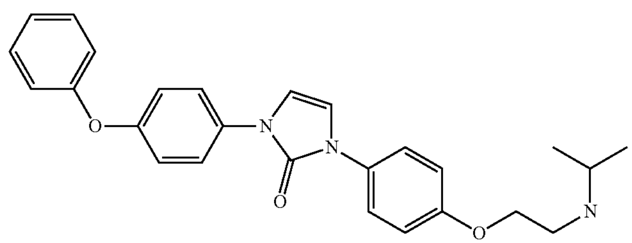 | C26H27N3O3 | 429.52 | 430 |
| 43 | N-[1-(2-{4-[2-Oxo-3-(4-phenoxyphenyl)-2,3-dihydroimidazol-1-yl]phenoxy}ethyl)pyrrolidin-3-yl]acetamide | 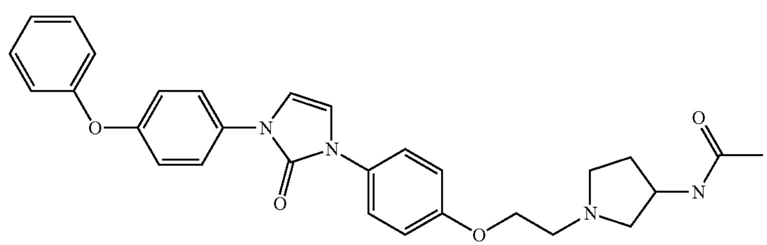 | C29H30N4O4 | 498.59 | 499 |

TABLE 2-continued

| Ex. No. | Name | Structure | Molecular formula | Molecular weight | [M + H]+ ESI-MS |
|---|---|---|---|---|---|
| 44 | 1-{4-[2-(4-Hydroxy-4-phenylpiperidin-1-yl)ethoxy]phenyl}-3-(4-phenoxyphenyl)-1,3-dihydroimidazol-2-one | 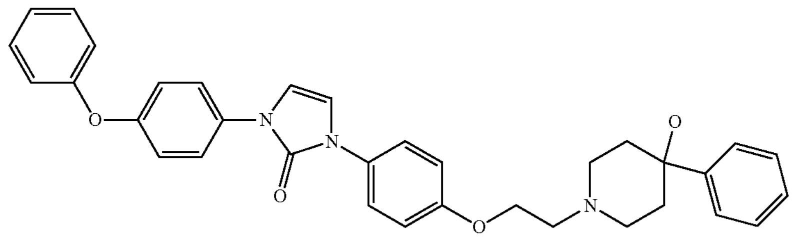 | C34H33N3O4 | 547.66 | 548 |
| 45 | 1-[4-(2-Imidazol-1-ylethoxy)phenyl]-3-(4-phenoxyphenyl)-1,3-dihydroimidazol-2-one | 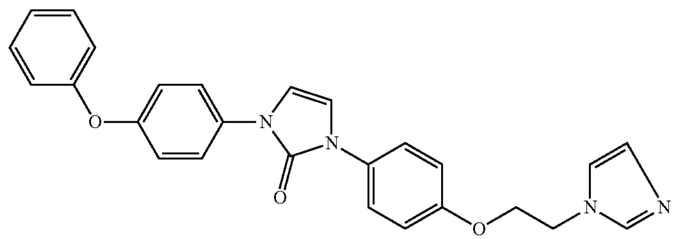 | C26H22N4O3 | 438.49 | 439 |
| 46 | 1-(4-Phenoxyphenyl)-3-[4-(2-pyrazol-1-yl-ethoxy)phenyl]-1,3-dihydroimidazol-2-one | 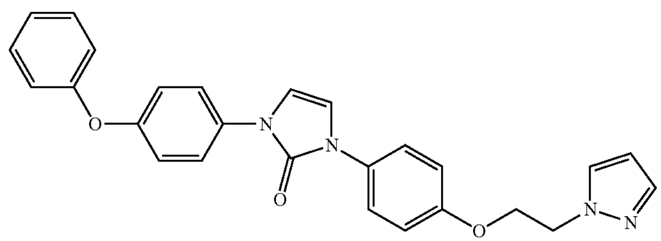 | C26H22N4O3 | 438.49 | 439 |

TABLE 2-continued
| Ex. No. | Name | Structure | Molecular formula | Molecular weight | [M + H]+ ESI-MS |
|---|---|---|---|---|---|
| 47 | (S)-1-(2-{4-[2-Oxo-3-(4-phenoxyphenyl)-2,3-dihydroimidazol-1-yl]phenoxy}ethyl)pyrrolidine-2-carboxylic acid ethyl ester | 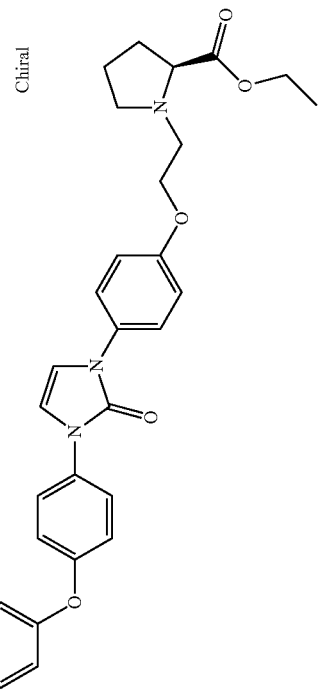 Chiral | C30H31N3O5 | 513.60 | 514 |
| 48 | 1-{4-[2-(Indan-2-yl)amino)ethoxy]phenyl}-3-(4-phenoxyphenyl)-1,3-dihydroimidazol-2-one | 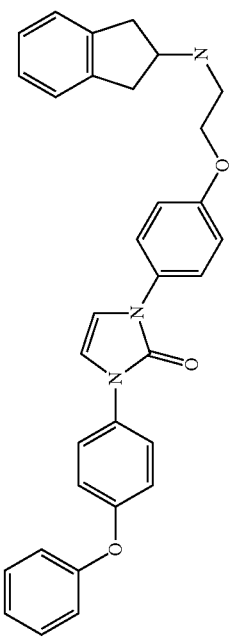 | C32H29N3O3 | 503.61 | 504 |
| 49 | 1-{4-[2-(2-Ethylpiperidin-1-yl)ethoxy]phenyl}-3-(4-phenoxyphenyl)-1,3-dihydroimidazol-2-one | 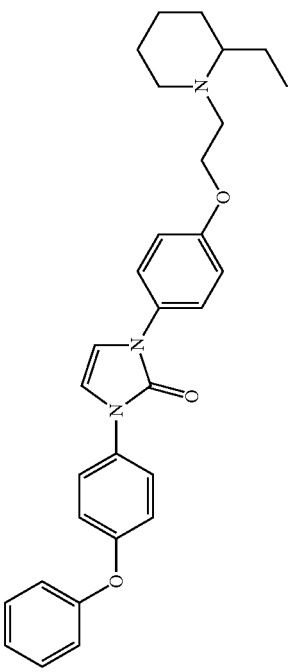 | C30H33N3O3 | 483.62 | 484 |

TABLE 2-continued

| Ex. No. | Name | Structure | Molecular formula | Molecular weight | [M + H]+ ESI-MS |
|---|---|---|---|---|---|
| 50 | 1-{4-[2-(Cyclopropylmethylamino)ethoxy]phenyl}-3-(4-phenoxyphenyl)-1,3-dihydroimidazol-2-one | 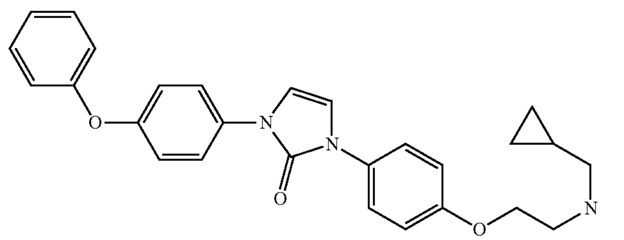 | C27H27N3O3 | 441.53 | 442 |
| 51 | 1-{4-[2-(Indan-1-ylamino)ethoxy]phenyl}-3-(4-phenoxyphenyl)-1,3-dihydroimidazol-2-one | 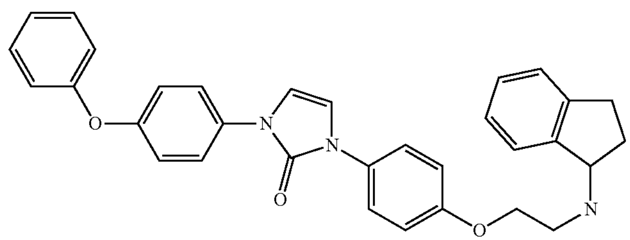 | C32H29N3O3 | 503.61 | 504 |
| 52 | 1-(4-Phenoxyphenyl)-3-{4-[2-(4-phenylpiperazin-1-yl)ethoxy]phenyl}-1,3-dihydroimidazol-2-one | 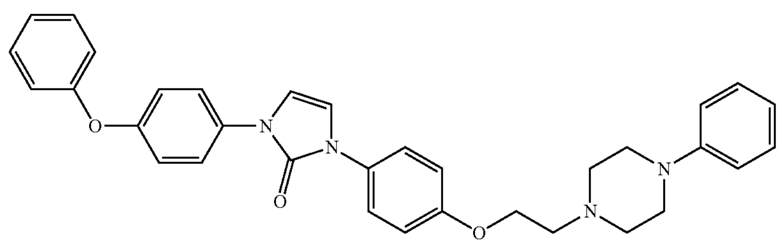 | C33H32N4O3 | 532.65 | 533 |
| 53 | 1-{4-[2-(4-Phenethylpiperazin-1-yl)ethoxy]phenyl}-3-(4-phenoxyphenyl)-1,3-dihydroimidazol-2-one | 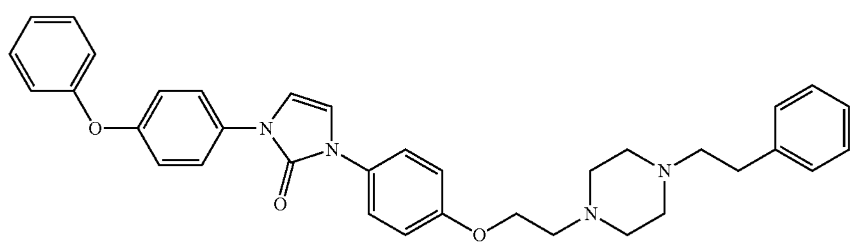 | C35H36N4O3 | 560.70 | 561 |

TABLE 2-continued

| Ex. No. | Name | Structure | Molecular formula | Molecular weight | [M + H]+ ESI-MS |
|---|---|---|---|---|---|
| 54 | 1-[4-(2-Benzoimidazol-1-yl)ethoxy)phenyl]-3-(4-phenoxyphenyl)-1,3-dihydroimidazol-2-one | 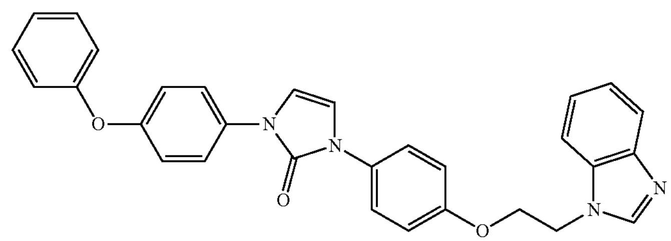 | C30H24N4O3 | 488.55 | 489 |
| 55 | 1-(4-{2-[2-(3-Methoxyphenyl)ethylamino]-ethoxy}phenyl)-3-(4-phenoxyphenyl)-1,3-dihydroimidazol-2-one | 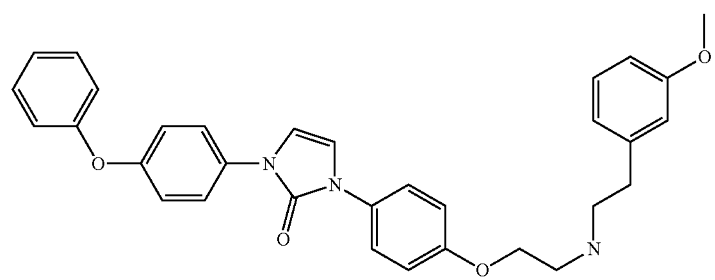 | C32H31N3O4 | 521.62 | 522 |
| 56 | 1-{4-[2-(2-Methyl-4,5-dihydroimidazol-1-yl)ethoxy]phenyl}-3-(4-phenoxyphenyl)-1,3-dihydroimidazol-2-one | 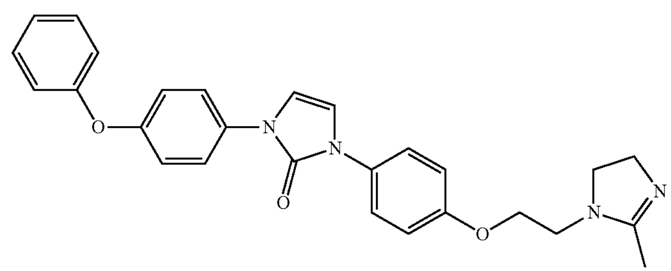 | C27H26N4O3 | 454.53 | 455 |

TABLE 2-continued

| Ex. No. | Name | Structure | Molecular formula | Molecular weight | [M + H]⁺ ESI-MS |
|---|---|---|---|---|---|
| 57 | 1-{4-[2-(4-Ethylpiperazin-1-yl)ethoxy]phenyl}-3-(4-phenoxyphenyl)-1,3-dihydroimidazol-2-one | 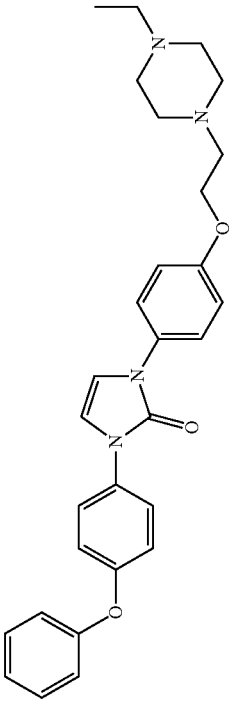 | C29H32N4O3 | 484.60 | 485 |
| 58 | 1-{4-[2-(3,6-Dihydro-2H-pyridin-1-yl)ethoxy]phenyl}-3-(4-phenoxyphenyl)-1,3-dihydroimidazol-2-one | 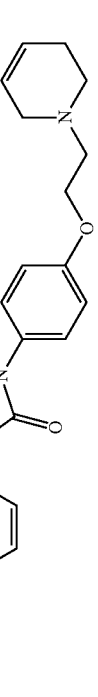 | C28H27N3O3 | 453.55 | 454 |
| 59 | 1-{4-[2-(3-Hydroxypyrrolidin-1-yl)ethoxy]phenyl}-3-(4-phenoxyphenyl)-1,3-dihydroimidazol-2-one | 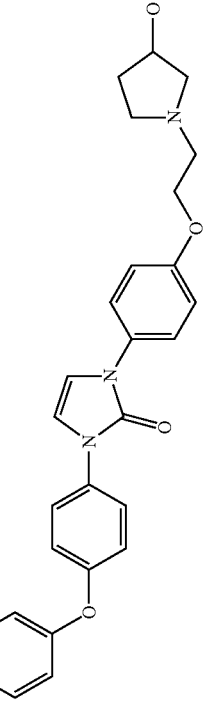 | C27H27N3O4 | 457.53 | 458 |
| 60 | 1-(4-Phenoxyphenyl)-3-{4-[2-((1S,2R)-2-phenylcyclopropyl)amino]ethoxy]phenyl}-1,3-dihydroimidazol-2-one | 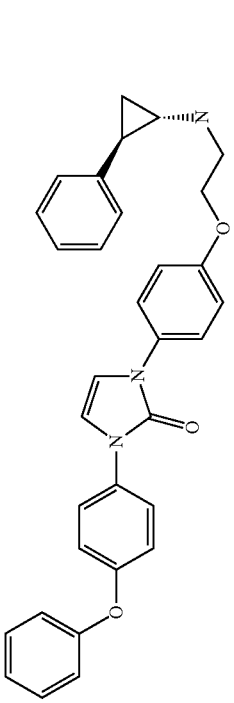 | C32H29N3O3 | 503.61 | 504 |

TABLE 2-continued

| Ex. No. | Name | Structure | Molecular formula | Molecular weight | [M + H]+ ESI-MS |
|---|---|---|---|---|---|
| 61 | 1-{4-[(4aR,8aS)-2-(Octahydroisoquinolin-2-yl)ethoxy]phenyl]-3-(4-phenoxyphenyl)-1,3-dihydroimidazol-2-one | 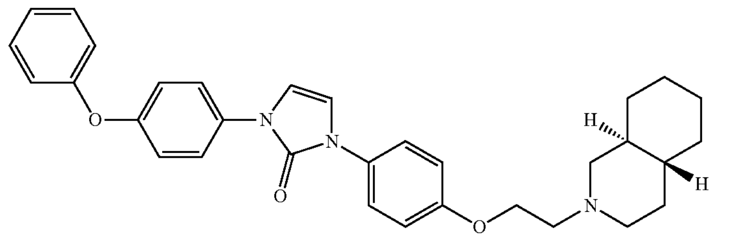 | C32H35N3O3 | 509.65 | 510 |
| 62 | 1-{4-[(4aS,8aS)-2-(Octahydroisoquinolin-2-yl)ethoxy]phenyl]-3-(4-phenoxyphenyl)-1,3-dihydroimidazol-2-one | 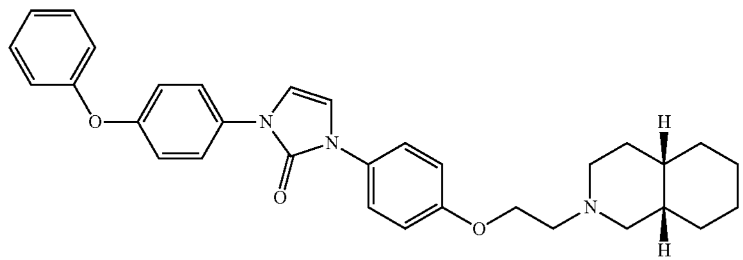 | C32H35N3O3 | 509.65 | 510 |
| 63 | 1-[4-(2-[[2-(1H-Indol-3-yl)ethyl]methylamino]-ethoxy)phenyl]-3-(4-phenoxyphenyl)-1,3-dihydroimidazol-2-one | 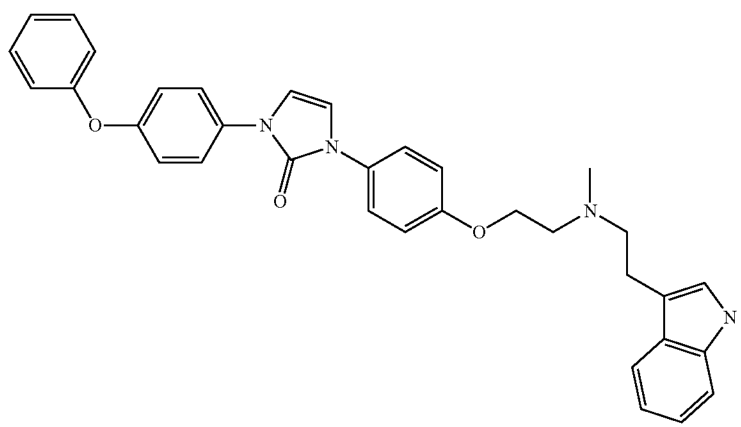 | C34H32N4O3 | 544.66 | 545 |

TABLE 2-continued

| Ex. No. | Name | Structure | Molecular formula | Molecular weight | [M + H]+ ESI-MS |
|---|---|---|---|---|---|
| 64 | 1-(4-{2-(2-Chlorophenyl)ethylamino]-ethoxy}phenyl)-3-(4-phenoxyphenyl)-1,3-dihydroimidazol-2-one | 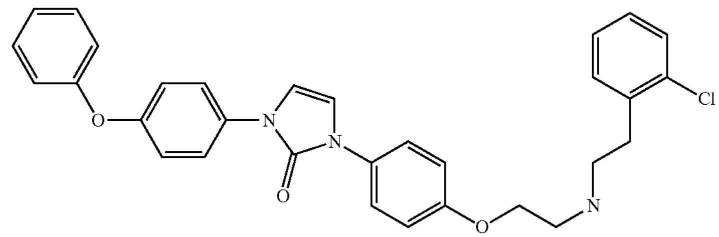 | C31H28ClN3O3 | 526.04 | 526 |
| 65 | 1-(4-{2-[(5-Chlorothiophen-2-ylmethyl)amino]ethoxy}phenyl)-3-(4-phenoxyphenyl)-1,3-dihydroimidazol-2-one | 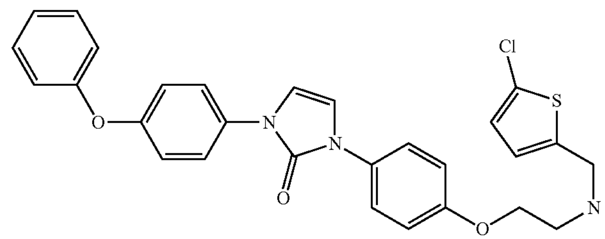 | C28H24ClN3O3S | 518.04 | 518 |
| 66 | 1-(4-{2-[((1R,2R)-2-Benzyloxycyclopentyl-amino]ethoxy]phenyl}-3-(4-phenoxyphenyl)-1,3-dihydroimidazol-2-one | 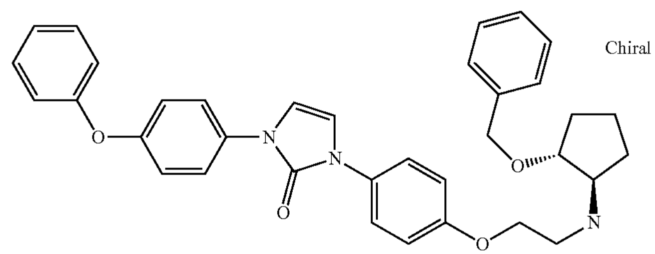 | C35H35N3O4 | 561.69 | 562 |
| 67 | 1-{4-[2-((S)-8-Methoxy-1,2,3,4-tetrahydronaphthalen-2-ylamino)ethoxy]phenyl}-3-(4-phenoxyphenyl)-1,3-dihydroimidazol-2-one | 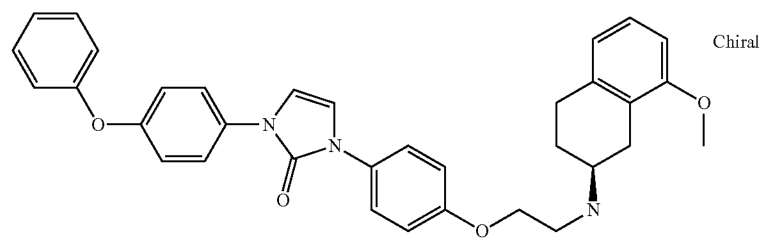 | C34H33N3O4 | 547.66 | 548 |

TABLE 2-continued

| Ex. No. | Name | Structure | Molecular formula | Molecular weight | [M + H]+ ESI-MS |
|---|---|---|---|---|---|
| 68 | 1-{4-[2-(4-Benzyl-4-hydroxypiperidin-1-yl)-ethoxy]phenyl}-3-(4-phenoxyphenyl)-1,3-dihydroimidazol-2-one | 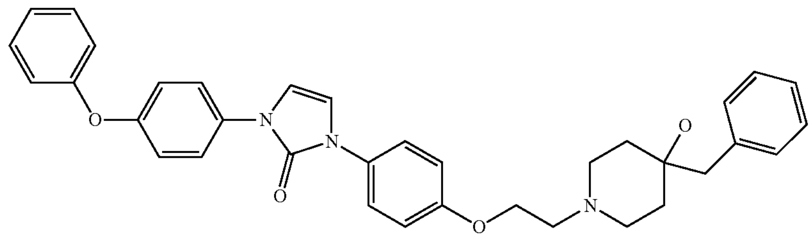 | C35H35N3O4 | 561.69 | 562 |
| 69 | 1-{4-[2-(5-Bromo-2,3-dihydroindol-1-yl)ethoxy]phenyl}-3-(4-phenoxyphenyl)-1,3-dihydroimidazol-2-one | 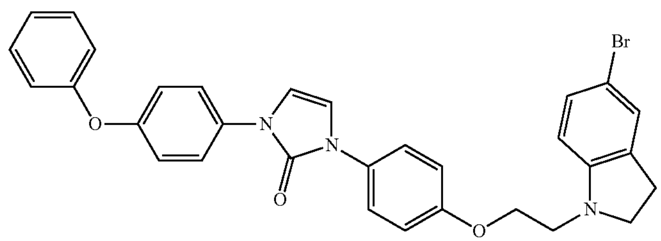 | C31H26BrN3O3 | 568.48 | 568 |
| 70 | 1-{4-[2-(5-Ethyl-2-methylpiperidin-1-yl)ethoxy]phenyl}-3-(4-phenoxyphenyl)-1,3-dihydroimidazol-2-one | 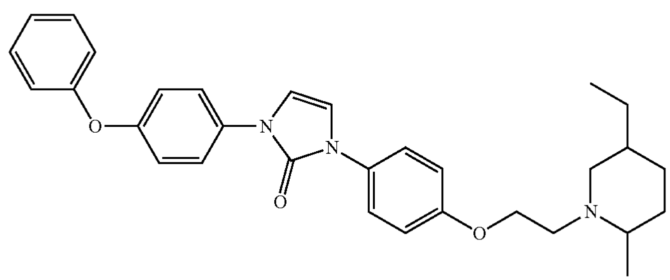 | C31H35N3O3 | 497.64 | 498 |

TABLE 2-continued

| Ex. No. | Name | Structure | Molecular formula | Molecular weight | [M + H]+ ESI-MS |
|---|---|---|---|---|---|
| 71 | 1-{4-[2-(2,5-Dimethylpyrrolidin-1-yl)ethoxy]phenyl}-3-(4-phenoxyphenyl)-1,3-dihydroimidazol-2-one | 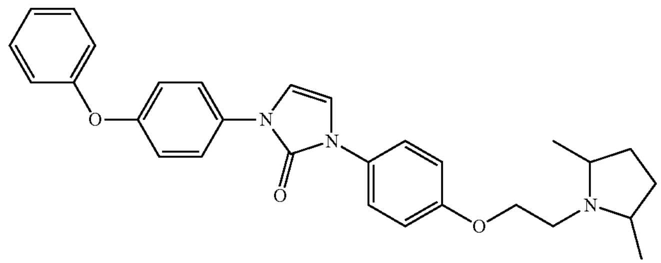 | C29H31N3O3 | 469.59 | 470 |
| 72 | 1-{4-[2-(Methylpropylamino)ethoxy]phenyl}-3-(4-phenoxyphenyl)-1,3-dihydroimidazol-2-one | 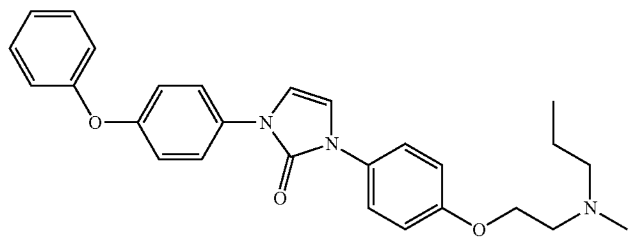 | C27H29N3O3 | 443.55 | 444 |
| 73 | 1-{4-[2-([1,3]-Dioxolan-2-ylmethylmethylamino)ethoxy]phenyl}-3-(4-phenoxyphenyl)-1,3-dihydroimidazol-2-one | 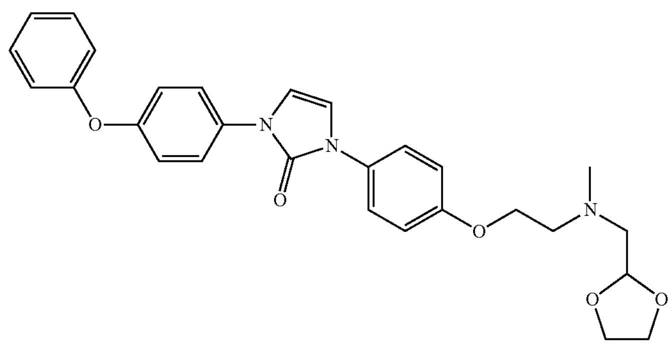 | C28H29N3O5 | 487.56 | 488 |

TABLE 2-continued

| Ex. No. | Name | Structure | Molecular formula | Molecular weight | [M + H]+ ESI-MS |
|---|---|---|---|---|---|
| 74 | 1-{4-[2-(2-Methylpyrrolidin-1-yl)ethoxyphenyl]-3-(4-phenoxyphenyl)-1,3-dihydroimidazol-2-one | 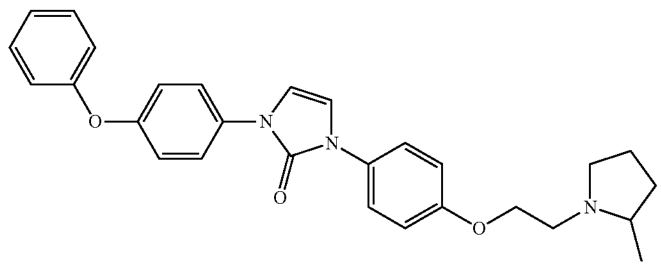 | C28H29N3O3 | 455.56 | 456 |
| 75 | 1-{4-[2-(Isopropylmethylamino)ethoxy]phenyl}-3-(4-phenoxyphenyl)-1,3-dihydroimidazol-2-one | 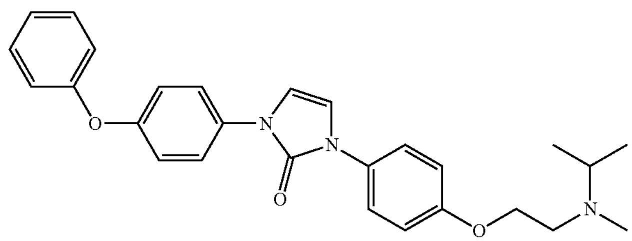 | C27H29N3O3 | 443.55 | 444 |
| 76 | 1-{4-[2-((R)-2-Methoxymethylpyrrolidin-1-yl)ethoxy]phenyl}-3-(4-phenoxyphenyl)-1,3-dihydroimidazol-2-one | 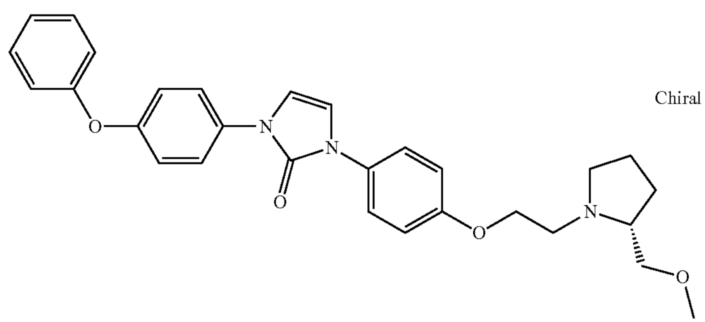 | C29H31N3O4 | 485.59 | 486 |

TABLE 2-continued

| Ex. No. | Name | Structure | Molecular formula | Molecular weight | [M + H]+ ESI-MS |
|---|---|---|---|---|---|
| 77 | (S)-1-(2-{4-[2-Oxo-3-(4-phenoxyphenyl)-2,3-dihydroimidazol-1-yl]phenoxy}ethyl)pyrrolidine-2-carboxylic acid dimethylamide | 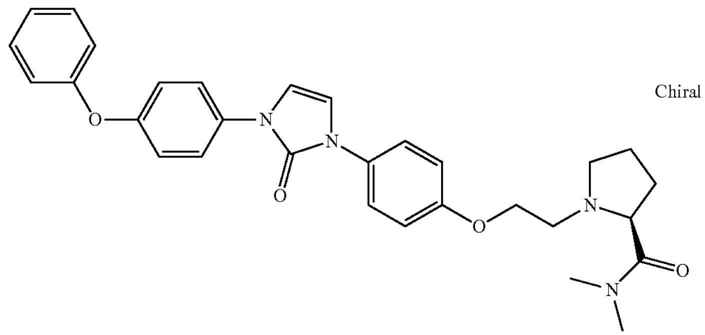 | C30H32N4O4 | 512.61 | 513 |
| 78 | 1-{4-[2-[(2-Methoxyethyl)methylamino]ethoxy]phenyl}-3-(4-phenoxyphenyl)-1,3-dihydroimidazol-2-one | 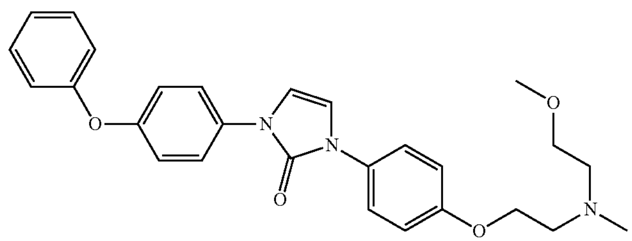 | C27H29N3O4 | 459.55 | 460 |
| 79 | 1-{4-[2-(7-Azabicyclo[2.2.1]hept-7-yl)phenyl]-3-(4-phenoxyphenyl)-1,3-dihydroimidazol-2-one | 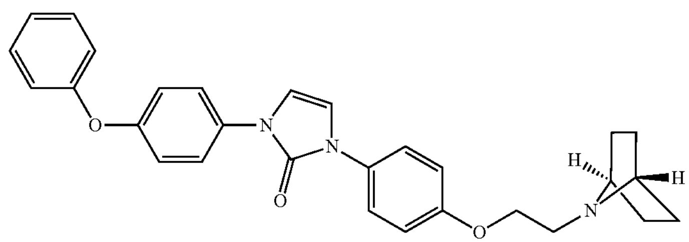 | C29H29N3O3 | 467.57 | 468 |

TABLE 2-continued

| Ex. No. | Name | Structure | Molecular formula | Molecular weight | [M + H]+ ESI-MS |
|---|---|---|---|---|---|
| 80 | 1-(4-{2-[(1-Benzylpyrrolidin-3-yl)methylamino]ethoxy}phenyl)-3-(4-phenoxyphenyl)-1,3-dihydroimidazol-2-one | 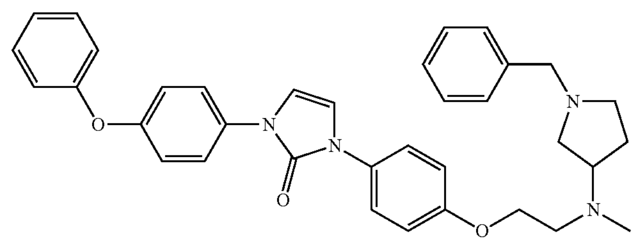 | C35H36N4O3 | 560.70 | 561 |
| 81 | 1-(4-{2-[(1,1-Dioxotetrahydro-1lambda6-thiophen-3-yl)methylamino]ethoxy}phenyl)-3-(4-phenoxyphenyl)-1,3-dihydroimidazol-2-one | 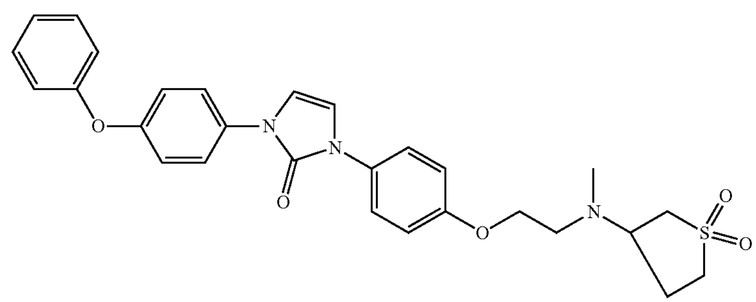 | C28H29N3O5S | 519.62 | 520 |
| 82 | 1-(4-[2-(Benzhydrylmethylamino]ethoxy]-phenyl]-3-(4-phenoxyphenyl)-1,3-dihydroimidazol-2-one | 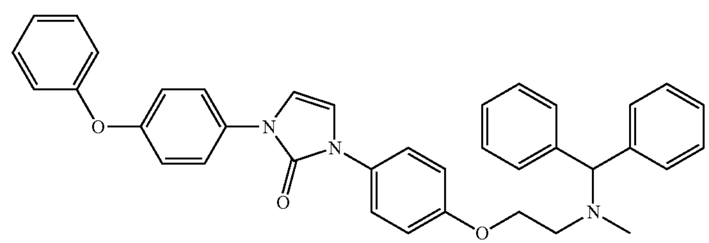 | C37H33N3O3 | 567.69 | 568 |
| 83 | 1-(4-{2-[((4S,5S)-2,2-Dimethyl-4-phenyl-[1,3]-dioxan-5-yl)methylamino]ethoxy}phenyl)-3-(4-phenoxyphenyl)-1,3-dihydroimidazol-2-one | 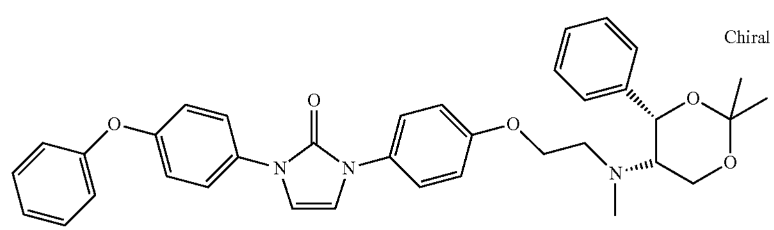 | C36H37N3O5 | 591.71 | 592 |

TABLE 2-continued

| Ex. No. | Name | Structure | Molecular formula | Molecular weight | [M + H]+ ESI-MS |
|---|---|---|---|---|---|
| 84 | 1-{4-[2-(3-Dimethylaminopyrrolidin-1-yl)ethoxy]phenyl}-3-(4-phenoxyphenyl)-1,3-dihydroimidazol-2-one | 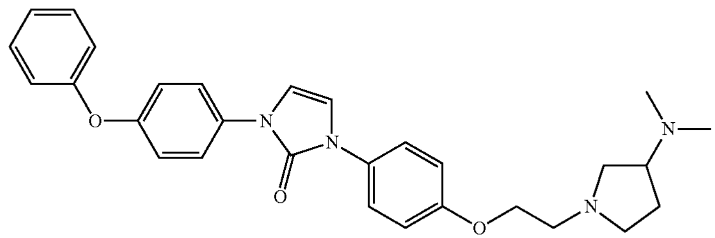 | C29H32N4O3 | 484.60 | 485 |
| 85 | 1-(4-Phenoxyphenyl)-3-{4-[2-(2-phenylpyrrolidin-1-yl)ethoxy]phenyl}-1,3-dihydroimidazol-2-one | 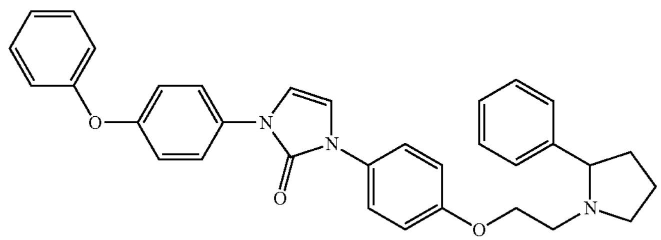 | C33H31N3O3 | 517.63 | 518 |
| 86 | 1-{4-[2-(2-Benzylpyrrolidin-1-yl)ethoxy]phenyl}-3-(4-phenoxyphenyl)-1,3-dihydroimidazol-2-one | 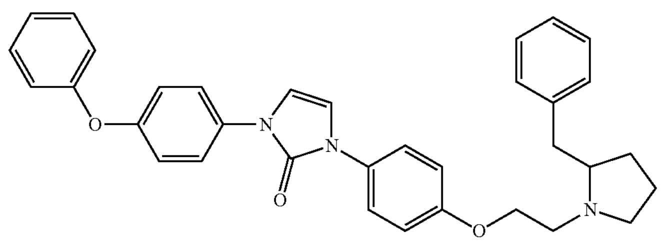 | C34H33N3O3 | 531.66 | 532 |
| 87 | 1-{4-[2-(2-Phenethylpyrrolidin-1-yl)ethoxy]phenyl}-3-(4-phenoxyphenyl)-1,3-dihydroimidazol-2-one | 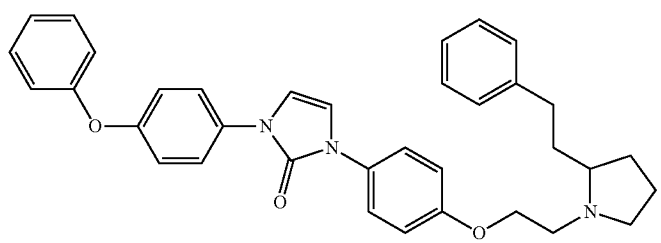 | C35H35N3O3 | 545.69 | 546 |

TABLE 2-continued

| Ex. No. | Name | Structure | Molecular formula | Molecular weight | [M + H]+ ESI-MS |
|---|---|---|---|---|---|
| 88 | 1-{4-[2-(2-Isopropylpyrrolidin-1-yl)ethoxy]phenyl}-3-(4-phenoxyphenyl)-1,3-dihydro-imidazol-2-one | 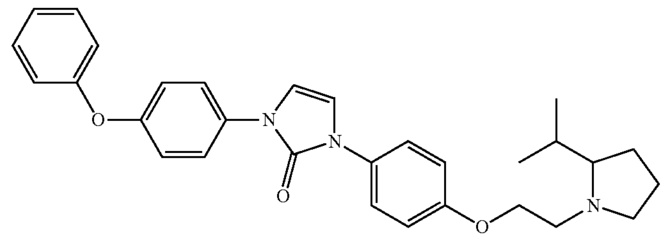 | C30H33N3O3 | 483.62 | 484 |
| 89 | 1-(4-Phenoxyphenyl)-3-{4-[2-(3-phenylpyrrolidin-1-yl)ethoxy]phenyl}-1,3-dihydro-imidazol-2-one | 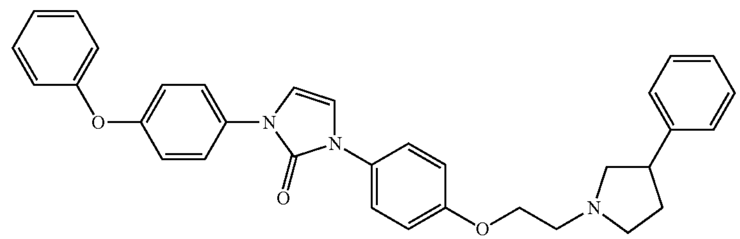 | C33H31N3O3 | 517.63 | 518 |
| 90 | 1-{4-[2-(3-Benzylpyrrolidin-1-yl)ethoxy]phenyl}-3-(4-phenoxyphenyl)-1,3-dihydro-imidazol-2-one | 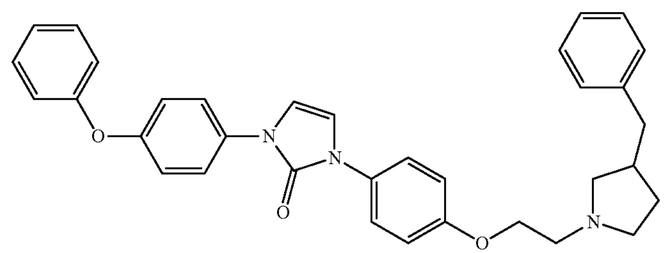 | C34H33N3O3 | 531.66 | 532 |
| 91 | 1-{4-[2-(3-Methanesulfonylpyrrolidin-1-yl)ethoxy]phenyl}-3-(4-phenoxyphenyl)-1,3-dihydroimidazol-2-one | 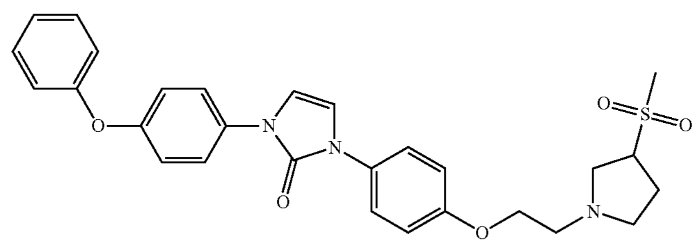 | C28H29N3O5S | 519.62 | 520 |

EXAMPLE 92

1-(4-sec-Butoxyphenyl)-3-[4-(2-dimethylaminoethoxy)phenyl]-1,3-dihydroimidazol-2-one

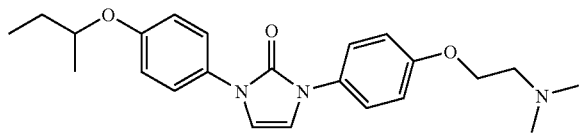

A solution of 1-[4-(2-dimethylaminoethoxy)phenyl]-3-(4-hydroxyphenyl)-1,3-dihydroimidazol-2-one (50 mg) in propionitrile (1 mL) was mixed with cesium carbonate (100 mg) and 2-butyl bromide (25 mg) and heated at 80° C. for 2 hours. The reaction solution was filtered and the concentrated. The residue was purified by preparative HPLC. The product with the molecular weight of 395.51 ($C_{23}H_{29}N_3O_3$); MS (ESI): 396 ([M+H]$^+$), was obtained as hydrotrifluoroacetate in this way.

1-[4-(2-Dimethylaminoethoxy)phenyl]-3-(4-hydroxyphenyl)-1,3-dihydroimidazol-2-one A suspension of 1-(4-benzyloxyphenyl)-1-(2,2-dimethoxyethyl)-3-[4-(2-dimethylaminoethoxy)phenyl]urea (4.9 g), palladium (10% on carbon, 1.0 g) and ethanol (40 mL) was stirred under hydrogen for 5 hours. The catalyst was filtered off and the filtrate was concentrated. The residue was taken up in trifluoroacetic acid (20 mL) and the solution was stirred for 48 hours. The reaction mixture was diluted with dichloromethane and washed with saturated sodium bicarbonate solution. The organic phase was dried and concentrated. The solid residue was stirred with acetonitrile, and the product was filtered off. The product with the molecular weight of 339.40 ($C_{19}H_{21}N_3O_3$); MS (ESI): 340 ([M+H]$^+$), was obtained in this way.

1-(4-Benzyloxyphenyl)-1-(2,2-dimethoxyethyl)-3-[4-(2-dimethylaminoethoxy)phenyl]urea Carbonyldiimidazole (2.7 g) was added to a solution of 4-(2-dimethylaminoethoxy)phenylamine (3.01 g) in dimethylformamide (40 mL) cooled in ice. After 30 minutes, (4-benzyloxyphenyl)-(2,2-dimethoxyethyl)amine (4.8 g) was added, and the mixture was heated at 80° C. for 30 minutes. After cooling, volatiles were removed and the residue was purified by MPLC (eluent: heptane/ethyl acetate 9:1). The product with the molecular weight of 493.61 ($C_{28}H_{35}N_3O_5$); MS (ESI): 494 ([M+H]$^+$), was obtained in this way.

(4-Benzyloxyphenyl)-(2,2-dimethoxyethyl)amine

A mixture of 4-benzyloxyaniline (10 g), bromoacetaldehyde dimethyl acetal (12.2 g), potassium carbonate (13.8 g) and dimethylformamide (150 mL) was heated at 100° C. for 5 hours. After cooling, the reaction solution was filtered and concentrated. The residue was purified by MPLC (eluent: heptane/ethyl acetate 4:1). The product with the molecular weight of 287.36 ($C_{17}H_{21}NO_3$); MS (ESI): 288 ([M+H]$^+$), was obtained in this way.

EXAMPLES 93–130

Further examples prepared as described in example 92 using the appropriate alkyl bromide are summarized in table 3.

TABLE 3

| Ex. No. | Structure | Name | Molecular formula | Molecular weight | [M + H]+ ESI-MS |
|---|---|---|---|---|---|
| 93 | 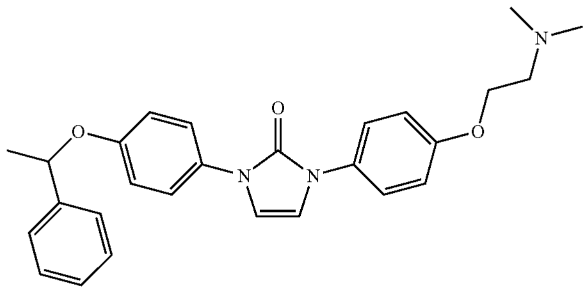 | 1-[4-(2-Dimethylaminoethoxy)phenyl]-3-[4-(1-phenylethoxy)phenyl]-1,3-dihydroimidazol-2-one | C27H29N3O3 | 443.55 | 444 |
| 94 | 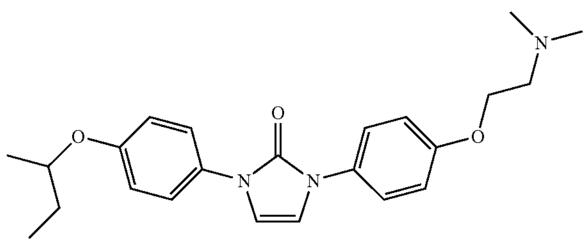 | 1-(4-sec-Butoxyphenyl)-3-[4-(2-dimethyl]aminoethoxy)phenyl]-1,3-dihydroimidazol-2-one | C23H29N3O3 | 395.51 | 396 |
| 95 | 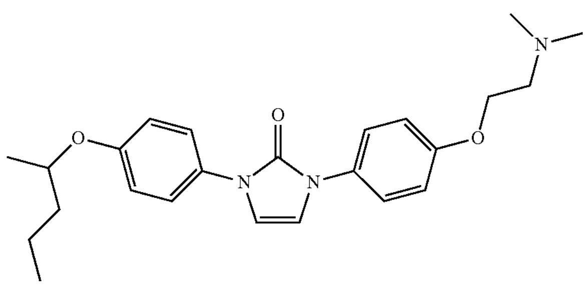 | 1-[4-(2-Dimethylaminoethoxy)phenyl]-3-[4-(1-methylbutoxy)phenyl]-1,3-dihydroimidazol-2-one | C24H31N3O3 | 409.53 | 410 |

TABLE 3-continued

| Ex. No. | Structure | Name | Molecular formula | Molecular weight | [M + H]+ ESI-MS |
|---|---|---|---|---|---|
| 96 | 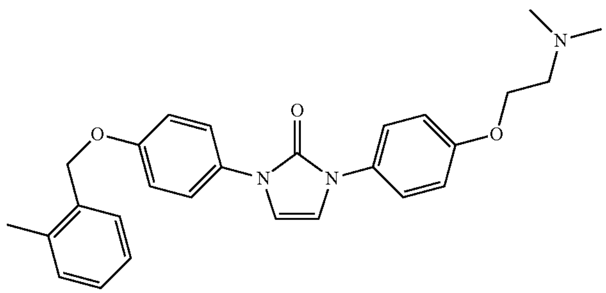 | 1-[4-(2-Dimethylaminoethoxy)phenyl]-3-[4-(2-methylbenzyloxy)phenyl]-1,3-dihydroimidazol-2-one | C27H29N3O3 | 443.55 | 444 |
| 97 | 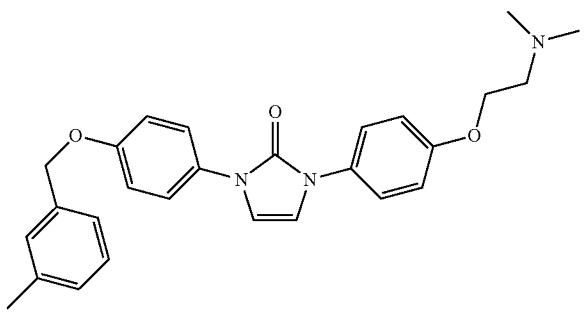 | 1-[4-(2-Dimethylaminoethoxy)phenyl]-3-[4-(3-methylbenzyloxy)phenyl]-1,3-dihydroimidazol-2-one | C27H29N3O3 | 443.55 | 444 |
| 98 | 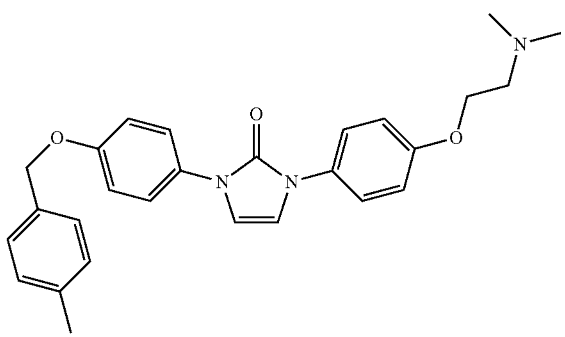 | 1-[4-(2-Dimethylaminoethoxy)phenyl]-3-[4-(4-methylbenzyloxy)phenyl]-1,3-dihydroimidazol-2-one | C27H29N3O3 | 443.55 | 444 |

TABLE 3-continued

| Ex. No. | Structure | Name | Molecular formula | Molecular weight | [M + H]⁺ ESI-MS |
|---|---|---|---|---|---|
| 99 | 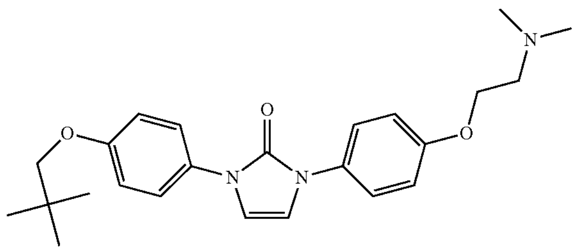 | 1-[4-(2-Dimethylaminoethoxyphenyl]-3-[4-(2,2-dimethylpropoxy)phenyl]-1,3-dihydroimidazol-2-one | C24H31N3O3 | 409.53 | 410 |
| 100 | 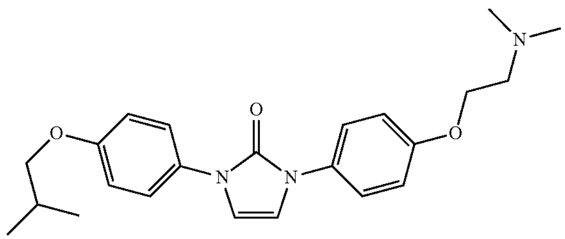 | 1-[4-(2-Dimethylaminoethoxyphenyl]-3-(4-isobutoxyphenyl)-1,3-dihydroimidazol-2-one | C23H29N3O3 | 395.51 | 396 |
| 101 | 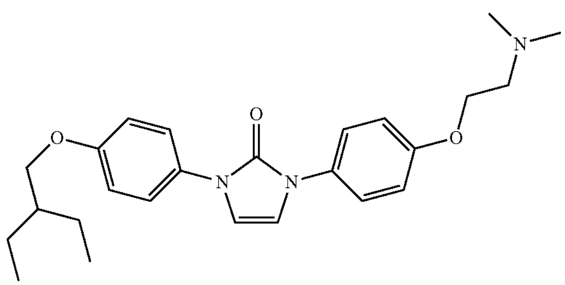 | 1-[4-(2-Dimethylaminoethoxyphenyl]-3-[4-(2-ethylbutoxy)phenyl]-1,3-dihydroimidazol-2-one | C25H33N3O3 | 423.56 | 424 |
| 102 | 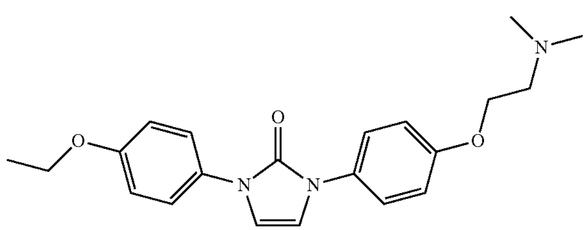 | 1-[4-(2-Dimethylaminoethoxyphenyl]-3-(4-ethoxyphenyl)-1,3-dihydroimidazol-2-one | C21H25N3O3 | 367.45 | 368 |

TABLE 3-continued

| Ex. No. | Structure | Name | Molecular formula | Molecular weight | [M + H]+ ESI-MS |
|---|---|---|---|---|---|
| 103 | 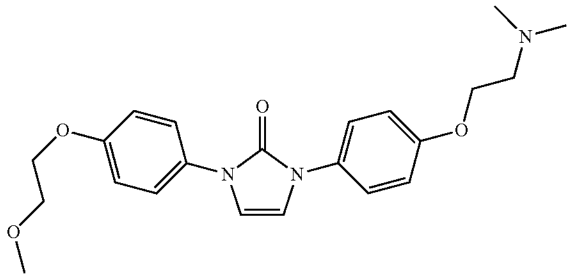 | 1-[4-(2-Dimethylaminoethoxy)phenyl]-3-[4-(2-methoxyethoxy)phenyl]-1,3-dihydroimidazol-2-one | C22H27N3O4 | 397.48 | 398 |
| 104 | 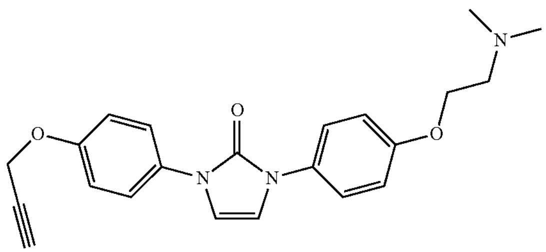 | 1-[4-(2-Dimethylaminoethoxy)phenyl]-3-(4-prop-2-ynyloxyphenyl)-1,3-dihydroimidazol-2-one | C22H23N3O3 | 377.45 | 378 |
| 105 | 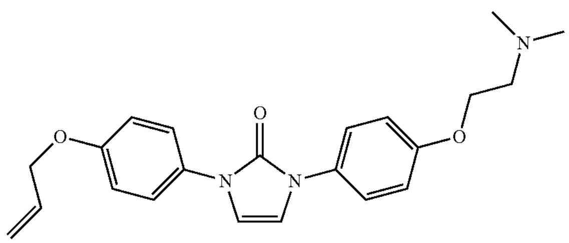 | 1-(4-Allyloxyphenyl)-3-[4-(2-dimethylaminoethoxy)phenyl]-1,3-dihydroimidazol-2-one | C22H25N3O3 | 379.46 | 380 |

TABLE 3-continued

| Ex. No. | Structure | Name | Molecular formula | Molecular weight | [M + H]+ ESI-MS |
|---|---|---|---|---|---|
| 106 | 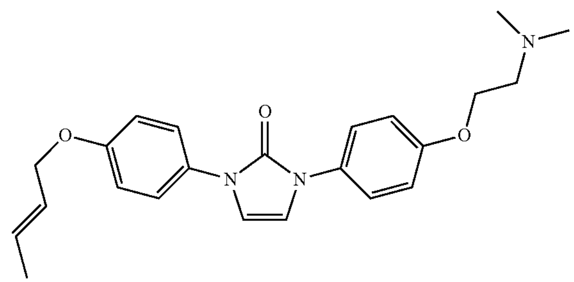 | 1-{4-[((E)-But-2-enyl)oxy]phenyl}-3-{4-[(2-dimethylaminoethyl)oxy]phenyl}-1,3-dihydroimidazol-2-one | C23H27N3O3 | 393.49 | 394 |
| 107 | 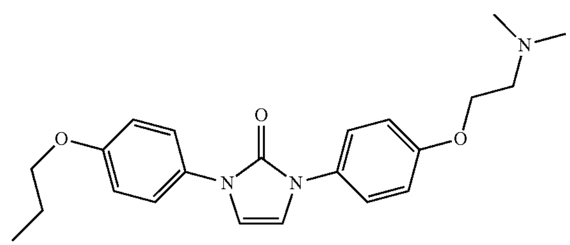 | 1-[4-(2-Dimethylaminoethoxy)phenyl]-3-(4-propoxyphenyl)-1,3-dihydroimidazol-2-one | C22H27N3O3 | 381.48 | 382 |
| 108 | 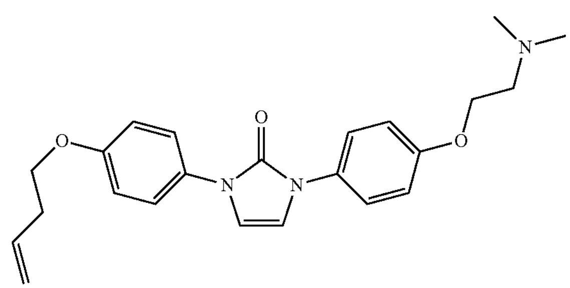 | 1-(4-But-3-enyloxyphenyl)-3-[4-(2-dimethylaminoethoxy)phenyl]-1,3-dihydroimidazol-2-one | C23H27N3O3 | 393.49 | 394 |

TABLE 3-continued

| Ex. No. | Structure | Name | Molecular formula | Molecular weight | [M + H]+ ESI-MS |
|---|---|---|---|---|---|
| 109 | 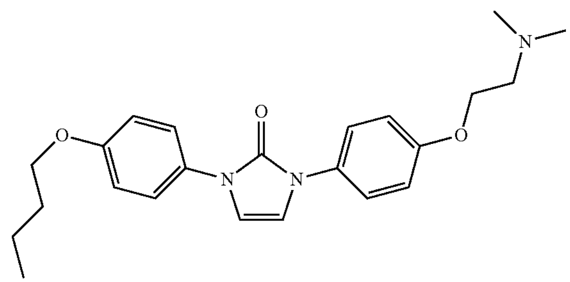 | 1-(4-Butoxyphenyl)-3-[4-(2-dimethylaminoethoxy)phenyl]-1,3-dihydroimidazol-2-one | C23H29N3O3 | 395.51 | 396 |
| 110 | 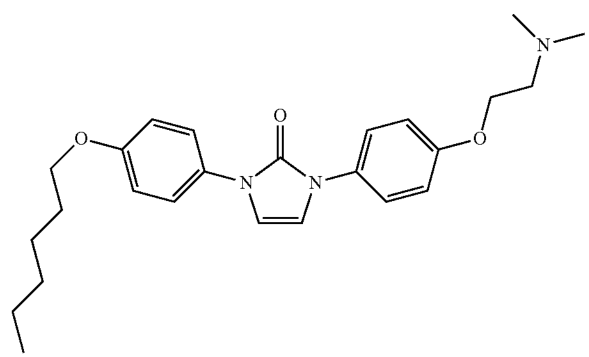 | 1-[4-(2-Dimethylaminoethoxy)phenyl]-3-(4-hexyloxyphenyl)-1,3-dihydroimidazol-2-one | C25H33N3O3 | 423.56 | 424 |
| 111 | 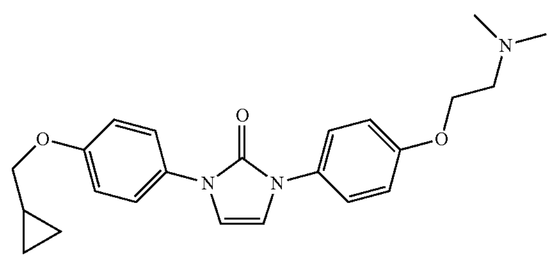 | 1-(4-Cyclopropylmethoxyphenyl)-3-[4-(2-dimethylaminoethoxy)phenyl]-1,3-dihydroimidazol-2-one | C23H27N3O3 | 393.49 | 394 |

TABLE 3-continued

| Ex. No. | Structure | Name | Molecular formula | Molecular weight | [M + H]+ ESI-MS |
|---|---|---|---|---|---|
| 112 | 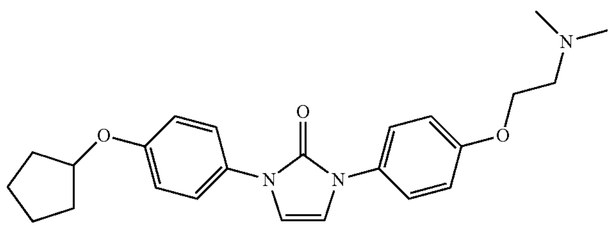 | 1-(4-Cyclopentyloxyphenyl)-3-[4-(2-dimethylaminoethoxy)phenyl]-1,3-dihydroimidazol-2-one | C24H29N3O3 | 407.52 | 408 |
| 113 | 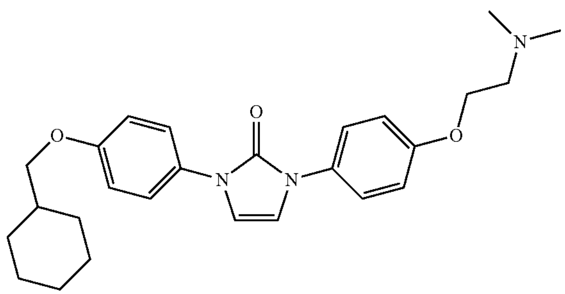 | 1-(4-Cyclohexylmethoxyphenyl)-3-[4-(2-dimethylaminoethoxy)phenyl]-1,3-dihydroimidazol-2-one | C26H33N3O3 | 435.57 | 436 |
| 114 | 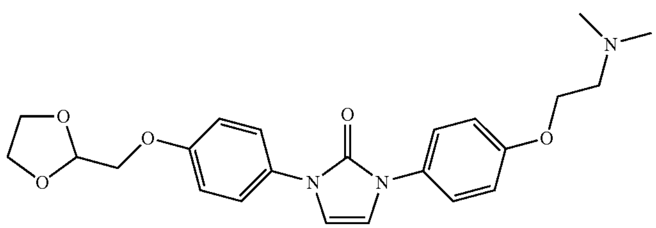 | 1-[4-(2-Dimethylaminoethoxy)phenyl]-3-[4-([1,3]dioxolan-2-ylmethoxy)phenyl]-1,3-dihydroimidazol-2-one | C23H27N3O5 | 425.49 | 426 |
| 115 | 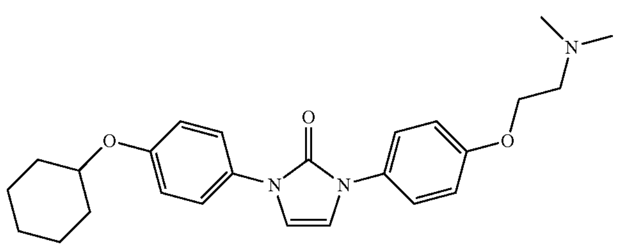 | 1-(4-Cyclohexyloxyphenyl)-3-[4-(2-dimethylaminoethoxy)phenyl]-1,3-dihydroimidazol-2-one | C25H31N3O3 | 421.54 | 422 |

TABLE 3-continued

| Ex. No. | Structure | Name | Molecular formula | Molecular weight | [M + H]+ ESI-MS |
|---|---|---|---|---|---|
| 116 | 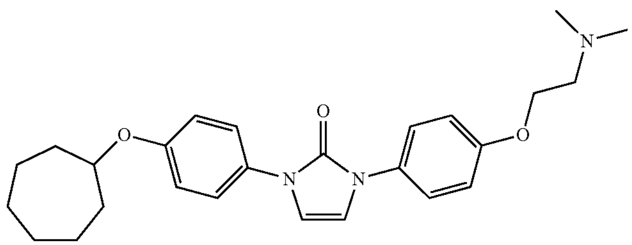 | 1-(4-Cycloheptyloxyphenyl)-3-[4-(2-dimethylaminoethoxy)phenyl]-1,3-dihydroimidazol-2-one | C26H33N3O3 | 435.57 | 436 |
| 117 | 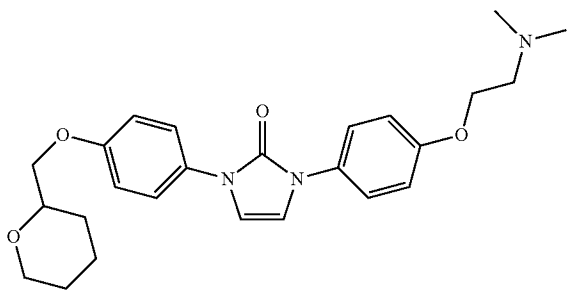 | 1-[4-(2-Dimethylaminoethoxy)phenyl]-3-[4-(tetrahydropyran-2-ylmethoxy)phenyl]-1,3-dihydroimidazol-2-one | C25H31N3O4 | 437.54 | 438 |
| 118 | 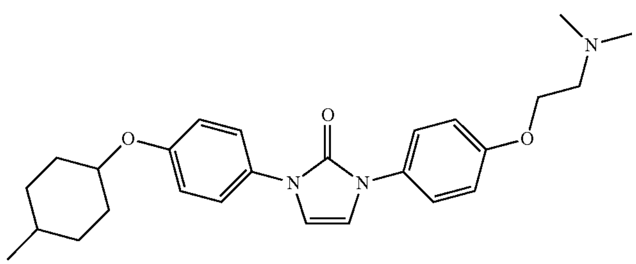 | 1-[4-(2-Dimethylaminoethoxy)phenyl]-3-[4-(4-methylcyclohexyloxy)phenyl]-1,3-dihydroimidazol-2-one | C26H33N3O3 | 435.57 | 436 |
| 119 | 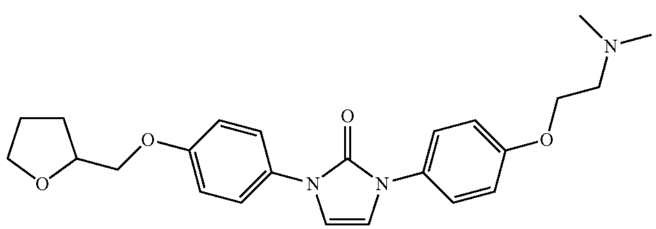 | 1-[4-(2-Dimethylaminoethoxy)phenyl]-3-[4-(tetrahydrofuran-2-ylmethoxy)phenyl]-1,3-dihydroimidazol-2-one | C24H29N3O4 | 423.52 | 424 |

TABLE 3-continued

| Ex. No. | Structure | Name | Molecular formula | Molecular weight | [M + H]+ ESI-MS |
|---|---|---|---|---|---|
| 120 | 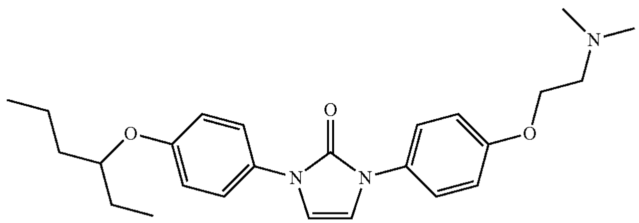 | 1-[4-(2-Dimethylaminoethoxy)phenyl]-3-[4-(1-ethylbutoxy)phenyl]-1,3-dihydroimidazol-2-one | C25H33N3O3 | 423.56 | 424 |
| 121 | 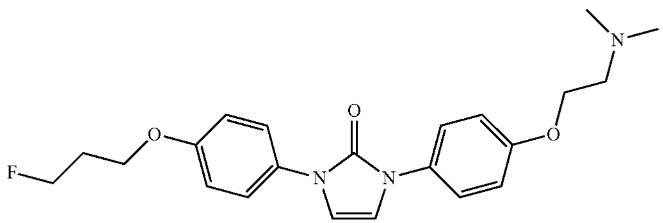 | 1-[4-(2-Dimethylaminoethoxy)phenyl]-3-[4-(3-fluoropropoxy)phenyl]-1,3-dihydroimidazol-2-one | C22H26FN3O3 | 399.47 | 400 |
| 122 | 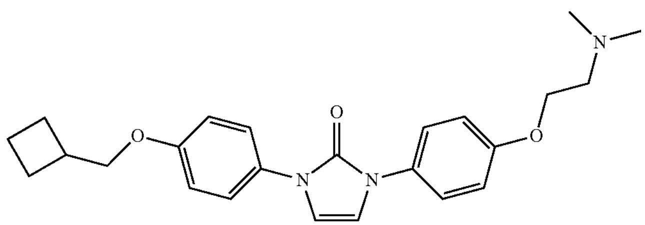 | 1-(4-Cyclobutylmethoxyphenyl)-3-[4-(2-dimethylaminoethoxy)phenyl]-1,3-dihydroimidazol-2-one | C24H29N3O3 | 407.52 | 408 |
| 123 | 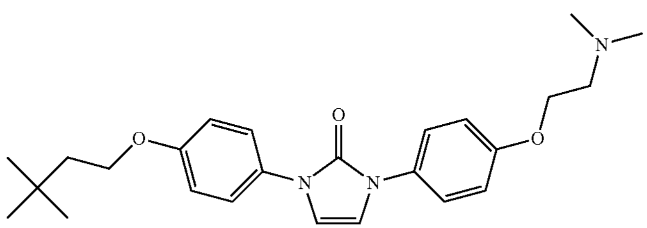 | 1-[4-(2-Dimethylaminoethoxy)phenyl]-3-[4-(3,3-dimethylbutoxy)phenyl]-1,3-dihydroimidazol-2-one | C25H33N3O3 | 423.56 | 424 |

TABLE 3-continued

| Ex. No. | Structure | Name | Molecular formula | Molecular weight | [M + H]+ ESI-MS |
|---|---|---|---|---|---|
| 124 | 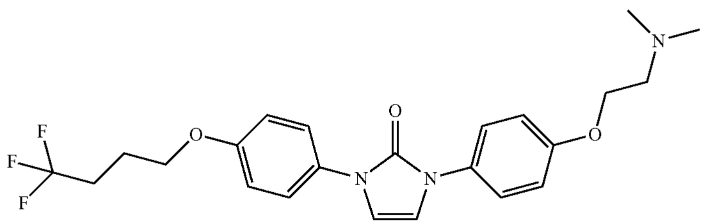 | 1-[4-(2-Dimethylaminoethoxy)phenyl]-3-[4-(4,4,4-trifluorobutoxy)phenyl]-1,3-dihydroimidazol-2-one | C23H26F3N3O3 | 449.48 | 450 |
| 125 | 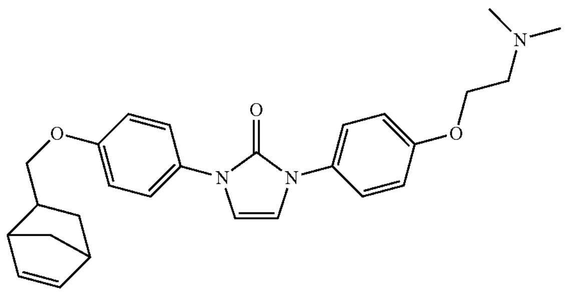 | 1-[4-(Bicyclo[2.2.1]hept-5-en-2-ylmethoxy)phenyl]-3-[4-(2-dimethylaminoethoxy)phenyl]-1,3-dihydroimidazol-2-one | C27H31N3O3 | 445.57 | 446 |
| 126 | 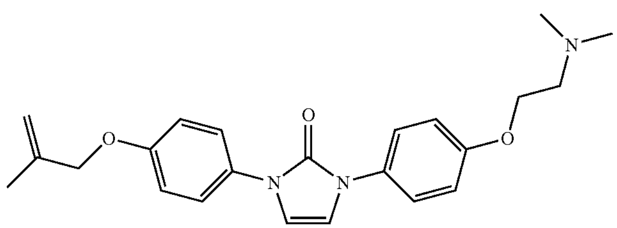 | 1-[4-(2-Dimethylaminoethoxy)phenyl]-3-[4-(2-methylallyloxy)phenyl]-1,3-dihydroimidazol-2-one | C23H27N3O3 | 393.49 | 394 |
| 127 | 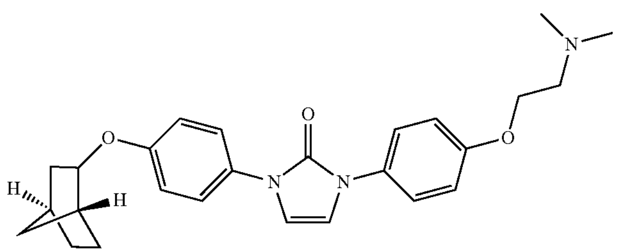 | 1-[4-((1S,2R,4R)-Bicyclo[2.2.1]hept-2-yloxy)phenyl]-3-[4-(2-dimethylaminoethoxy)phenyl]-1,3-dihydroimidazol-2-one | C26H31N3O3 | 433.56 | 434 |

TABLE 3-continued

| Ex. No. | Structure | Name | Molecular formula | Molecular weight | [M + H]+ ESI-MS |
|---|---|---|---|---|---|
| 128 | 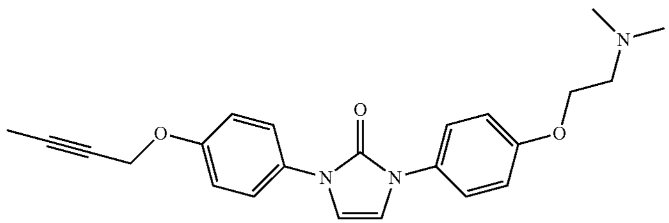 | 1-(4-But-2-ynyloxyphenyl)-3-[4-(2-dimethylaminoethoxy)phenyl]-1,3-dihydroimidazol-2-one | C23H25N3O3 | 391.47 | 392 |
| 129 | 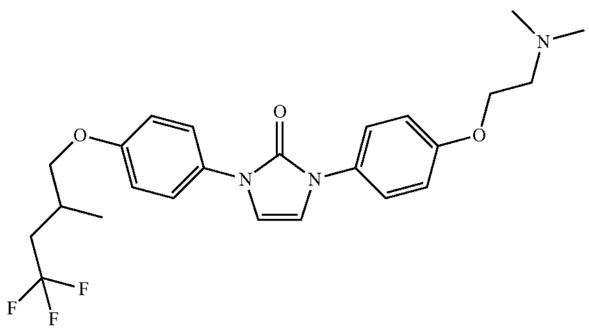 | 1-[4-(2-Dimethylaminoethoxy)phenyl]-3-[4-(4,4,4-trifluoro-2-methylbutoxy)phenyl]-1,3-dihydroimidazol-2-one | C24H28F3N3O3 | 463.50 | 464 |
| 130 | 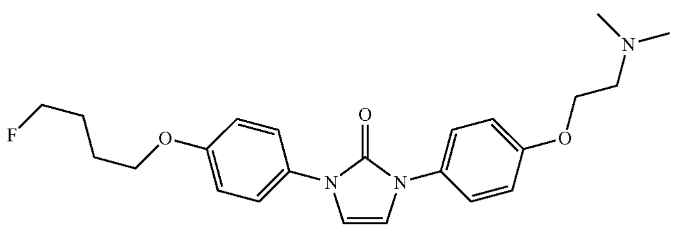 | 1-[4-(2-Dimethylaminoethoxy)phenyl]-3-[4-(4-fluorobutoxy)phenyl]-1,3-dihydroimidazol-2-one | C23H28FN3O3 | 413.50 | 414 |

EXAMPLE 131

1-[4-(2-Dimethylaminoethoxy)phenyl]-3-[4-(2-nitrophenoxy)phenyl]-1,3-dihydroimidazol-2-one

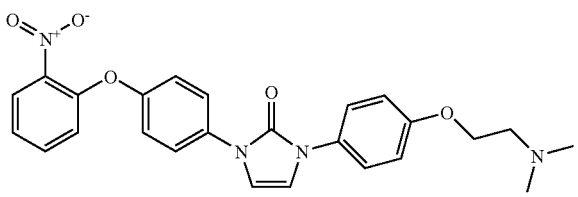

2-Nitrofluorobenzene (0.14 g) was added to a mixture of 1-[4-(2-dimethylaminoethoxy)phenyl]-3-(4-hydroxyphenyl)-1,3-dihydroimidazol-2-one (0.34 g), Aliquat® 336 (0.04 g, tricaprylylmethylammonium chloride), potassium hydroxide (0.077 g) and toluene (10 mL). The mixture was heated under reflux for 3 hours. After cooling, the reaction solution was washed with water, dried and concentrated. The residue was purified by preparative HPLC. The product with the molecular weight of 460.49 ($C_{25}H_{24}N_4O_5$); MS (ESI): 461 ([M+H]$^+$), was obtained as hydrotrifluoroacetate in this way.

EXAMPLE 132

1-[4-(2-Dimethylaminoethoxy)phenyl]-3-(4-o-tolyloxyphenyl)-1,3-dihydroimidazol-2-one

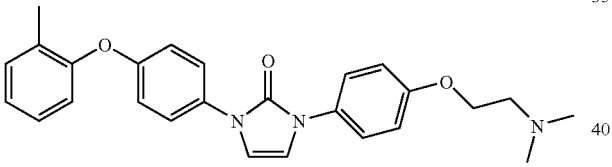

Carbonyldiimidazole (40 mg) was added to a solution of 4-o-tolyloxyphenylamine (50 mg) in dimethylformamide (2 mL) at 0° C. After 30 minutes, (2,2-dimethoxyethyl)-[4-(2-dimethylaminoethoxy)phenyl]amine (67 mg) was added, and the mixture was heated at 80° C. for 2 hours. After cooling to room temperature, trifluoroacetic acid (0.5 mL) was added and the mixture was left to stand for 72 hours. The reaction solution was diluted with ethyl acetate and washed with saturated sodium bicarbonate solution. The organic phase was dried and concentrated. The residue was purified by preparative HPLC. The product with the molecular weight of 429.52 ($C_{26}H_{27}N_3O_3$); MS (ESI): 430 ([M+H]$^+$), was obtained as hydrotrifluoroacetate in this way.

(2,2-Dimethoxyethyl)-[4-(2-dimethylaminoethoxy)phenyl]amine

Sodium hydride (1.57 g) was added to a solution of 4-(2,2-dimethoxyethyl-amino)phenol (4.3 g) in dimethylformamide (25 mL). After 30 minutes, 2-dimethylaminoethyl chloride (hydrochloride, 3.14 g) was added. After 12 hours, the reaction solution was diluted with ethyl acetate and washed with water. The organic phase was dried and concentrated. The residue was purified by MPLC (eluent: dichloromethane/methanol/ammonia solution 95:4.9:0.1). The product with the molecular weight of 268.36 ($C_{14}H_{24}N_2O_3$); MS (ESI): 269 ([M+H]$^+$), was obtained in this way.

4-(2,2-Dimethoxyethylamino)phenol

Palladium(II) hydroxide (20% on carbon, 0.5 g) was added to a solution of (4-benzyloxyphenyl)-(2,2-dimethoxyethyl)amine (3.5 g) in ethanol (50 mL) under nitrogen. The nitrogen atmosphere was replaced by hydrogen and the mixture was shaken for 3 hours. The catalyst was filtered off and the filtrate was concentrated. The crude product was reacted further without purification.

EXAMPLES 133–166

Further examples prepared as described in example 132 using the appropriate aniline are summarized in table 4.

TABLE 4

| Ex. No. | Name | Structure | Molecular formula | Molecular weight | [M + H]+ ESI |
|---|---|---|---|---|---|
| 133 | 1-[4-(2-Chlorophenoxy)phenyl]-3-[4-(2-dimethylaminoethoxy)phenyl]-1,3-dihydroimidazol-2-one | 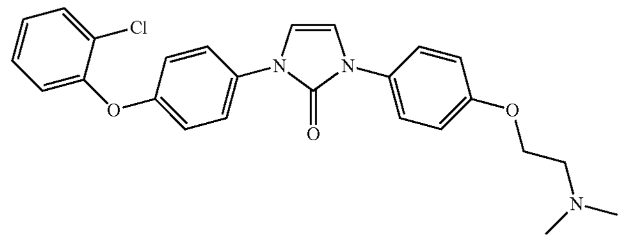 | C25H24ClN3O3 | 449.94 | 450 |
| 134 | 1-[4-(2-Dimethylaminoethoxy)phenyl]-3-[4-(2-methoxyphenoxy)phenyl]-1,3-dihydroimidazol-2-one | 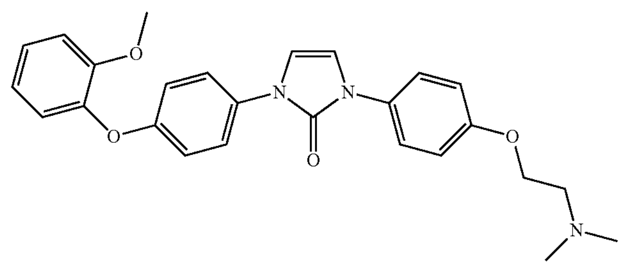 | C26H27N3O4 | 445.52 | 446 |
| 135 | 1-[4-(2-Dimethylaminoethoxy)phenyl]-3-(4-m-tolyloxyphenyl)-1,3-dihydroimidazol-2-one | 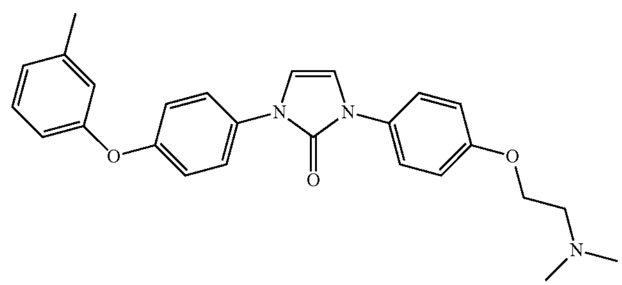 | C26H27N3O3 | 429.52 | 430 |

TABLE 4-continued

| Ex. No. | Name | Structure | Molecular formula | Molecular weight | [M + H]+ ESI |
|---|---|---|---|---|---|
| 136 | 1-[4-(3-Chlorophenoxy)phenyl]-3-[4-(2-dimethylaminoethoxy)phenyl]-1,3-dihydroimidazol-2-one | 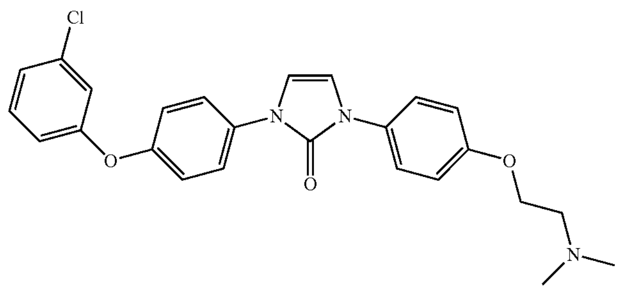 | C25H24ClN3O3 | 449.94 | 450 |
| 137 | 1-[4-(2-Dimethylaminoethoxy)phenyl]-3-[4-(3-methoxyphenoxy)phenyl]-1,3-dihydroimidazol-2-one | 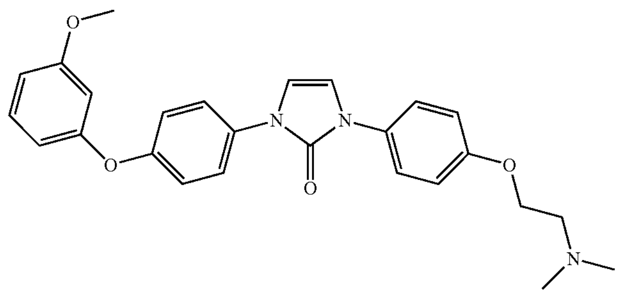 | C26H27N3O4 | 445.52 | 446 |
| 138 | 1-[4-(2-Dimethylaminoethoxy)phenyl]-3-[4-(pyridin-3-yloxy)phenyl]-1,3-dihydroimidazol-2-one | 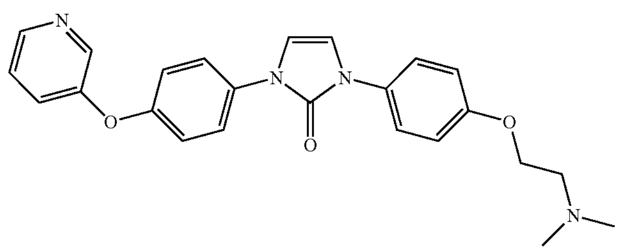 | C24H24N4O3 | 416.48 | 417 |

TABLE 4-continued

| Ex. No. | Name | Structure | Molecular formula | Molecular weight | [M + H]+ ESI |
|---|---|---|---|---|---|
| 139 | 1-Biphenyl-4-yl-3-[4-(2-dimethylaminoethoxy)phenyl]-1,3-dihydroimidazol-2-one | 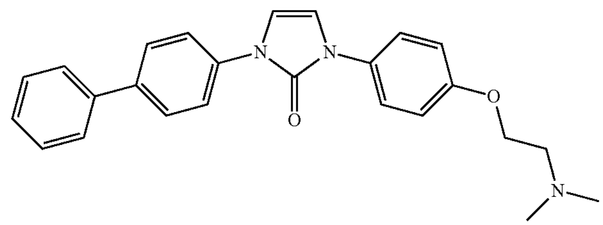 | C25H25N3O2 | 399.50 | 400 |
| 140 | 1-(4-Butylphenyl)-3-[4-(2-dimethylaminoethoxy)phenyl]-1,3-dihydroimidazol-2-one | 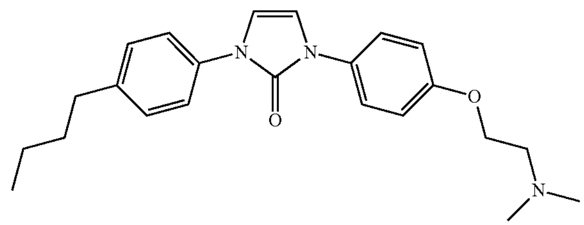 | C23H29N3O2 | 379.51 | 380 |
| 141 | 1-[4-(2-Dimethylaminoethoxy)phenyl]-3-(2-methoxy-4-phenylaminophenyl)-1,3-dihydroimidazol-2-one | 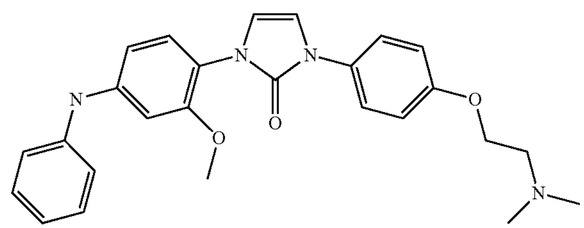 | C26H28N4O3 | 444.54 | 445 |
| 142 | 1-(4-Benzyloxyphenyl)-3-[4-(2-dimethylaminoethoxy)phenyl]-1,3-dihydroimidazol-2-one | 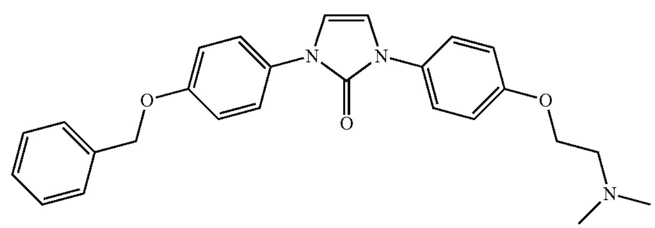 | C26H27N3O3 | 429.52 | 430 |

TABLE 4-continued

| Ex. No. | Name | Structure | Molecular formula | Molecular weight | [M + H]+ ESI |
|---|---|---|---|---|---|
| 143 | 1-(4-Benzylphenyl)-3-[4-(2-dimethylaminoethoxy)phenyl]-1,3-dihydroimidazol-2-one | 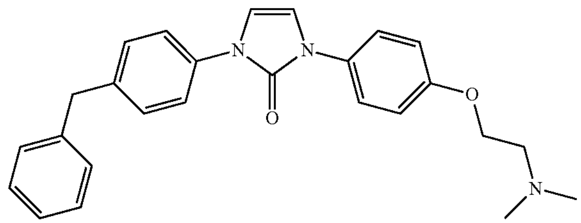 | C26H27N3O2 | 413.52 | 414 |
| 144 | 1-[4-(2-Dimethylaminoethoxy)phenyl]-3-(4-pyridin-4-ylmethylphenyl)-1,3-dihydroimidazol-2-one | 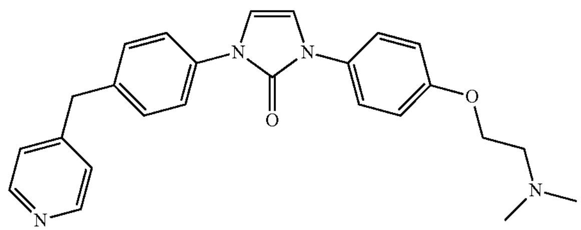 | C25H26N4O2 | 414.51 | 415 |
| 145 | 1-[4-(2-Dimethylaminoethoxy)phenyl]-3-(4-p-tolyloxyphenyl)-1,3-dihydroimidazol-2-one | 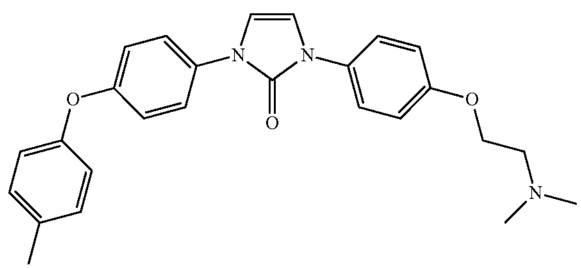 | C26H27N3O3 | 429.52 | 430 |
| 146 | 1-[4-(2-Dimethylaminoethoxy)phenyl]-3-(4-phenylsulfanylphenyl)-1,3-dihydroimidazol-2-one | 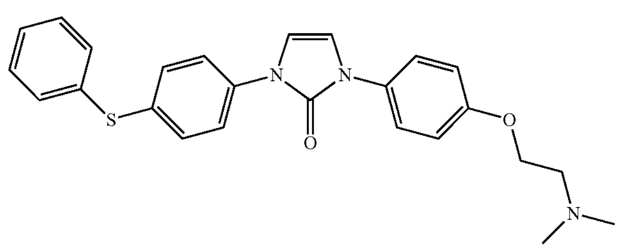 | C25H25N3O2S | 431.56 | 432 |

TABLE 4-continued

| Ex. No. | Name | Structure | Molecular formula | Molecular weight | [M + H]+ ESI |
|---|---|---|---|---|---|
| 147 | 1-{4-[2-Dimethylaminoethoxy)phenyl]-3-[4-(3-trifluoromethylphenoxy)phenyl]-1,3-dihydroimidazol-2-one | 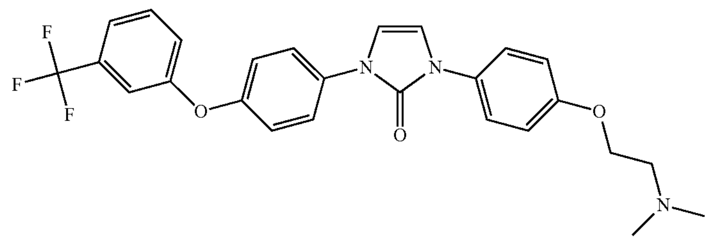 | C26H24F3N3O3 | 483.49 | 484 |
| 148 | 1-(4-Butyl-2-methylphenyl)-3-[4-(2-dimethylaminoethoxy)phenyl]-1,3-dihydroimidazol-2-one | 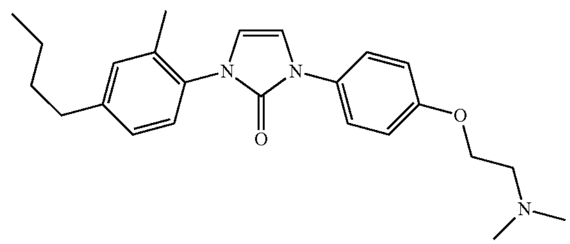 | C24H31N3O2 | 393.53 | 394 |
| 149 | 4'-{3-[4-(2-Dimethylaminoethoxy)phenyl]-2-oxo-2,3-dihydroimidazol-1-yl}biphenyl-4-carbonitrile | 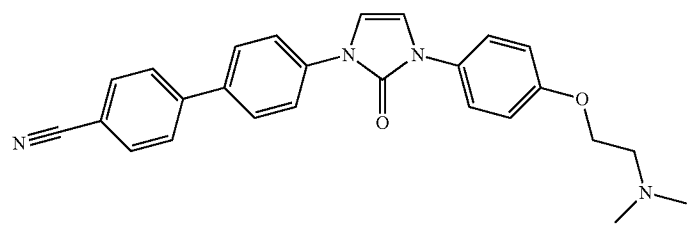 | C26H24N4O2 | 424.51 | 425 |
| 150 | 1-[3-Chloro-4-(pyrimidin-2-yloxy)phenyl]-3-[4-(2-dimethylaminoethoxy)phenyl]-1,3-dihydroimidazol-2-one | 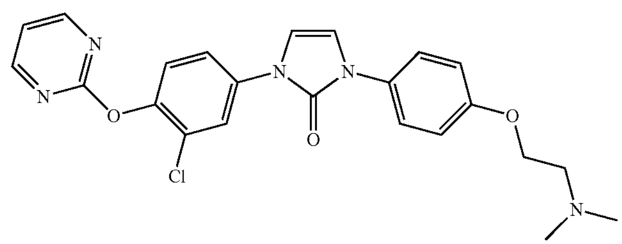 | C23H22ClN5O3 | 451.92 | 452 |

TABLE 4-continued

| Ex. No. | Name | Structure | Molecular formula | Molecular weight | [M + H]+ ESI |
|---|---|---|---|---|---|
| 151 | 5-(4-[3-[4-(2-Dimethylaminoethoxy)phenyl]-2-oxo-2,3-dihydroimidazol-1-yl]phenyl)-2-methylfuran-3-carboxylic acid ethyl ester | 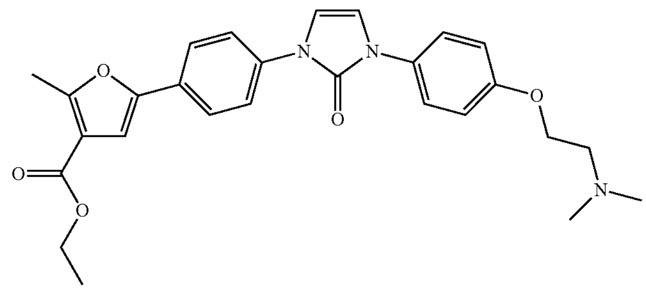 | C27H29N3O5 | 475.55 | 476 |
| 152 | 1-[4-(2-Dimethylaminoethoxy)phenyl]-3-[4-(piperidine-1-carbonyl)phenyl]-1,3-dihydroimidazol-2-one | 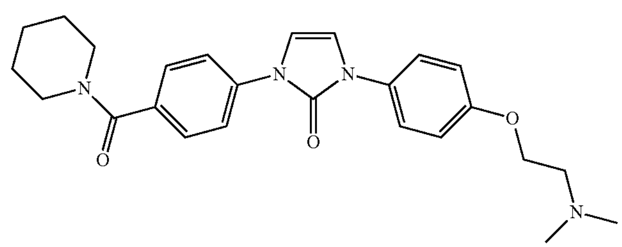 | C25H30N4O3 | 434.54 | 435 |
| 153 | 1-[4-(2-Dimethylaminoethoxy)phenyl]-3-(4-heptafluoropropylsulfanylphenyl)-1,3-dihydroimidazol-2-one | 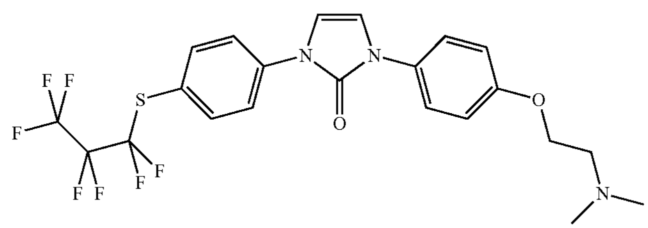 | C22H20F7N3O2S | 523.48 | 524 |
| 154 | 1-[4-(2-Dimethylaminoethoxy)phenyl]-3-[4-(4-fluorophenoxy)phenyl]-1,3-dihydroimidazol-2-one | 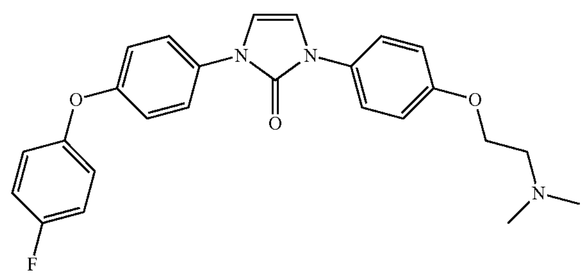 | C25H24FN3O3 | 433.49 | 434 |

TABLE 4-continued

| Ex. No. | Name | Structure | Molecular formula | Molecular weight | [M + H]+ ESI |
|---|---|---|---|---|---|
| 155 | 1-[4-(2-Dimethylaminoethoxy)phenyl]-3-[4-(pyrimidin-2-yloxy)phenyl]-1,3-dihydroimidazol-2-one | 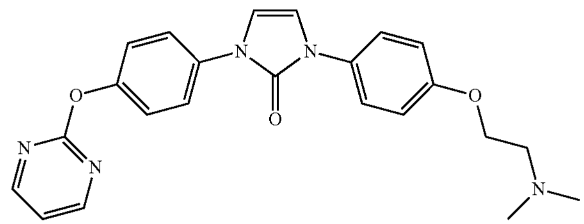 | C23H23N5O3 | 417.47 | 418 |
| 156 | 1-[4-(2-Dimethylaminoethoxy)phenyl]-3-(2-methoxybiphenyl-4-yl)-1,3-dihydroimidazol-2-one | 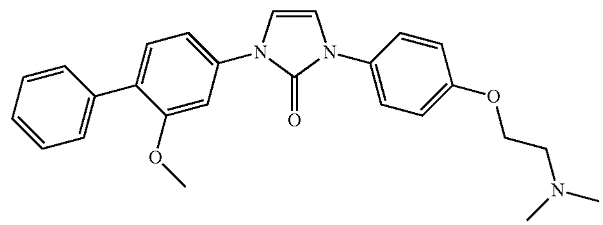 | C26H27N3O3 | 429.52 | 430 |
| 157 | 1-[4-(2-Dimethylaminoethoxy)phenyl]-3-(6-methoxybiphenyl-3-yl)-1,3-dihydroimidazol-2-one | 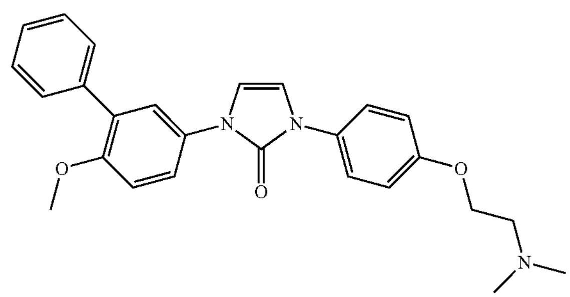 | C26H27N3O3 | 429.52 | 430 |
| 158 | 1-[4-(2-Dimethylaminoethoxy)phenyl]-3-{4-[1,3]dithiolan-2-ylphenyl}-1,3-dihydroimidazol-2-one | 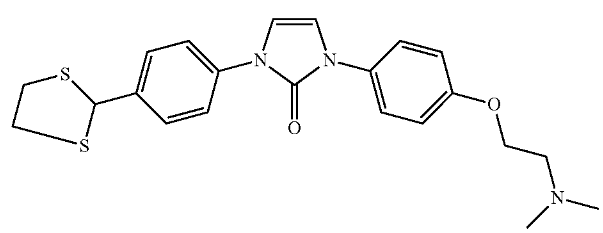 | C22H25N3O2S2 | 427.59 | 428 |

TABLE 4-continued

| Ex. No. | Name | Structure | Molecular formula | Molecular weight | [M + H]+ ESI |
|---|---|---|---|---|---|
| 159 | 1-[4-(2-Dimethylaminoethoxy)phenyl]-3-[4-(thiophen-2-ylsulfanyl)phenyl]-1,3-dihydroimidazol-2-one | 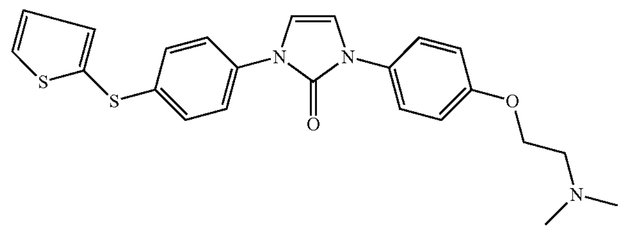 | C23H23N3O2S2 | 437.59 | 438 |
| 160 | 1-(3-Chloro-4-piperidin-1-ylphenyl)-3-[4-(2-dimethylaminoethoxy)phenyl]-1,3-dihydroimidazol-2-one | 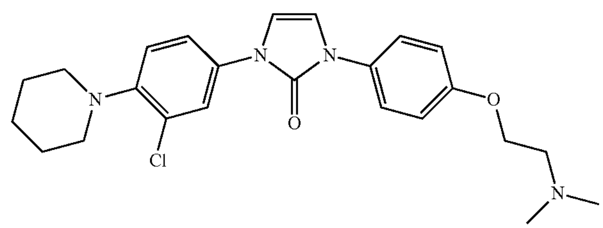 | C24H29ClN4O2 | 440.98 | 441 |
| 161 | 1-[4-(2-Dimethylaminoethoxy)phenyl]-3-[4-(2-fluorophenoxy)phenyl]-1,3-dihydroimidazol-2-one | 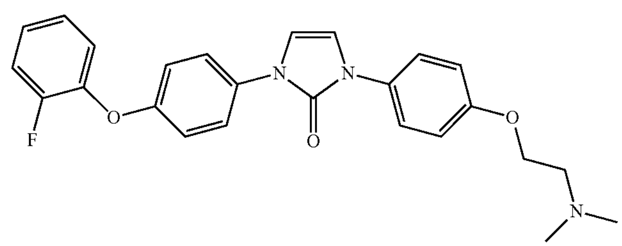 | C25H24FN3O3 | 433.49 | 434 |

TABLE 4-continued

| Ex. No. | Name | Structure | Molecular formula | Molecular weight | [M + H]+ ESI |
|---|---|---|---|---|---|
| 162 | 1-(3-Cyclopentyloxy-4-methoxyphenyl)-3-[4-(2-dimethylaminoethoxy)phenyl]-1,3-dihydroimidazol-2-one | 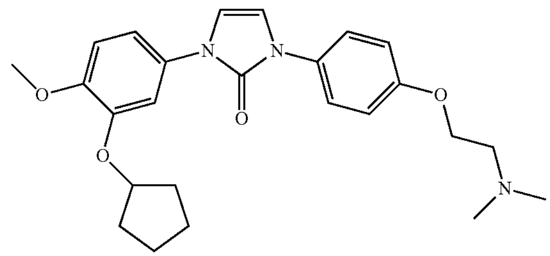 | C25H31N3O4 | 437.54 | 438 |
| 163 | 1-[4-(2-Dimethylaminoethoxy)phenyl]-3-(4-piperidin-1-ylphenyl)-1,3-dihydroimidazol-2-one | 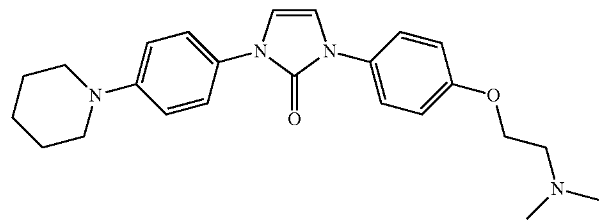 | C24H30N4O2 | 406.53 | 407 |

EXAMPLE 164

1-(4-Cyclopentyloxyphenyl)-3-{4-[(2-hydroxyethyl)methylamino]phenyl}-1,3-dihydroimidazol-2-one

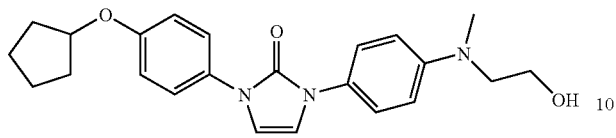

A solution of 1-(4-cyclopentyloxyphenyl)-1-(2,2-dimethoxyethyl)-3-{4-[(2-hydroxyethyl)methylamino]phenyl}urea (0.4 g) in dimethyl-formamide (6 mL) was mixed with trifluoroacetic acid (2 mL) and left to stand for 48 hours. The mixture was diluted with water and extracted with ethyl acetate. The organic phase was washed with water and sodium carbonate solution, dried and concentrated. The product with the molecular weight of 393.49 ($C_{23}H_{27}N_3O_3$); MS (ESI): 394 ([M+H]$^+$), was obtained in this way.

1-(4-Cyclopentyloxyphenyl)-1-(2,2-dimethoxyethyl)-3-{4-[(2-hydroxyethyl)-methylamino]phenyl}urea 2-[(4-Aminophenyl)methylamino]ethanol was reacted with carbonyldiimidazole and (4-cyclopentyloxyphenyl)-(2,2-dimethoxyethyl)amine by the method given in example 4. The crude product was purified by chromatography on silica gel (eluent: ethyl acetate). The product with the molecular weight of 457.57 ($C_{25}H_{35}N_3O_5$); MS (ESI): 458 ([M+H]$^+$), was obtained in this way.

2-[(4-Aminophenyl)methylamino]ethanol

Palladium (10% on carbon, 1 g) was added to a solution of 2-[methyl-(4-nitrophenyl)amino]ethanol (6 g) in methanol (100 mL) under nitrogen. The nitrogen atmosphere was replaced by hydrogen and the mixture was shaken for 4 hours. The catalyst was filtered off and the filtrate was concentrated. The product with the molecular weight of 166.22 ($C_9H_{14}N_2O$); MS (ESI):167 ([M+H]$^+$), was obtained in this way.

2-[Methyl-(4-nitrophenyl)amino]ethanol

A mixture of 4-fluoronitrobenzene (20 g) and 2-methylaminoethanol (56 mL) was left to stand for 12 hours and then diluted with ethyl acetate. It was washed with water. The organic phase was dried and concentrated. The product with the molecular weight of 196.21 ($C_9H_{12}N_2O_3$); MS (ESI):197 ([M+H]$^+$), was obtained in this way.

EXAMPLE 165

1-(4-Cyclopentyloxyphenyl)-3-{4-[(2-imidazol-1-ylethyl)methylamino]-phenyl}-1,3-dihydroimidazol-2-one

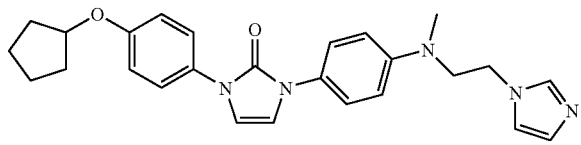

Triethylamine (0.13 g) and methanesulfonyl chloride (0.1 mL) were added to a solution of 1-(4-cyclopentyloxyphenyl)-3-{4-[(2-hydroxyethyl)methyl-amino]phenyl}-1,3-dihydroimidazol-2-one (0.20 g) in dichloromethane (5 mL) at 0° C. After 2 hours, volatiles were removed and the residue was taken up in propionitrile (5 mL). Imidazole (0.25 g) was added and the mixture was heated at 90° C. for 6 hours. Volatiles were removed and the residue was purified by preparative HPLC. The product with the molecular weight of 443.55 ($C_{26}H_{29}N_5O_2$); MS (ESI): 444 ([M+H]$^+$), was obtained as hydrotrifluoroacetate in this way.

EXAMPLE 166

1-(4-Cyclopentyloxyphenyl)-3-(4-{methyl-[2-(2-methylimidazol-1-yl)ethyl]-amino}phenyl)-1,3-dihydroimidazol-2-one

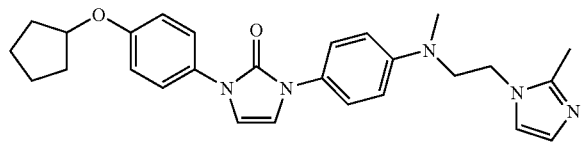

The compound was prepared as described in example 165 but with use of 2-methylimidazole. The product with the molecular weight of 457.58 ($C_{27}H_{31}N_5O_2$); MS (ESI): 458 ([M+H]$^+$), was obtained as hydrotrifluoro-acetate in this way.

EXAMPLE 167

1-(4-Cyclopentyloxyphenyl)-3-{4-[methyl-(2-methylaminoethyl)amino]-phenyl}-1,3-dihydroimidazol-2-one

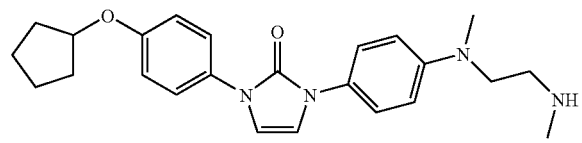

The compound was prepared as described in example 165 but with use of methylamine (1 M in THF). The product with the molecular weight of 406.53 ($C_{24}H_{30}N_4O_2$); MS (ESI): 407 ([M+H]$^+$), was obtained as hydrotrifluoroacetate in this way.

EXAMPLE 168

1-(4-Cyclopentyloxyphenyl)-3-{4-[methyl-(2-piperidin-1-ylethyl)amino]-phenyl}-1,3-dihydroimidazol-2-one

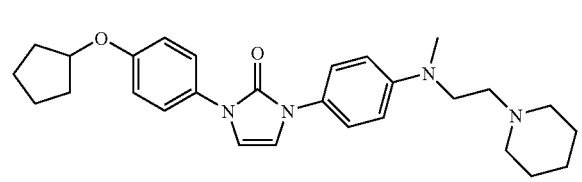

The compound was prepared as described in example 165 but with use of piperidine. The product with the molecular weight of 460.62 ($C_{28}H_{36}N_4O_2$); MS (ESI): 461 ([M+H]$^+$), was obtained as hydrotrifluoroacetate in this way.

EXAMPLE 169

1-(4-Cyclopentyloxyphenyl)-3-(4-{[2-(cyclopropyl-methylamino)ethyl]methylamino}phenyl)-1,3-dihydroimidazol-2-one

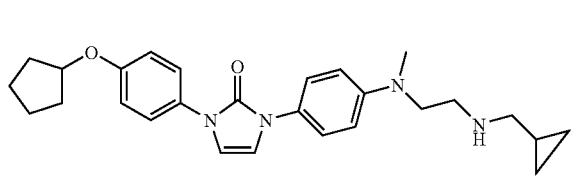

The compound was prepared as described in example 165 but with use of cyclopropylmethylamine. The product with the molecular weight of 446.60 ($C_{27}H_{34}N_4O_2$); MS (ESI): 447 ($[M+H]^+$), was obtained as hydrotrifluoro-acetate in this way.

EXAMPLE 170

N-[2-({4-[3-(4-Cyclopentyloxyphenyl)-2-oxo-2,3-dihydroimidazol-1-yl]-phenyl}methylamino)ethyl]-N-methylacetamide

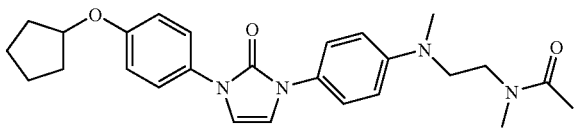

A solution of 1-(4-cyclopentyloxyphenyl)-3-{4-[methyl-(2-methylaminoethyl)-amino]phenyl}-1,3-dihydroimidazol-2-one (50 mg) in dichloromethane (2 mL) was mixed with triethylamine (25 mg) and acetyl chloride (15 mg). After 2 hours, volatiles were removed and the residue was purified by preparative HPLC. The product with the molecular weight of 448.57 ($C_{26}H_{32}N_4O_3$); MS (ESI): 449 ($[M+H]^+$), was obtained as hydrotrifluoro-acetate in this way.

EXAMPLE 171

1-[4-(2-Dimethylaminoethoxy)phenyl]-3-(4-phenoxyphenyl)imidazolidin-2-one

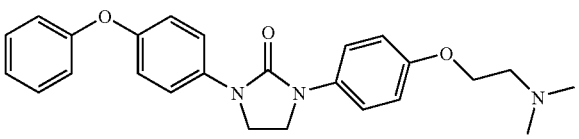

Palladium(II) hydroxide (20 mg) was added to a solution of 1-(4-(2-dimethylaminoethoxy)phenyl)-3-(4-phenoxyphenyl)-1,3-dihydroimidazol-2-one (50 mg) in ethanol (5 mL) under nitrogen. The nitrogen atmosphere was replaced by hydrogen and the mixture was shaken for 8 hours. The catalyst was filtered off and the filtrate was concentrated. The product with the molecular weight of 417.51 ($C_{25}H_{27}N_3O_3$); MS (ESI): 418 ($[M+H]^+$), was obtained in this way.

EXAMPLE 172

1-(4-Cyclopropylmethoxyphenyl)-3-[4-(2-dimethylaminoethoxy)phenyl]-imidazolidin-2-one

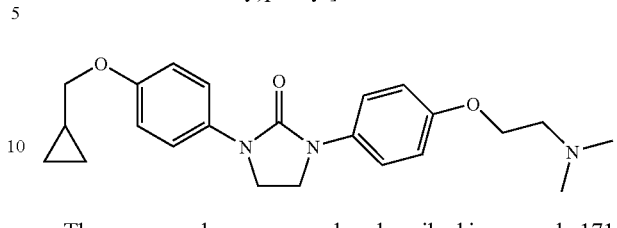

The compound was prepared as described in example 171 by hydrogenation of 1-(4-cyclopropylmethoxyphenyl)-3-[4-(2-dimethylamino-ethoxy)phenyl]-1,3-dihydroimidazol-2-one. The product with the molecular weight of 395.51 ($C_{23}H_{29}N_3O_3$); MS (ESI): 396 ($[M+H]^+$), was obtained in this way.

EXAMPLE 173

1-[4-(2-Dimethylaminoethoxy)phenyl]-3-(4-phenoxyphenyl)-[1,3]-diazepan-2-one

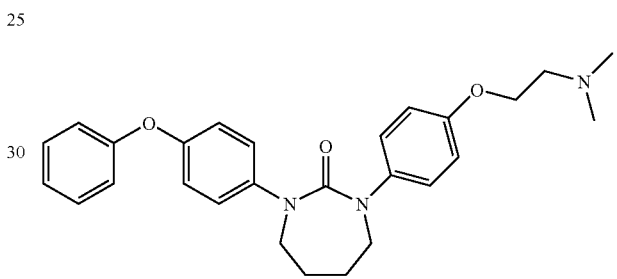

A solution of 1-(4-hydroxyphenyl)-3-(4-phenoxyphenyl)-[1,3]-diazepan-2-one (26 mg) was dissolved in THF (2 mL), and sodium hydride (80% in oil, 3 mg) was added. After 30 minutes, 2-dimethylaminoethyl chloride (hydrochloride, 11 mg) was added. After 16 hours, the reaction mixture was diluted with water and extracted with ethyl acetate. The organic phase was dried and concentrated. The residue was purified by preparative HPLC. The product with the molecular weight of 445.57 ($C_{27}H_{31}N_3O_3$); MS (ESI): 446 ($[M+H]^+$), was obtained in this way.

1-(4-Hydroxyphenyl)-3-(4-phenoxyphenyl)-[1,3]-diazepan-2-one

The compound was prepared by hydrogenation of 1-(4-benzyloxyphenyl)-3-(4-phenoxyphenyl)-1,3,4,7-tetrahydro[1,3]diazepin-2-one in analogy to the method in example 171. The product with the molecular weight of 374.44 ($C_{23}H_{22}N_2O_3$); MS (ESI): 375 ($[M+H]^+$), was obtained in this way.

1-(4-Benzyloxyphenyl)-3-(4-phenoxyphenyl)-1,3,4,7-tetrahydro-[1,3]-diazepin-2-one The Grubbs catalyst was added to a solution of 1,3-diallyl-3-(4-benzyloxyphenyl)-1-(4-phenoxyphenyl)urea (145 mg) in dichloro-methane (2 mL) at 0° C. After 3 days at room temperature, volatiles were removed and the residue was purified by preparative HPLC. The product with the molecular weight of 462.55 ($C_{30}H_{26}N_2O_3$); MS (ESI): 463 ($[M+H]^+$), was obtained in this way.

1,3-Diallyl-3-(4-benzyloxyphenyl)-1-(4-phenoxyphenyl)urea

Potassium hydride (30% in oil, 40 mg) was added to a solution of 1-allyl-1-(4-benzyloxyphenyl)-3-(4-phenoxyphenyl)urea (133 mg) in THF (3 mL) at −78° C. After 30 minutes, allyl bromide (30 μL) was added. After 14 hours at room temperature, the solution was diluted with dichloromethane and washed with saturated sodium bicarbonate solution. The organic phase was dried and concentrated. The product with the molecular weight of 490.61 ($C_{32}H_{30}N_2O_3$); MS (ESI): 491 ([M+H]$^+$), was obtained in this way.

1-Allyl-1-(4-benzyloxyphenyl)-3-(4-phenoxyphenyl)urea

Carbonyldiimidazole (136 mg) was added to a solution of 4-phenoxyaniline (155 mg) in dimethylformamide (3 mL) at 0° C. After 30 minutes, allyl-(4-benzyloxyphenyl)amine (200 mg) was added and the temperature was increased to 80° C. for 2 hours. A further 2 hours at 120° C., the reaction solution was cooled and then purified by preparative HPLC. The product with the molecular weight of 450.54 ($C_{29}H_{26}N_2O_3$); MS (ESI): 451 ([M+H]$^+$), was obtained in this way.

Allyl-(4-benzyloxyphenyl)amine

A mixture of 4-benzyloxyaniline (3.0 g), allyl bromide (1.27 mL), potassium carbonate (4.2 g) and dimethylformamide (15 mL) was heated at 80° C. for 3 hours. After cooling, the reaction solution was filtered and concentrated. The residue was purified by MPLC. The product with the molecular weight of 239.32 ($C_{16}H_{17}NO$); MS (ESI):240 ([M+H]$^+$), was obtained in this way.

EXAMPLE 174

4-[4-(2-Dimethylaminoethoxy)phenyl]-2-(4-phenoxyphenyl)-2,4-dihydro-[1,2,4]triazol-3-one

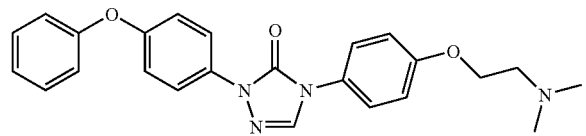

1-Formyl-2-(4-phenoxyphenyl)-4-[4-(2-dimethylaminoethoxy)phenyl]semicarbazide (60 mg) was added to a solution of potassium hydroxide (15 mg) in methanol (20 mL). After 4 hours at room temperature, the mixture was heated at 40° C. for 24 hours. After cooling, the reaction solution was diluted with water and extracted with ethyl acetate. The organic phase was dried and concentrated. The product with the molecular weight of 416.48 ($C_{24}H_{24}N_4O_3$); MS (ESI): 417 ([M+H]$^+$), was obtained in this way.

1-Formyl-2-(4-phenoxyphenyl)-4-[4-(2-dimethylaminoethoxy)phenyl]semicarbazide Palladium(II) hydroxide (60 mg) and formic acid (4.6 g) were added to a solution of 1-benzylidene-2-(4-phenoxyphenyl)-4-[4-(2-dimethylamino-ethoxy)phenyl]semicarbazide (600 mg) in tetrahydrofuran/ethanol (1:1, 30 mL). The mixture was heated under reflux for five hours and then filtered. The filtrate was concentrated and the residue was purified by HPLC. The product with the molecular weight of 434.50 ($C_{24}H_{26}N_4O_4$); MS (ESI): 435 ([M+H]$^+$), was obtained in this way.

1-Benzylidene-2-(4-phenoxyphenyl)-4-[4-(2-dimethylaminoethoxy)phenyl]-semicarbazide Phosgene (20% in toluene; 0.091 mL) was added dropwise to a solution of N-benzylidene-N'-(4-phenoxyphenyl)hydrazine (50 mg) in toluene (1 mL) at 0° C. After 24 hours at room temperature, 4-(2-dimethylaminoethoxy)aniline (31 mg) was added. After two hours, the crystals which had separated out were filtered off with suction. The product with the molecular weight of 494.60 ($C_{30}H_{30}N_4O_3$); MS (ESI): 495 ([M+H]$^+$), was obtained in this way.

N-Benzylidene-N'-(4-phenoxyphenyl)hydrazine

A suspension of (4-phenoxyphenyl)hydrazine (J. Org. Chem. 1956, 395; 1.5 g) in methanol (10 mL) was mixed with benzaldehyde (0.76 mL) and heated to reflux. The crystals which separated out on cooling were filtered off with suction. The product with the molecular weight of 288.35 ($C_{19}H_{16}N_2O$); MS (ESI): 289 ([M+H]$^+$), was obtained in this way.

EXAMPLE 175

1-(4-Cyclopentyloxyphenyl)-3-[4-(2-methylaminoethoxy)phenyl]-1,3-dihydroimidazol-2-one

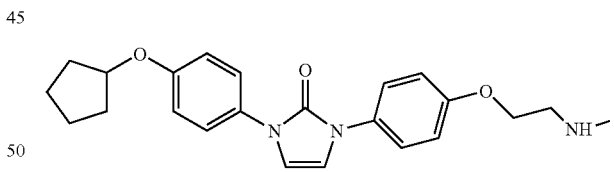

1-[4-(2-Bromoethoxy)phenyl]-3-(4-cyclopentyloxyphenyl)-1,3-dihydroimidazol-2-one was reacted with methylamine as described in example 6. The product with the molecular weight of 393.49 ($C_{23}H_{27}N_3O_3$); MS (ESI): 394 ([M+H]$^+$) was obtained in this way.

1-[4-(2-Bromoethoxy)phenyl]-3-(4-cyclopentyloxyphenyl)-1,3-dihydroimidazol-2-one 1-(4-Cyclopentyloxyphenyl)-3-(4-hydroxyphenyl)-1,3-dihydroimidazol-2-one was reacted with 1,2-dibromoethane as described in example 5. The product with the molecular weight of 443.34 ($C_{22}H_{23}BrN_2O_3$); MS (ESI): 443 ([M+H]$^+$) was obtained in this way.

1-(4-Cyclopentyloxyphenyl)-3-(4-hydroxyphenyl)-1,3-dihydroimidazol-2-one 3-(4-Benzyloxyphenyl)-1-(4-cyclopentyloxyphenyl)-1-(2,2-dimethoxyethyl)-urea was reacted first with hydrogen and then with TFA as described in example 92. The product with the molecular weight of 336.39 ($C_{20}H_{20}N_2O_3$); MS (ESI): 337 ([M+H]$^+$) was obtained in this way.

3-(4-Benzyloxyphenyl)-1-(4-cyclopentyloxyphenyl)-1 (2,2-dimethoxyethyl-urea (4-Cyclopentyloxyphenyl)-(2,2-dimethoxyethyl)amine was reacted with carbonyldiimidazole and 4-benzyloxyaniline as described in example 5. The product with the molecular weight of 490.60 ($C_{29}H_{34}N_2O_5$); MS (ESI): 491 ([M+H]$^+$) was obtained in this way.

EXAMPLE 176

N-(2-{4-[3-(4-Cyclopentyloxyphenyl)-2-oxo-2,3-dihydroimidazol-1-yl)-phenoxy}ethyl)-N-methylacetamide

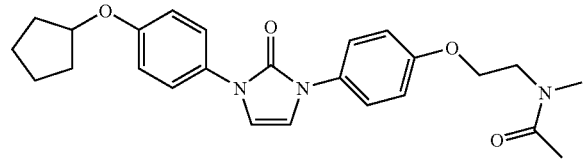

1-(4-Cyclopentyloxyphenyl)-3-[4-(2-methylaminoethoxy)phenyl]-1,3-dihydroimidazol-2-one was reacted with acetyl chloride and triethylamine as described in example 170. The product with the molecular weight of 435.53 ($C_{25}H_{29}N_3O_4$); MS (ESI): 436 ([M+H]$^+$) was obtained in this way.

EXAMPLE 177

1-(4-Cyclopentyloxyphenyl)-3-[4-(2-[1,2,4]triazol-4-ylethoxy)phenyl]-1,3-dihydroimidazol-2-one

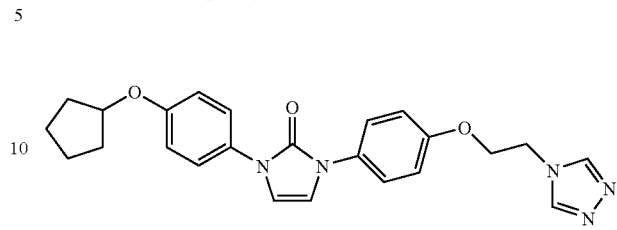

1-[4-(2-Bromoethoxy)phenyl]-3-(4-cyclopentyloxyphenyl)-1,3-dihydroimidazol-2-one was reacted with 1,2,4-triazole as described in example 5. The product with the molecular weight of 431.50 ($C_{24}H_{25}N_5O_3$); MS (ESI): 432 ([M+H]$^+$) was obtained in this way.

EXAMPLE 178

1-(4-Cyclopentyloxyphenyl)-3-{4-[2-(cyclopropylmethyl(methyl)amino)-ethoxy]phenyl}-1,3-dihydroimidazol-2-one

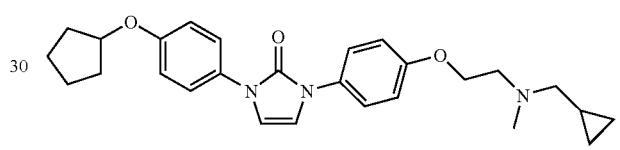

1-[4-(2-Bromoethoxy)phenyl]-3-(4-cyclopentyloxyphenyl)-1,3-dihydroimidazol-2-one was reacted with cyclopropylmethyl(methyl)amine as described in example 5. The product with the molecular weight of 447.58 ($C_{27}H_{33}N_3O_3$); MS (ESI): 448 ([M+H]$^+$) was obtained in this way.

EXAMPLES 179–216

Further examples were obtained by reacting 1-[4-(2-bromoethoxy)phenyl]-3-(4-cyclopentyloxyphenyl)-1,3-dihydroimidazol-2-one with the appropriate amines. The results are summarized in table 5.

TABLE 5

| Ex. No. | Name | Structure | Molecular formula | Molecular weight |
|---|---|---|---|---|
| 179 | 1-(4-Cyclopentyloxyphenyl)-3-{4-[2-(2-methoxyethylamino)ethoxy]phenyl}-1,3-dihydroimidazol-2-one | 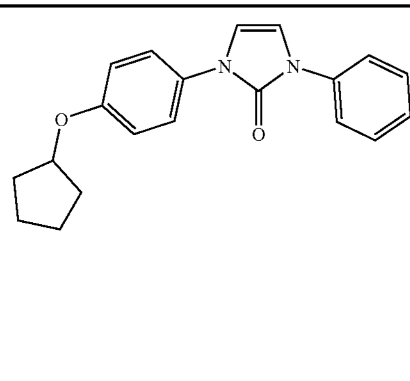 | C25H31N3O4 | 437.54 |

TABLE 5-continued

| Ex. No. | Name | Structure | Molecular formula | Molecular weight |
|---|---|---|---|---|
| 180 | 1-(4-Cyclopentyloxyphenyl)-3-(4-{2-[(1-hydroxycyclohexylmethyl)amino]ethoxy}phenyl)-1,3-dihydroimidazol-2-one | 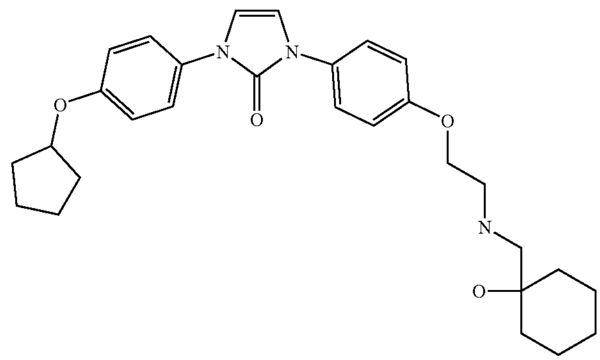 | C29H37N3O4 | 491.64 |
| 181 | 1-{4-[2-(4-Acetylpiperazin-1-yl)ethoxyphenyl}-3-(4-cyclopentyloxyphenyl)-1,3-dihydroimidazol-2-one | 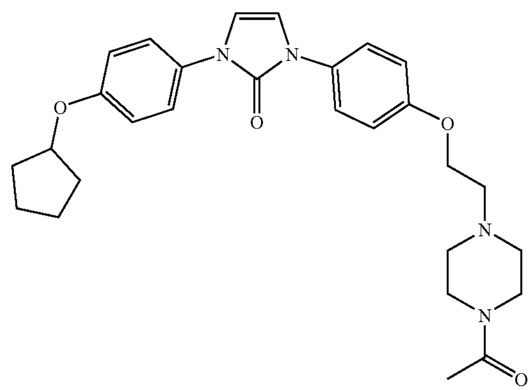 | C28H34N4O4 | 490.61 |
| 182 | 1-(4-Cyclopentyloxyphenyl)-3-{4-[2-(4-hydroxypiperidin-1-yl)ethoxy]phenyl)-1,3-dihydroimidazol-2-one | 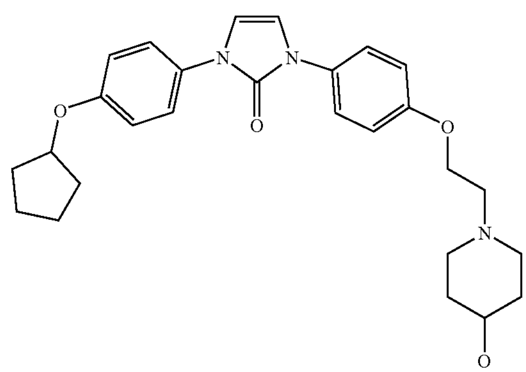 | C27H33N3O4 | 463.58 |
| 183 | 1-(4-Cyclopentyloxyphenyl)-3-{4-[2-(4-methylpiperidin-1-yl)ethoxy]phenyl}-1,3-dihydroimidazol-2-one | 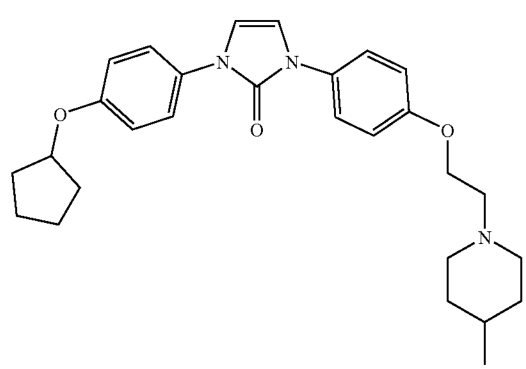 | C28N35N3O3 | 461.61 |

TABLE 5-continued

| Ex. No. | Name | Structure | Molecular formula | Molecular weight |
|---|---|---|---|---|
| 184 | 1-(4-Cyclopentyloxyphenyl)-3-[4-(2-cyclopropylaminoethoxy)phenyl]-1,3-dihydroimidazol-2-one | 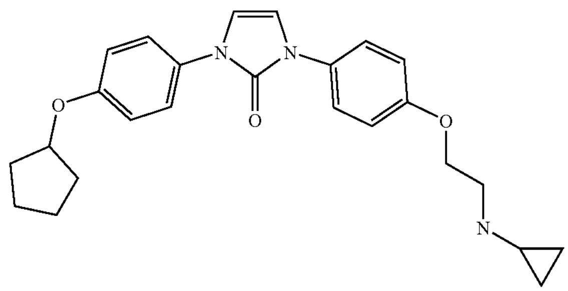 | C25H29N3O3 | 419.53 |
| 185 | 1-[4-(2-Cyclohexylaminoethoxy)phenyl]-3-(4-cyclopentyloxyphenyl)-1,3-dihydroimidazol-2-one | 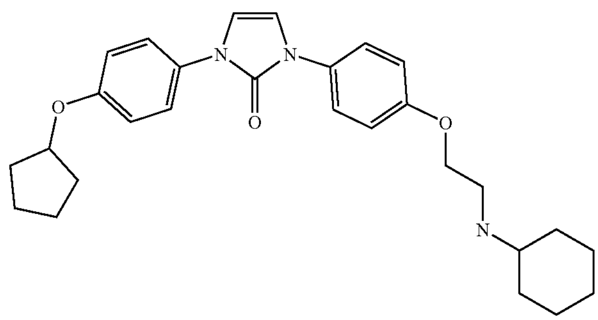 | C28H35N3O3 | 461.61 |
| 186 | 1-(4-Cyclopentyloxyphenyl)-3-[4-(2-isopropylaminoethoxy)phenyl]-1,3-dihydroimidazol-2-one | 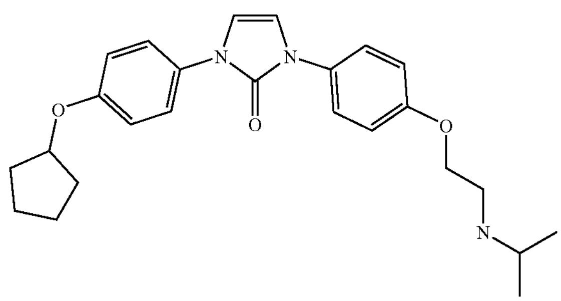 | C25H31N3O3 | 421.54 |
| 187 | 1-(4-Cyclopentyloxyphenyl)-3-{4-[2-(4-ethylpiperazin-1-yl)ethoxy]phenyl}-1,3-dihydroimidazol-2-one | 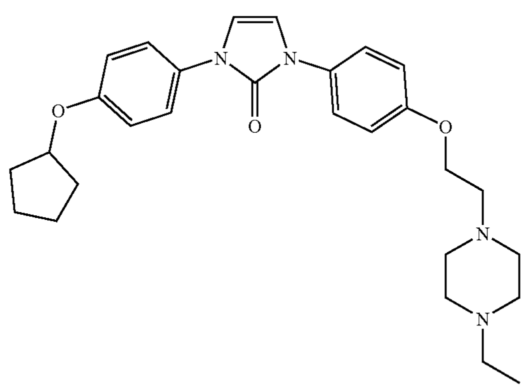 | C28H36N4O3 | 476.62 |

TABLE 5-continued

| Ex. No. | Name | Structure | Molecular formula | Molecular weight |
|---|---|---|---|---|
| 188 | 1-(4-Cyclopentyloxyphenyl)-3-{4-[2-(2,5-dimethylpyrrolidin-1-dihydroimidazol-2-one | 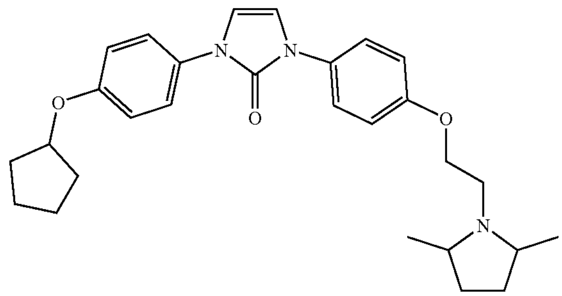 | C28H35N3O3 | 461.61 |
| 189 | 1-(4-Cyclopentyloxyphenyl)-3-{4-[2-(isopropylmethylamino)ethoxyl]phenyl)-1,3-dihydroimidazol-2-one | 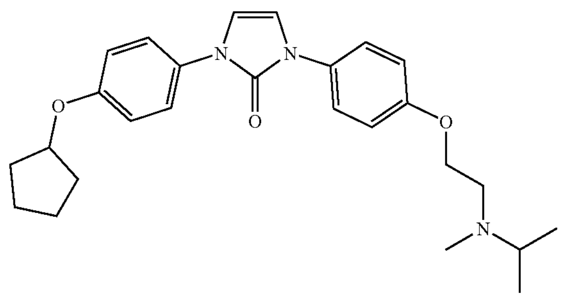 | C26H33N3O3 | 435.57 |
| 190 | 1-(4-Cyclopentyloxyphenyl)-3-{4-[2-((R)-2-methoxymethylpyrrolidin-1-yl)ethoxy]phenyl}-1,3-dihydroimidazol-2-one | Chiral | C28H35N3O4 | 477.61 |
| 191 | 1-{4-[2-(7-Azabicyclo[2.2.1]hept-7-yl)ethoxyl]phenyl}-3-(4-cyclopentyloxyphenyl)-1,3-dihydroimidazol-2-one | 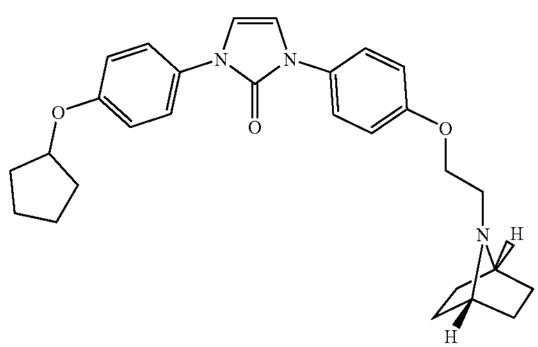 | C28H33N3O3 | 459.59 |

TABLE 5-continued

| Ex. No. | Name | Structure | Molecular formula | Molecular weight |
|---|---|---|---|---|
| 192 | 1-(4-Cyclopentyloxyphenyl)-3-{4-[2-(3-dimethylaminopyrrolidin-1-yl)ethoxy]phenyl}-1,3-dihydroimidazol-2-one | 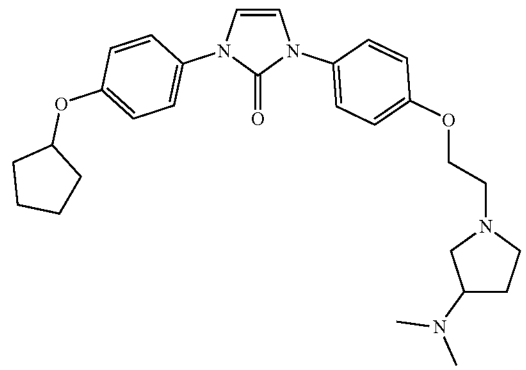 | C28H36N4O3 | 476.62 |
| 193 | N-[1-(2-{4-[3-(4-Cyclopentyloxyphenyl)-2-oxo-2,3-dihydroimidazol-1-yl]phenoxy}-ethyl)pyrrolidin-3-yl]acetamide | 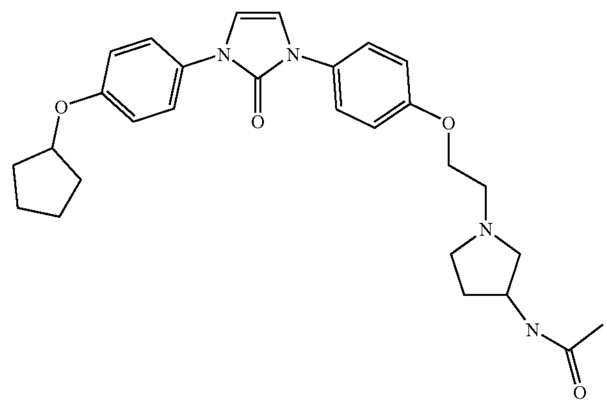 | C28H34N4O4 | 490.61 |
| 194 | 1-(4-Cyclopentyloxyphenyl)-3-{4-[2-(4-hydroxy-4-phenylpiperidin-1-yl)ethoxy]phenyl}-1,3-dihydroimidazol-2-one | 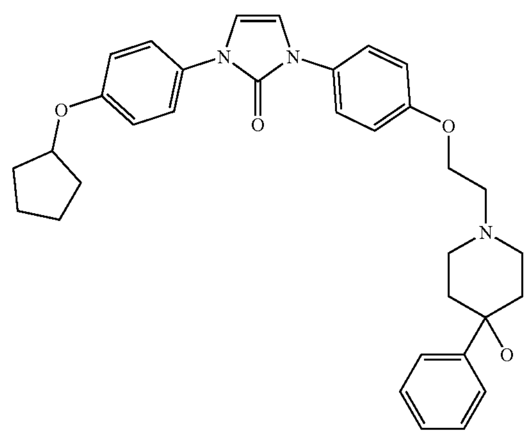 | C33H37N3O4 | 539.68 |
| 195 | 1-(4-Cyclopentyloxyphenyl)-3-{4-[2-(3-hydroxypyrrolidin-1-yl)ethoxy]phenyl}-1,3-dihydroimidazol-2-one | 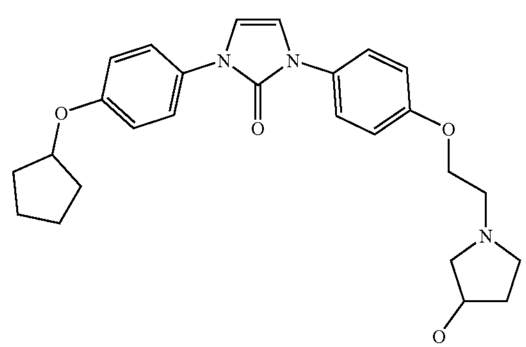 | C26H31N3O4 | 449.55 |

TABLE 5-continued

| Ex. No. | Name | Structure | Molecular formula | Molecular weight |
|---|---|---|---|---|
| 196 | 1-(4-Cyclopentyloxyphenyl)-3-{4-[2-(2-methylpyrrolidin-1-yl)ethoxy]phenyl}-1,3-dihydroimidazol-2-one | 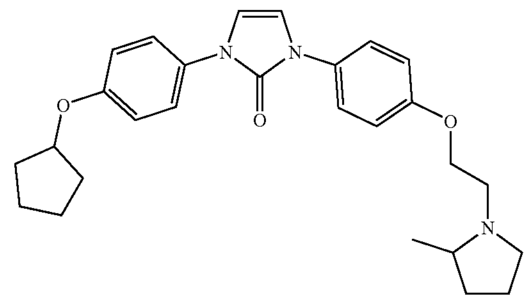 | C27H33N3O3 | 447.58 |
| 197 | Dimethyl (S)-1-(2-{4-[3-(4-cyclopentyloxyphenyl)-2-oxo-2,3-dihydroimidazol-1-yl]phenoxy}ethyl)pyrrrolidin-2-carboxamide | Chiral | C29H36N4O4 | 504.63 |
| 198 | 1-(4-Cyclopentyloxyphenyl)-3-(4-{2-[(2-methoxy-ethyl)methylamino]ethoxy}-phenyl)-1,3-dihydroimidazol-2-one | 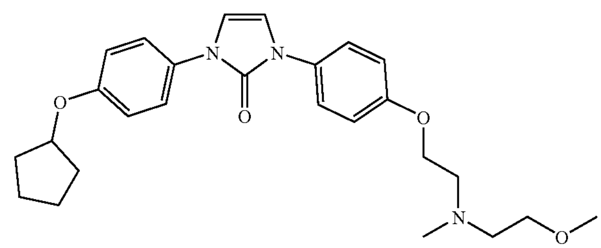 | C26H33N3O4 | 451.57 |
| 199 | 1-(4-Cyclopentyloxyphenyl)-3-{4-[2-(2-methylimidazol-1-yl)ethoxy]phenyl}-1,3-dihydroimidazol-2-one | 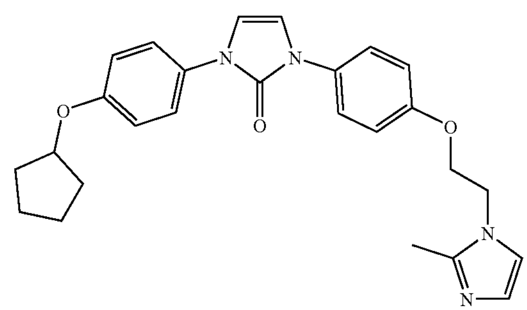 | C26H28N4O3 | 444.54 |
| 200 | 1-(4-Cyclopentyloxyphenyl)-3-{4-[2-(4-methylimidazol-1-yl)ethoxy]phenyl}-1,3-dihydroimidazol-2-one | 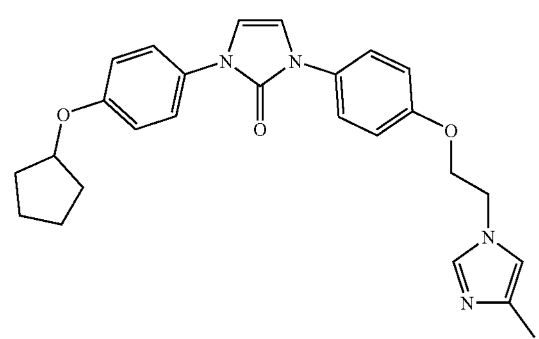 | C26H28N4O3 | 444.54 |

TABLE 5-continued

| Ex. No. | Name | Structure | Molecular formula | Molecular weight |
|---|---|---|---|---|
| 201 | 1-(4-Cyclopentyloxyphenyl)-3-{4-[2-(2-ethylimidazol-1-yl)ethoxy]phenyl}-1,3-dihydroimidazol-2-one | 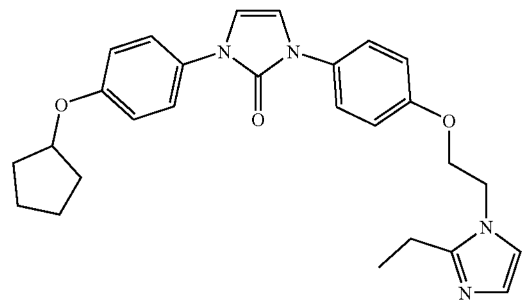 | C27H30N4O3 | 458.57 |
| 202 | 1-(4-Cyclopentyloxyphenyl)-3-{4-[2-(2,4-dimethylimidazol-1-yl)ethoxy]phenyl}-1,3-dihydroimidazol-2-one | 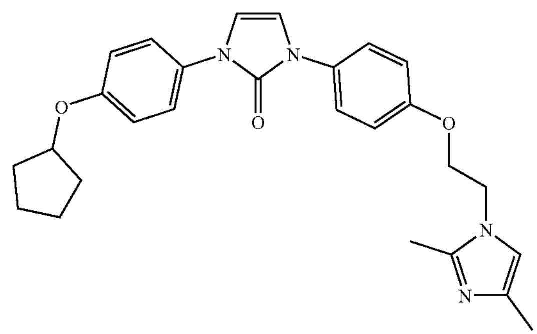 | C27H30N4O3 | 458.57 |
| 203 | 1-{4-[2-(2-Chloroimidazol-1-yl)ethoxy]phenyl}-3-(4-cyclopentyloxyphenyl)-1,3-dihydroimidazol-2-one | 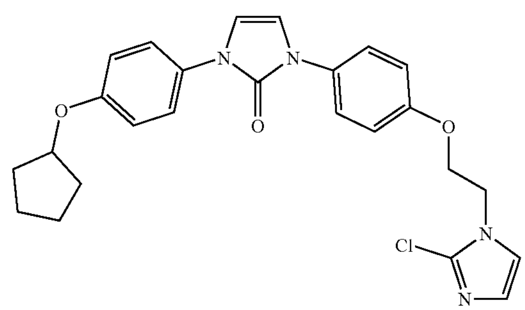 | C25H25ClN4O3 | 464.96 |
| 204 | 1-(4-Cyclopentyloxyphenyl)-3-{4-[2-(2-ethyl-4-methylimidazol-1-yl)ethoxy]phenyl}-1,3-dihydroimidazol-2-one | 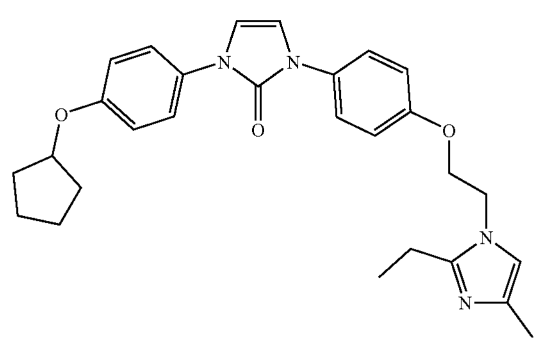 | C28H32N4O3 | 472.59 |

TABLE 5-continued

| Ex. No. | Name | Structure | Molecular formula | Molecular weight |
|---|---|---|---|---|
| 205 | 1-(4-Cyclopentyloxyphenyl)-3-{4-[2-(2-isopropylimidazol-1-yl)ethoxy]phenyl}-1,3-dihydroimidazol-2-one | 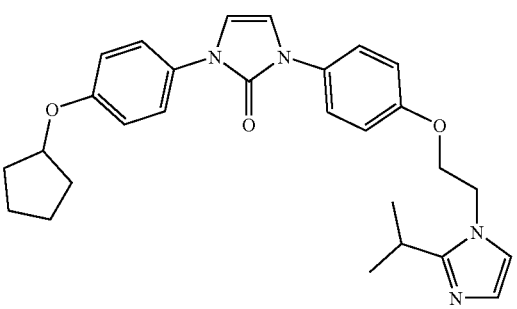 | C28H32N4O3 | 472.59 |
| 206 | 1-(4-Cyclopentyloxyphenyl)-3-{4-[2-(2,4,5-trimethylimidazol-1-yl)ethoxy]phenyl}-1,3-dihydroimidazol-2-one | 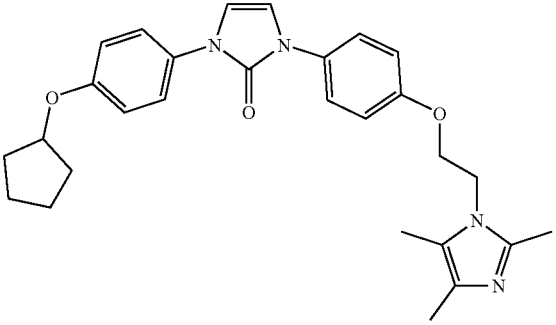 | C28H32N4O3 | 472.59 |
| 207 | 1-(4-Cyclopentyloxyphenyl)-3-{4-[2-(2-nitroimidazol-1-yl)ethoxy]-phenyl}-1,3-dihydroimidazol-2-one | 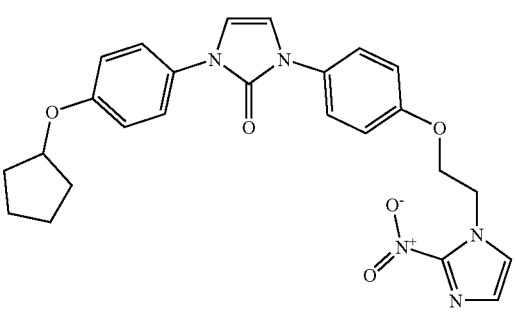 | C25H25N5O5 | 475.51 |
| 208 | 1-(4-Cyclopentyloxyphenyl)-3-{4-[2-(4-nitroimidazol-1-yl)ethoxy]-phenyl}-1,3-dihydroimidazol-2-one | 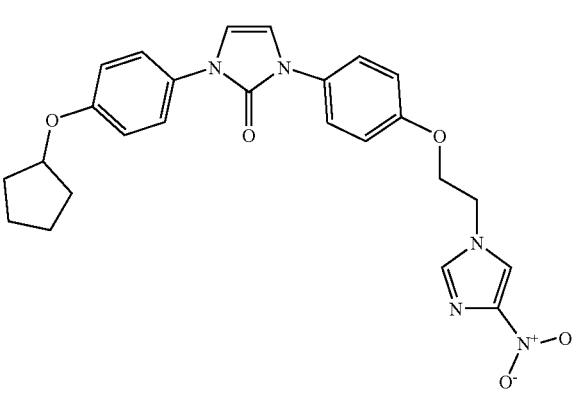 | C25H25N5O5 | 475.51 |

TABLE 5-continued

| Ex. No. | Name | Structure | Molecular formula | Molecular weight |
|---|---|---|---|---|
| 209 | 1-(4-Cyclopentyloxyphenyl)-3-{4-[2-(2-methyl-4-nitroimidazol-1-yl)ethoxy]phenyl}-1,3-dihydroimidazol-2-one | 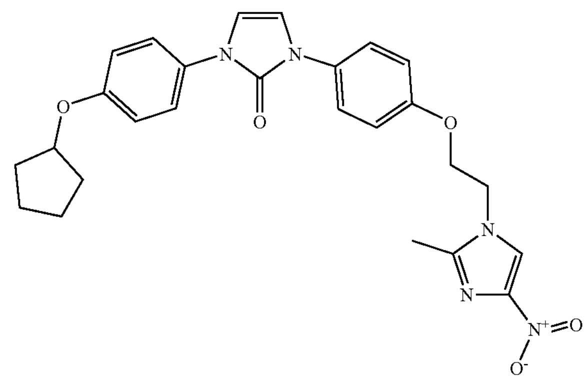 | C26H27N5O5 | 489.54 |
| 210 | 1-(4-Cyclopentyloxyphenyl)-3-{4-[2-(5-methyl-4-nitroimidazol-1-yl)ethoxy]phenyl}-1,3-dihydroimidazol-2-one | 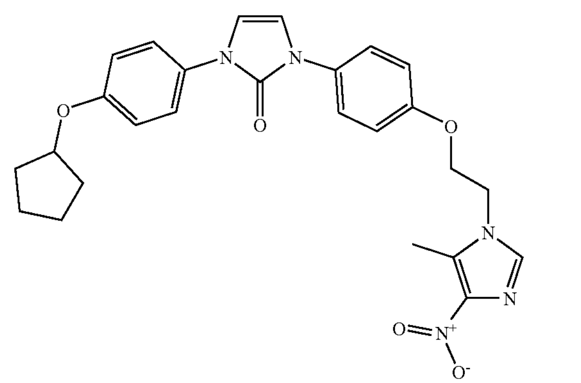 | C26H27N5O5 | 489.54 |
| 211 | 1-(4-Cyclopentyloxyphenyl)-3-{4-[2-(4,5-dichloroimidazol-1-yl)ethoxy]phenyl}-1,3-dihydroimidazol-2-one | 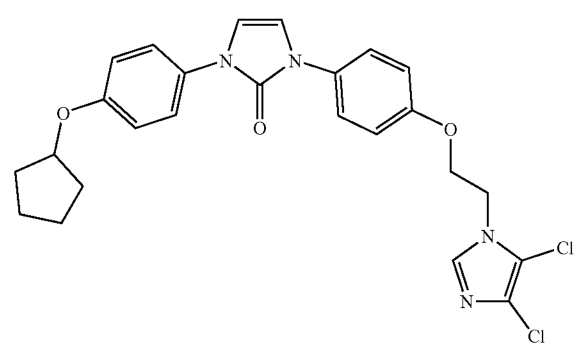 | C25H24Cl2N4O3 | 499.40 |
| 212 | 1-(4-Cyclopentyloxyphenyl)-3-{4-[2-(2-phenylimidazol-1-yl)ethoxy]phenyl}-1,3-dihydroimidazol-2-one | 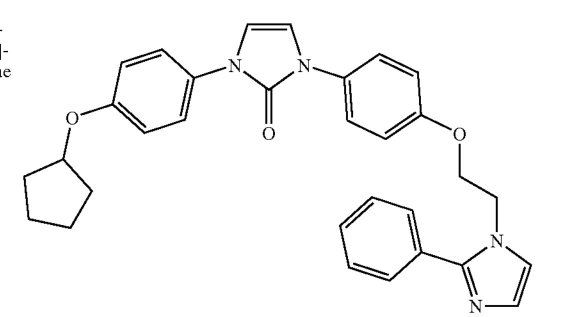 | C31H30N4O3 | 506.61 |

TABLE 5-continued

| Ex. No. | Name | Structure | Molecular formula | Molecular weight |
|---|---|---|---|---|
| 213 | 1-(4-Cyclopentyloxyphenyl)-3-{4-[2-(4-phenylimidazol-1-yl)ethoxy]phenyl}-1,3-dihydroimidazol-2-one | 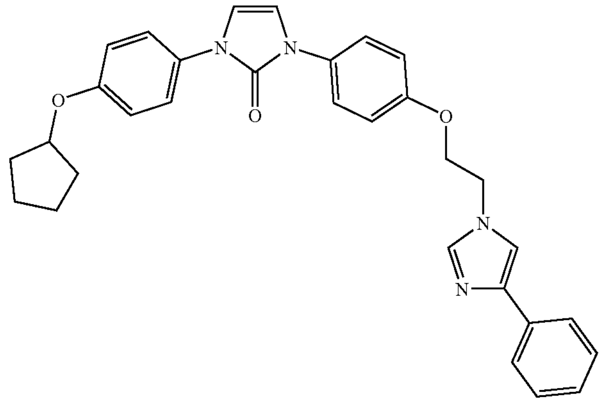 | C31H30N4O3 | 506.61 |
| 214 | 1-(4-Cyclopentyloxyphenyl)-3-{4-[2-(2-methyl-4,5-dihydroimidazol-1-yl)ethoxy]phenyl}-1,3-dihydroimidazol-2-one | 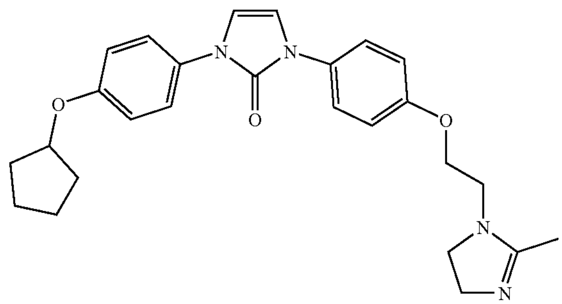 | C26H30N4O3 | 446.55 |
| 215 | 1-(4-Cyclopentyloxyphenyl)-3-{4-[2-(4,4-dimethyl-4,5-dihydroimidazol-1-yl)ethoxy]phenyl}-1,3-dihydroimidazol-2-one | 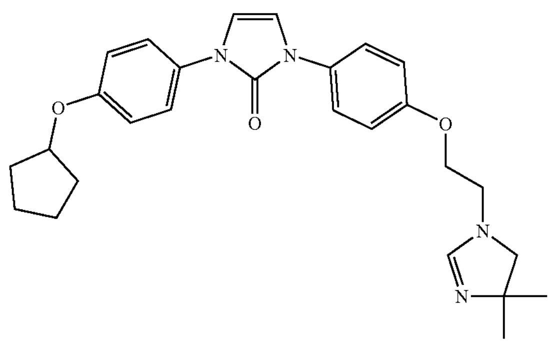 | C27H32N4O3 | 460.58 |

EXAMPLE 216

1-(4-Aminophenyl)-3-(4-phenoxyphenyl)-1,3-dihydroimidazol-2-one

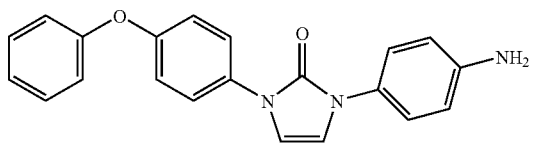

A solution of N-{4-[2-oxo-3-(4-phenoxyphenyl)-2,3-dihydroimidazol-1-yl]phenyl}acetamide (4.0 g) in ethanol (100 ml) was heated to reflux with hydrochloric acid (20% strength, 30 ml) for 16 hours. After cooling, ammonia solution (10% strength) was added until the reaction was basic. The precipitated solid was filtered off and dried in a vacuum oven at 40° C. The product with the molecular weight of 343.39 (C$_{21}$H$_{17}$N$_3$O$_2$); MS (ESI): 344 ([M+H]$^+$) was obtained in this way.

N-{4-[2-Oxo-3-(4-phenoxyphenyl)-2,3-dihydroimidazol-1-yl]phenyl}acetamide

4-Acetaminoaniline was reacted with carbonyldiimidazole and (2,2-dimethoxyethyl)-(4-phenoxyphenyl)amine as described in example 92, followed by treatment of the crude product with trifluoroacetic acid at 80° C. The product is precipitated on addition of ethyl acetate/heptane 1:1. The precipitated solid was filtered off and dried in a vacuum oven at 40° C. The product with the molecular weight of 385.43 (C$_{23}$H$_{17}$N$_3$O$_2$); MS (ESI): 386 ([M+H]$^+$) was obtained in this way.

EXAMPLE 217

2-Dimethylamino-N-{4-[2-oxo-3-(4-phenoxyphenyl)-2,3-dihydroimidazol-1-yl]phenyl}acetamide

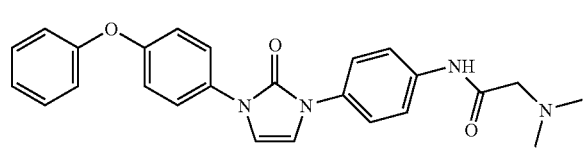

TOTU (327 mg) was added to a solution of 1-(4-aminophenyl)-3-(4-phenoxyphenyl)-1,3-dihydroimidazol-2-one (343 mg) in DMF (3 ml) at 0° C. After 10 minutes, Hünig base (130 mg) and then a solution of dimethylglycine (103 mg) in DMF (1 ml) was added. After a reaction time of 12 hours at room temperature, the mixture was mixed with water and extracted with ethyl acetate. The organic phase was washed with sodium bicarbonate solution, dried over magnesium sulfate and concentrated. The residue was purified by preparative HPLC. The product with the molecular weight of 428.50 ($C_{25}H_{24}N_4O_3$); MS (ESI): 429 ([M+H]$^+$) was obtained as hydrotrifluoroacetate in this way.

EXAMPLE 218

N-{4-[2-Oxo-3-(4-phenoxyphenyl)-2,3-dihydroimidazol-1-yl]phenyl}-2-piperidin-1-ylacetamide

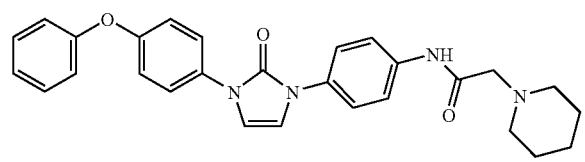

1-(4-Aminophenyl)-3-(4-phenoxyphenyl)-1,3-dihydroimidazol-2-one was reacted with piperidin-1-ylacetic acid as described in example 217. The product with the molecular weight of 468.56 ($C_{28}H_{28}N_4O_3$); MS (ESI): 469 ([M+H]$^+$) was obtained as hydrotrifluoroacetate in this way.

EXAMPLE 219

3-Methylamino-N-{4-[2-oxo-3-(4-phenoxy-phenyl)-2,3-dihydroimidazol-1-yl]-phenyl}-propionamide

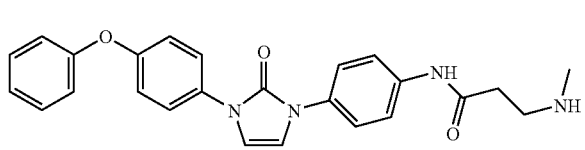

1-(4-Aminophenyl)-3-(4-phenoxyphenyl)-1,3-dihydroimidazol-2-one was reacted with methylaminopropionic acid as described in example 217. The product with the molecular weight of 428.50 ($C_{25}H_{24}N_4O_3$); MS (ESI): 429 ([M+H]$^+$) was obtained as hydrotrifluoroacetate in this way.

EXAMPLE 220

3-(2-Methyl-4-nitro-imidazol-1-yl)-N-{4-[2-oxo-3-(4-phenoxy-phenyl)-2,3-dihydroimidazol-1-yl]-phenyl-propionamide

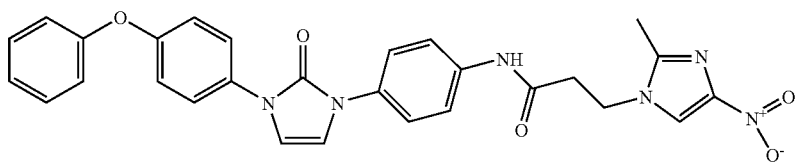

1-(4-Aminophenyl)-3-(4-phenoxyphenyl)-1,3-dihydroimidazol-2-one was reacted with 2-methyl-4-nitro-imidazol-1-yl-propionic acid as described in example 217. The product with the molecular weight of 524.54 ($C_{28}H_{24}N_6O_5$); MS (ESI): 525 ([M+H]$^+$) was obtained as hydrotrifluoroacetate in this way.

EXAMPLE 221

2-(2,5-Dioxo-imidazolidin-1-yl)-N-{4-[2-oxo-3-(4-phenoxy-phenyl)-2,3-dihydroimidazol-1-yl]-phenyl}-acetamide

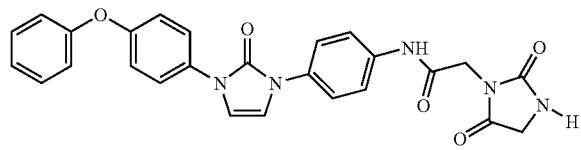

1-(4-Aminophenyl)-3-(4-phenoxyphenyl)-1,3-dihydroimidazol-2-one was reacted with 2-(2,5-dioxo-imidazolidin-1-yl acetic acid as described in example 217. The product with the molecular weight of 483.49 ($C_{26}H_{21}N_5O_5$); MS (ESI): 484 ($[M+H]^+$) was obtained as hydrotrifluoroacetate in this way.

EXAMPLE 222

Ethyl 1-({4-[2-oxo-3-(4-phenoxy-phenyl)-2,3-dihydro-imidazol-1-yl]-phenylcarbamoyl}-ethyl)-piperidine-4-carboxylate

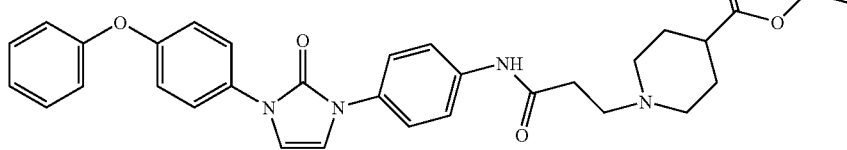

1-(4-Aminophenyl)-3-(4-phenoxyphenyl)-1,3-dihydroimidazol-2-one was reacted with ethyl 1-carboxyethylpiperidine-4-carboxylate as described in example 217. The product with the molecular weight of 544.65 ($C_{32}H_{34}N_4O_5$); MS (ESI): 555 ($[M+H]^+$) was obtained as hydrotrifluoroacetate in this way.

EXAMPLE 223

2-(Acetylmethylamino)-N-{4-[2-oxo-3-(4-phenoxyphenyl)-2,3-dihydroimidazol-1-yl]phenyl}acetamide

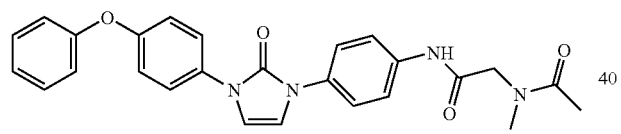

1-(4-Aminophenyl)-3-(4-phenoxyphenyl)-1,3-dihydroimidazol-2-one was reacted with (acetylmethylamino) acetic acid as described in example 217. The product with the molecular weight of 456.51 ($C_{26}H_{24}N_4O_4$); MS (ESI): 457 ([M+H] ) was obtained as hydrotrifluoroacetate in this way.

What is claimed is:

1. A compound of formula (I)

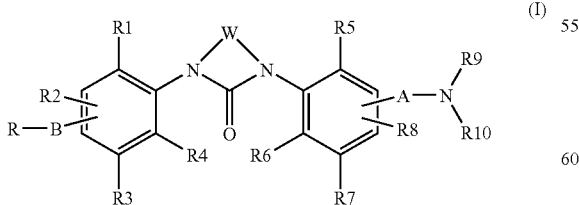

wherein

R is ($C_1$–$C_8$)-alkyl, ($C_0$–$C_8$)-alkylene-aryl, ($C_3$–$C_8$)-cycloalkyl, ($C_1$–$C_4$)-alkoxy-($C_1$–$C_4$)-alkyl, ($C_2$–$C_8$)-alkenyl, ($C_2$–$C_8$)-alkynyl, a 3- to 12-membered mono-, bi- or spirocyclic ring optionally containing one heteroatoms selected from the group consisting of N, O, and S, and wherein the 3- to 12-membered ring is optionally substituted by F, Cl, Br, $NO_2$, $CF_3$, $OCF_3$, CN, ($C_1$–$C_6$)-alkyl, aryl, CON(R11)(R12), N(R13)(R14), OH, O—($C_1$–$C_6$)-alkyl, S—($C_1$–$C_6$)-alkyl, or N(R15) CO($C_1$–$C_6$)-alkyl;

R11, R12, R13, R14 and R15 independently are H or ($C_1$–$C_6$)-alkyl;

B is a bond or a linker of one or two radicals selected from the group consisting of $(C(R19)(R20))_i$, C(OR21)(R22), O, N(R23), S, SO, $SO_2$, and CO;

i is 1, 2 or 3;

R19, R20, R21, R22 and R23 independently are H, ($C_1$–$C_6$)-alkyl or aryl;

R1, R2, R3, and R4 independently are H, F, Cl, Br, I, OH, $CF_3$, $NO_2$, CN, $OCF_3$, O—($C_1$–$C_6$)-alkyl, O—($C_1$–$C_4$)-alkoxy-($C_1$–$C_4$)-alkyl, S—($C_1$–$C_6$)-alkyl, ($C_1$–$C_6$)-alkyl, ($C_2$–$C_6$)-alkenyl, ($C_3$–$C_8$)-cycloalkyl, O—($C_3$–$C_8$)-cycloalkyl, ($C_3$–$C_8$)-cycloalkenyl, O—($C_3$–$C_8$)-cycloalkenyl, ($C_2$–$C_6$)-alkynyl, ($C_0$–$C_8$)-alkylene-aryl, O—($C_0$–$C_8$)-alkylene-aryl, S-aryl, N(R24)(R25), $SO_2$—$CH_3$, CON(R26)(R27), N(R28) CO(R29), N(R30)$SO_2$(R31) or CO(R32);

R24, R25, R26, R27, R28 and R30 independently are H or ($C_1$–$C_6$)-alkyl;

R29, R31, and R32 independently are H, ($C_1$–$C_6$)-alkyl or aryl;

W is —$(CH_2)_n$—, —CH=CH—, —CH=N— or —N=CH—;

n is 2, 3, 4 or 5;

R5, R6, R7 and R8 independently are H, F, Cl, Br, I, OH, $CF_3$, $NO_2$, CN, $OCF_3$, O—($C_1$–$C_6$)-alkyl, O—($C_1$–$C_4$)-alkoxy-($C_1$–$C_4$)-alkyl, S—($C_1$–$C_6$)-alkyl, ($C_1$–$C_6$)-alkyl, ($C_2$–$C_6$)-alkenyl, ($C_3$–$C_8$)-cycloalkyl, O—($C_3$–$C_8$)-cycloalkyl, ($C_3$–$C_8$)-cycloalkenyl, O—($C_3$–$C_8$)-cycloalkenyl, ($C_2$–$C_6$)-alkynyl, ($C_0$–$C_8$)-alkylene-aryl, O—($C_0$–$C_8$)-alkylene-aryl, S-aryl, N(R33)(R34), $SO_2$—$CH_3$, ) CON(R35)(R36), N(R37) CO(R38), N(R39)$SO_2$(R40), CO(R41) or a 5- to 7-membered heterocycle having 1 heteroatom selected from the group consisting of O, N and S;

R33 and R34 independently are H or ($C_1$–$C_6$)-alkyl, or

R33 and R34 form together with the nitrogen atom to which they are bonded a 5- or 6-membered ring wherein when R33 and R34 form together with the nitrogen to which they are bonded a 6-membered ring, one $CH_2$ group of the 6-membered ring optionally is O or S;

R35, R36, R37 and R39 independently are H or ($C_1$–$C_6$)-alkyl;

R38, R40 and R41 independently are H, ($C_1$–$C_6$)-alkyl or aryl;

A is a chain —(C(R42)(R43))$_m$— wherein 0 to 2 members of the chain are optionally replaced by an element selected from the group consisting of O, S, N(R44), CO and SO$_2$;

m is 0, 1, 2, 3, 4 or 5;

R42, R43, R44 independently are H, (C$_1$–C$_6$)-alkyl or aryl;

R9 and R10 independently are H, (C$_1$–C$_8$)-alkyl, —(CH$_2$)$_o$—R45, (C$_1$–C$_4$)-alkoxy-C$_1$–C$_4$)-alkyl, aryloxy-(C$_1$–C$_4$)-alkyl, (C$_3$–C$_8$)-alkenyl, (C$_3$–C$_8$)-alkynyl, CO—(C$_1$–C$_8$)-alkyl, CO—(CH$_2$)$_o$R45, CO—(C$_1$–C$_4$)-alkoxy-(C$_1$–C$_4$)-alkyl, CO-aryloxy-(C$_1$–C$_4$)-alkyl, CO—(C$_2$–C$_8$)-alkenyl, CO—(C$_2$–C$_8$)-alkynyl, or R9 and R10 form together with the nitrogen atom to which they are bonded a 4- to 10-membered mono-, bi- or spirocyclic ring wherein said ring, apart from the nitrogen atom, may optionally contain 0 to 4 additional heteroatoms selected from the group consisting of O, N and S and wherein said ring optionally is substituted by F, Cl, Br, CF$_3$, NO$_2$, CN, (C$_1$–C$_6$)-alkyl, O—(C$_1$–C$_8$)-alkyl, (C$_1$–C$_4$)-alkoxy-(C$_1$–C$_4$)-alkyl, (C$_0$–C$_8$)-alkylene-aryl, oxo, CO(R46), CON(R47)(R48), OH, N(R50)CO(C$_1$–C$_6$)-alkyl, N(R51)(R52) or SO$_2$CH$_3$;

R46, R47, R48, R50, R51 and R52 independently are H or (C$_1$–C$_4$)-alkyl;

o is 0, 1, 2, 3, 4, 5 or 6;

R45 is OH, CH(aryl)$_2$, a 3- to 12-membered mono- or bicyclic ring which optionally contains one or more heteroatoms selected from the group consisting of N, O and S wherein the 3- to 12-membered ring optionally is substituted by F, Cl, Br, I, OH, CF$_3$, NO$_2$, CN, OCF$_3$, oxo, O—(C$_1$–C$_6$)-alkyl, (C$_1$–C$_4$)-alkoxy-(C$_1$–C$_4$)-alkyl, S—(C$_1$–C$_6$)-alkyl, (C$_1$–C$_6$)-alkyl, (C$_2$–C$_6$)-alkenyl, (C$_3$–C$_8$)-cycloalkyl, O—(C$_3$–C$_8$)-cycloalkyl, (C$_3$–C$_8$)-cycloalkenyl, O—(C$_3$–C$_8$)-cycloalkenyl, (C$_2$–C$_6$)-alkynyl, (C$_0$–C$_8$)-alkylene-aryl, O—(C$_0$–C$_8$)-alkylene-aryl, S-aryl, N(R51)(R52), SO$_2$—CH$_3$ or COOH; or a pharmaceutically acceptable salt of the compound of formula 1.

2. The compound according to claim 1 wherein

R is (C$_1$–C$_6$)-alkyl, (C$_0$–C$_2$)-alkylene-aryl, (C$_3$–C$_8$)-cycloalkyl, (C$_2$–C$_6$)-alkenyl, (C$_5$–C$_8$)-cycloalkenyl, (C$_7$–C$_8$)-bicycloalkenyl, (C$_2$–C$_6$)-alkynyl or a 3- to 7-membered ring optionally containing one heteroatom selected form the group consisting of N, O, and S, and wherein the 3- to 7-membered ring is optionally substituted by F, Cl, Br, NO$_2$, CF$_3$, OCF$_3$, CN, (C$_1$–C$_6$)-alkyl, CON(R11)(R12), N(R13)(R14), OH, O—(C$_1$–C$_6$)-alkyl or N(R15)CO(C$_1$–C$_6$)-alkyl;

B is a bond O, S, SO$_2$, CO, OCH(R20), N(R23), CH$_2$ or CH$_2$CH$_2$;

R20 and R23 independently are H or (C$_1$–C$_6$)-alkyl;

R1, R2, R3, and R4 independently are H, F, Cl, Br, OH, CF$_3$, NO$_2$, CN, OCF$_3$, O—(C$_1$–C$_6$)-alkyl, O—(C$_1$–C$_4$)-alkoxy-(C$_1$–C$_4$)-alkyl, S—(C$_1$–C$_6$)-alkyl, (C$_1$–C$_6$)-alkyl, (C$_0$–C$_2$)-alkylene-aryl, O—(C$_0$–C$_2$)-alkylene-aryl, N(R24)(R25), SO$_2$—CH$_3$, CON(R26)(R27), N(R28)CO(R29) or CO(R32);

R29 and R32 independently are H, (C$_1$–C$_6$)-alkyl or aryl;

n is 2, 3 or 4;

R5, R6, R7 and R8 independently are H, F, Cl, Br, OH, CF$_3$, NO$_2$, CN, OCF$_3$, O—(C$_1$–C$_6$)-alkyl, (C$_1$–C$_6$)-alkyl, (C$_0$–C$_2$)-alkylene-aryl, O—(C$_0$–C$_2$)-alkylene-aryl, or CO(R41);

R41 is (C$_1$–C$_6$)-alkyl or aryl;

A is a chain —(C(R42)(R43))$_m$— wherein 1 to 2 members of the chain are optionally replaced by an element selected from the group consisting of O, N(R44) and CO;

m is 3 or 4;

R9 and R10 independently are H, (C$_1$–C$_8$)-alkyl, —(CH$_2$)$_o$—R45, (C$_1$–C$_4$)-alkoxy-(C$_1$–C$_4$)-alkyl, aryloxy-(C$_1$–C$_4$)-alkyl, (C$_3$–C$_8$)-alkenyl, (C$_3$–C$_8$)-alkynyl, CO—(C$_1$–C$_8$)-alkyl or CO—(CH$_2$)$_o$R45; or R9 and R10 form together with the nitrogen atom to which they are bonded a 4- to 10-membered mono-, bi- or spirocyclic ring wherein said ring, apart from the nitrogen atom, may optionally contain 0 to 2 additional heteroatoms selected from the group consisting of O, N and S and wherein said ring optionally is substituted by F, Cl, Br, CF$_3$, CN, (C$_1$–C$_6$)-alkyl, O—(C$_1$–C$_8$)-alkyl, (C$_1$–C$_4$)-alkoxy-(C$_1$–C$_4$)-alkyl, (C$_0$–C$_2$)-alkylene-aryl, oxo, CO(R46), CON(R47)(R48), OH, N(R50)CO(C$_1$–C$_6$)-alkyl, N(R51)(R52) or SO$_2$CH$_3$;

o is 0, 1, 2, 3 or 4;

R45 is OH, a 3- to 12-membered mono- or bicyclic ring which optionally contains one or two heteroatoms selected from the group consisting of N, O and S wherein the 3- to 12-membered ring optionally is substituted by F, Cl, Br, OH, CF$_3$, NO$_2$, CN, OCF$_3$, oxo, O—(C$_1$–C$_6$)-alkyl, (C$_1$–C$_6$)-alkyl, (C$_2$–C$_6$)-alkenyl, (C$_0$–C$_2$)-alkylene-aryl, O—(C$_0$–C$_2$)-alkylene-aryl, N(R51)(R52), SO$_2$—CH$_3$ or COOH.

3. The compound according to claim 2 wherein

R is (C$_1$–C$_6$)-alkyl, (C$_3$–C$_8$)-cycloalkyl, or a 5- to 6-membered mono- or bicyclic ring optionally containing one heteroatom selected from the group consisting of N, O, and S, wherein the 5- to 6-membered ring is optionally substituted by F, Cl, Br, NO$_2$, CF$_3$, OCF$_3$, CN, (C$_1$–C$_6$)-alkyl or O—(C$_1$–C$_6$)-alkyl;

B is a bond, O, S, CO OCH$_2$, N(R23) or CH$_2$;

R23 is H or (C$_1$–C$_6$)-alkyl;

R1, R2, R3, and R4 independently are H, F, Cl, Br, CF$_3$, O—(C$_1$–C$_6$)-alkyl or (C$_1$–C$_6$)-alkyl;

W is —CH═CH— or —N═CH—;

R5, R6, R7 and R8 independently are H, F, Cl, Br, OH, CF$_3$, NO$_2$, CN, OCF$_3$ or O—(C$_1$–C$_6$)-alkyl;

A is a chain —(C(R42)(R43))$_m$— wherein 1 member of the chain is optionally replaced by an element selected from the group consisting of O and N(R44);

R9 and R10 independently are H, (C$_1$–C$_8$)-alkyl, —(CH$_2$)$_o$—R45 or CO—(C$_1$–C$_8$)-alkyl; or R9 and R10 form together with the nitrogen atom to which they are bonded a 4- to 10-membered mono-, bi- or spirocyclic ring wherein said ring, apart from the nitrogen atom, may optionally contain 0 to 2 additional heteroatoms selected from the group consisting of O, N and S, and wherein said ring optionally is substituted by F, (C$_1$–C$_6$)-alkyl, O—(C$_1$–C$_8$)-alkyl, oxo, CO(R46), CON(R47)(R48), OH, N(R50)CO(C$_1$–C$_6$)-alkyl or N(R51)(R52);

R45 is OH, a 5- to 10-membered mono- or bicyclic ring which optionally contains one or two heteroatoms selected from the group consisting of N, O and S, wherein the 5- to 10-membered ring optionally is substituted by F, Cl, Br, OH, CF$_3$, oxo, O—(C$_1$–C$_6$)-alkyl, (C$_1$–C$_6$)-alkyl, (C$_0$–C$_2$)-alkylene-aryl, O—(C$_0$–C$_2$)-alkylene-aryl or N(R51)(R52).

4. The compound according to claim 3 wherein W is —CH═CH—.

5. The compound according to claim 3 wherein m is 3 and R42, R43 and R44 are H.

6. The compound according to claim 3 wherein R5, R6, R7 and R8 are H.

7. The compound according to claim 3 wherein A and B are each disposed in the para position relative to the central W-containing heterocycle.

8. The compound according to claim 7 which is 1-[4-(2-dimethylaminoethoxy)-phenyl]-3-(4-phenoxyphenyl)-1,3-dihydroimidazol-2-one.

9. A pharmaceutical composition comprising a pharmaceutical carrier and a therapeutically effective amount of a compound, or a pharmaceutically acceptable salt thereof, of formula (I)

wherein
R is $(C_1-C_8)$-alkyl, $(C_0-C_8)$-alkylene-aryl, $(C_3-C_8)$-cycloalkyl, $(C_1-C_4)$-alkoxy-$(C_1-C_4)$-alkyl, $(C_2-C_8)$-alkenyl, $(C_2-C_8)$-alkynyl, a 3- to 12-membered mono-, bi- or spirocyclic ring optionally containing one heteroatom selected from the group consisting of N, O, and S, and wherein the 3- to 12-membered ring is optionally substituted by F, Cl, Br, $NO_2$, $CF_3$, $OCF_3$, CN, $(C_1-C_6)$-alkyl, aryl, CON(R11)(R12), N(R13)(R14), OH, O—$(C_1-C_6)$-alkyl, S—$(C_1-C_6)$-alkyl, or N(R15) CO$(C_1-C_6)$-alkyl;

R11, R12, R13, R14 and R15 independently are H or $(C_1-C_6)$-alkyl;

B is a bond or a linker of one or two radicals selected from the group consisting of $(C(R19)(R20))_i$, C(OR21)(R22), O, N(R23), S, SO, $SO_2$, and CO;

i is 1, 2 or 3;

R19, R20, R21, R22 and R23 independently are H, $(C_1-C_6)$-alkyl or aryl;

R1, R2, R3, and R4 independently are H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R24)(R25), $SO_2$—$CH_3$, CON(R26)(R27), N(R28)CO(R29), N(R30) $SO_2$(R31) or CO(R32);

R24, R25, R26, R27, R28 and R30 independently are H or $(C_1-C_6)$-alkyl;

R29, R31, and R32 independently are H, $(C_1-C_6)$-alkyl or aryl;

W is —$(CH_2)_n$—, —CH=CH—, —CH=N— or —N=CH—;

n is 2, 3, 4 or 5;

R5, R6, R7 and R8 independently are H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R33)(R34), $SO_2$—$CH_3$, CON(R35)(R36), N(R37) CO(R38), N(R39) $SO_2$(R40), CO(R41) or a 5- to 7-membered heterocycle having 1 heteroatom selected from the group consisting of O, N and S;

R33 and R34 independently are H or $(C_1-C_6)$-alkyl, or

R33 and R34 form together with the nitrogen atom to which they are bonded a 5- or 6-membered ring wherein when R33 and R34 form together with the nitrogen to which they are bonded a 6-membered ring, one $CH_2$ group of the 6-membered ring optionally is O or S;

R35, R36, R37 and R39 independently are H or $(C_1-C_6)$-alkyl;

R38, R40 and R41 independently are H, $(C_1-C_6)$-alkyl or aryl;

A is a chain —$(C(R42)(R43))_m$— wherein 0 to 2 members of the chain are optionally replaced by an element selected from the group consisting of O, S, N(R44), CO and $SO_2$;

m is 0, 1, 2, 3, 4 or 5;

R42, R43, R44 independently are H, $(C_1-C_6)$-alkyl or aryl;

R9 and R10 independently are H, $(C_1-C_8)$-alkyl, —$(CH_2)_o$—R45, $(C_1-C_4)$-alkoxy-$(C_1-C_4)$-alkyl, aryloxy-$(C_1-C_4)$-alkyl, $(C_3-C_8)$-alkenyl, $(C_3-C_8)$-alkynyl, CO—$(C_1-C_8)$-alkyl, CO—$(CH_2)_o$R45, CO—$(C_1-C_4)$-alkoxy-$(C_1-C_4)$-alkyl, CO-aryloxy-$(C_1-C_4)$-alkyl, CO—$(C_2-C_8)$-alkenyl, CO—$(C_2-C_8)$-alkynyl, or R9 and R10 form together with the nitrogen atom to which they are bonded a 4- to 10-membered mono-, bi- or spirocyclic ring wherein said ring, apart from the nitrogen atom, may optionally contain 0 to 4 additional heteroatoms selected from the group consisting of O, N and S and wherein said ring optionally is substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, $(C_0-C_8)$-alkylene-aryl, oxo, CO(R46), CON(R47)(R48), OH, N(R50)CO$(C_1-C_6)$-alkyl, N(R51)(R52) or $SO_2CH_3$;

R46, R47, R48, R50, R51 and R52 independently are H or $(C_1-C_4)$-alkyl;

o is 0, 1, 2, 3, 4, 5 or 6;

R45 is OH, CH(aryl)$_2$, a 3- to 12-membered mono- or bicyclic ring which optionally contains one or more heteroatoms selected from the group consisting of N, O and S wherein the 3- to 12-membered ring optionally is substituted by F, Cl, Br, I, OH, $CF_3$, $NO_2$, CN, $OCF_3$, oxo, O—$(C_1-C_6)$-alkyl, $(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R51)(R52), $SO_2$—$CH_3$ or COOH.

10. A pharmaceutical composition according to claim 9 further comprising a therapeutically effective amount of one or more compounds selected from the group consisting of an antiobesity agent, an appetite-regulating active ingredient, an antidiabetic and a hypoglycemic active ingredient.

11. A pharmaceutical composition according to claim 10 wherein said antiobesity agent or appetite-regulating active ingredient is selected from the group consisting of of leptin, modified leptin, dexamphetamine, amphetamine, fenfluramine, dexfenfluramine, sibutramine, the mono- and bis-demethylated active metabolites of sibutramine, orlistat, mazindol, diethylpropion and phenteramine.

12. A pharmaceutical composition according to claim 10 wherein said antidiabetic or hypoglycemic active ingredient is selected from the group consisting of insulin, a sulfonylurea, a biguanide, a meglitinide, a thiazolidinedione, an oxadiazolidinedione and an α-glucosidase inhibitor.

13. A compound of formula (I)

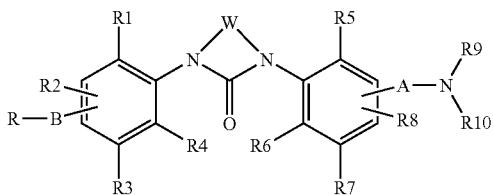

R is $(C_1-C_6)$-alkyl, $(C_3-C_8)$-cycloalkyl, or a 5- to 6-membered mono- or bicyclic ring optionally containing one or two heteroatoms selected from the group consisting of N, O, and S, wherein the 5- to 6-membered ring is optionally substituted by F, Cl, Br, $NO_2$, $CF_3$, $OCF_3$, CN, $(C_1-C_6)$-alkyl or $O-(C_1-C_6)$-alkyl;

B is a bond, O, S, $COOCH_2$, N(R23) or $CH_2$;

R23 is H or $(C_1-C_6)$-alkyl;

R1, R2, R3, and R4 independently are H, F, Cl, Br, $CF_3$, $O-(C_1-C_6)$-alkyl or $(C_1-C_6)$-alkyl;

W is —CH=CH— or —N=CH—;

R5, R6, R7 and R8 independently are H, F, Cl, Br, OH, $CF_3$, $NO_2$, CN, $OCF_3$ or $O-(C_1-C_6)$-alkyl;

A is a chain $-(C(R42)(R43))_m-$ wherein 1 member of the chain is optionally replaced by an element selected from the group consisting of O and N(R44);

m is 0, 1, 2, 3, 4 or 5;

R42, R43, and R44 independently are H, $(C_1-C_6)$-alkyl or aryl;

R9 and R10 independently are H, $(C_1-C_8)$-alkyl, $-(CH_2)_o-$R45 or CO—$(C_1-C_8)$-alkyl; or R9 and R10 form together with the nitrogen atom to which they are bonded a 4- to 10-membered mono-, bi- or spirocyclic ring wherein said ring, apart from the nitrogen atom, may optionally contain 0 to 2 additional heteroatoms selected from the group consisting of O, N and S, and wherein said ring optionally is substituted by F, $(C_1-C_6)$-alkyl, $O-(C_1-C_8)$-alkyl, oxo, CO(R46), CON(R47)(R48), OH, N(R50)CO($C_1-C_6$)-alkyl or N(R51)(R52);

R46, R47, R48, R50, R51, and R52 independently are H or $(C_1-C_4)$-alkyl;

o is 0, 1, 2, 3, 4, 5 or 6;

R45 is OH, a 5- to 10-membered mono- or bicyclic ring which optionally contains one or two heteroatoms selected from the group consisting of N, O and S, wherein the 5- to 10-membered ring optionally is substituted by F, Cl, Br, OH, $CF_3$, oxo, $O-(C_1-C_6)$-alkyl, $(C_1-C_6)$-alkyl, $(C_0-C_2)$-alkylene-aryl, $O-(C_0-C_2)$-alkylene-aryl or N(R51)(R52).

14. The compound according to claim 13 wherein W is —CH=CH—.

15. The compound according to claim 13 wherein m is 3 and R42, R43 and R44 are H.

16. The compound according to claim 13 wherein R5, R6, R7 and R8 are H.

17. The compound according to claim 13 wherein A and B are each disposed in the para position relative to the central W-containing heterocycle.

* * * * *